United States Patent
Bloom et al.

(10) Patent No.: US 6,262,090 B1
(45) Date of Patent: Jul. 17, 2001

(54) AMINOPYRIDINE-CONTAINING THIOUREA INHIBITORS OF HERPES VIRUSES

(75) Inventors: Jonathan Bloom, Nyack; Martin DiGrandi, Piermont; Russell Dushin, Garrison, all of NY (US); Stanley Lang, Carlsbad, CA (US); Bryan O'Hara, Norwood, NJ (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/444,896

(22) Filed: Nov. 22, 1999

Related U.S. Application Data

(60) Provisional application No. 60/150,698, filed on Dec. 9, 1998, provisional application No. 60/155,240, filed on Dec. 9, 1998, provisional application No. 06/228,808, filed on Dec. 9, 1998, provisional application No. 60/228,805, filed on Dec. 9, 1998, provisional application No. 60/155,192, filed on Dec. 9, 1998, provisional application No. 60/150,692, filed on Dec. 9, 1998, and provisional application No. 60/228,809, filed on Dec. 9, 1998.

(51) Int. Cl.$^7$ .................. A61K 31/44; A61K 31/405; C07D 211/72; C07D 235/26; C07D 207/34

(52) U.S. Cl. .................. 514/352; 514/353; 514/398; 514/415; 514/426; 546/307; 546/309; 548/308.1; 548/331.5; 548/326.5; 548/483; 548/557; 548/558

(58) Field of Search .................. 546/157, 307, 546/309; 514/352, 353, 398, 415, 426; 548/308.1, 331.5, 326.5, 483, 557, 558

(56) References Cited

U.S. PATENT DOCUMENTS 5,593,993    1/1997   Morin et al. .

FOREIGN PATENT DOCUMENTS

98/45259 * 10/1998 (WO) .

OTHER PUBLICATIONS

Roizman, B., Herpesviridaie. 2221–2230 (1996), Fields Virology.

Whitley, R.J., Herpes Simplex Viruses, 2297–2342 (1996), Fields Virology.

Arvin, A., Varicella–Zoster Virus, 2547–2585 (1996), Fields Virology.

Rickinson, A.B. et al., Epstein–Barr Virus, 2397–2446 (1996), Fields Virology.

Britt, W.J. et al., Cytomegalovirus, 2493–2523 (1996), Fields Virology.

Pellet, P.E. et al., Human Herpesvirus, 6, 2587–2608 (1996), Fields Virology.

Frenkel, N. et al., Human Herpesvirus, 7, 2609–2622 (1996), Fields Virology.

Neipel, F. et al., J. Virol., 71, No. 6, 4187–4192 (1996).

Bron, D. et al., Exp. Opin. Invest. Drugs, 5(3), 337–344 (1996).

Crumpacker, C., New England J. Med., 335, 721–729 (1996).

Sachs, S. et al., Exp. Opin. Invest. Drugs, 5(2), 169–183 (1996).

* cited by examiner

Primary Examiner—D. Margaret Seaman
(74) Attorney, Agent, or Firm—John W. Hogan, Jr.

(57) ABSTRACT

Compounds of the formula

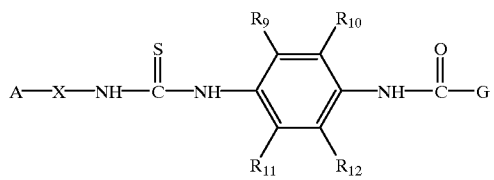

wherein

A is heteroaryl;

$R_9$–$R_{12}$ are independently hydrogen, alkyl of 1 to 4 carbon atoms, perhaloalkyl of 1 to 4 carbon atoms, halogen, alkoxy of 1 to 4 carbon atoms, or cyano, or $R_9$ and $R_{10}$ or $R_{11}$ and $R_{12}$ may be taken together to form aryl of 5 to 7 carbon atoms;

W is O, $NR_6$, or is absent;

G is aryl or heteroaryl; and

X is a bond X is a bond, —NH, alkyl of 1 to 6 carbon atoms, alkenyl of 1 to 6 carbon atoms, alkoxy of 1 to 6 carbon atoms, thioalkyl of 1 to 6 carbon atoms, alkylamino of 1 to 6 carbon atoms, or (CH)J; and J is alkyl of 1 to 6 carbon atoms, cycloalkyl of 3 to 7 carbon atoms, phenyl or benzyl; and n is an integer from 1 to 6; or a pharmaceutical acceptable salt thereof, useful in the treatment of diseases associated with herpes viruses including human cytomegalovirus, herpes simplex viruses, Epstein-Barr virus, varicella-zoster virus, human herpesviruses-6 and -7, and Kaposi herpesvirus.

23 Claims, No Drawings

AMINOPYRIDINE-CONTAINING THIOUREA INHIBITORS OF HERPES VIRUSES

This application claims the benefit of U.S. Provisional Application Nos. 60/150,698, 60/155,240, 60/228,808, 60/228,805, 60/155,192, 60/150,692, 60/228,809 each of which was filed Dec. 9, 1998. These applications are herein incorporated by reference in their entireties.

BACKGROUND OF THE INVENTION

Eight viruses have been identified which are members of the family Herpesviridae (reviewed in Roizman, B. 1996. Herpesviridae, p. 2221–2230. In B. N. Fields, D. M. Knipe, and P. M. Howley (ed.), Fields Virology, 3rd ed. Lippincott-Raven Publishers, Philadelphia, Pa.). Each member of this family is characterized by an enveloped virus containing proteinaceous tegument and nucleocapsid, the latter of which houses the viruses' relatively large double-stranded DNA genome (i.e. approximately 80–250 kilobases). Members of the human alphaherpesvirus subfamily are neurotropic and include herpes simplex virus type 1 (HSV-1) and type 2 (HSV-2), and varicella-zoster virus (VZV). The human betaherpesviruses are cytomegalovirus (HCMV), human herpesvirus 6 (HHV-6) and human herpesvirus 7 (HHV-7). The gammaherpesviruses are lymphotropic and include Epstein-Barr virus (EBV) and Kaposi's herpesvirus (HHV-8). Each of these herpesviruses is causally-related to human disease, including herpes labialis and herpes genitalis (HSV-1 and HSV-2 [Whitley, R. J. 1996. Herpes Simplex Viruses, p. 2297–2342. In B. N. Fields, D. M. Knipe, and P. M. Howley (ed.), Fields Virology, 3rd ed. Lippincott-Raven Publishers, Philadelphia, Pa.]); chicken pox and shingles (VZV [Arvin, A. 1996. Varicella-Zoster Virus, p. 2547–2585. In B. N. Fields, D. M. Knipe, and P. M. Howley (ed.), Fields Virology, 3rd ed. Lippincott-Raven Publishers, Philadelphia, Pa.]); infectious mononucleosis (EBV [Rickinson, A. B. and Kieff, E. 1996. Epstein-Barr Virus, p. 2397–2446. In B. N. Fields, D. M. Knipe, and P. M. Howley (ed.), Fields Virology, 3rd ed. Lippincott-Raven Publishers, Philadelphia, Pa.]); pneumonia and retinitis (HCMV [(Britt, W. J., and Alford, C. A. 1996. Cytomegalovirus, p. 2493–2523. In B. N. Fields, D. M. Knipe, and P. M. Howley (ed.), Fields Virology, 3rd ed. Lippincott-Raven Publishers, Philadelphia, Pa.]); exanthem subitum (HHV-6 [(Pellet, P. E, and Black, J. B. 1996. Human Herpesvirus 6, p. 2587–2608. In B. N. Fields, D. M. Knipe, and P. M. Howley (ed.), Fields Virology, 3rd ed. Lippincott-Raven Publishers, Philadelphia, Pa.] and HHV-7 [Frenkel, N., and Roffman, E. 1996. Human Herpesvirus 7, p. 2609–2622. In B. N. Fields, D. M. Knipe, and P. M. Howley (ed.), Fields Virology, 3rd ed. Lippincott-Raven Publishers, Philadelphia, Pa.]); and Kaposi's sarcoma (HHV-8 [Neipel, F., Albrecht, J. C., and Fleckenstein, B. 1997. Cell-homologous genes in the Kaposi's sarcoma-associated rhadinovirus human herpesvirus 8: determinants of its pathogenicity? J. Virol. 71:4187–92, 1997]). HCMV is considered in more detail below. Following the primary infection, herpesviruses establish latency within the infected individual and remain there for the remainder of his/her life. Periodic reactivation of latent virus is clinically relevant. In the case of HSV, reactivated virus can be transmitted to infants during birth, causing either skin or eye infection, central nervous system infection, or disseminated infection (i.e. multiple organs or systems). Shingles is the clinical manifestation of VZV reactivation. Treatment of HSV and VZV is generally with antiviral drugs such as acyclovir (Glaxo Wellcome), ganciclovir (Roche) and foscarnet (Asta) which target viral encoded DNA polymerase.

HCMV is a ubiquitous opportunistic pathogen infecting 50–90% of the adult population (Britt, W. J., and Alford, C. A. 1996. Cytomegalovirus, p. 2493–2523. In B. N. Fields, D. M. Knipe, and P. M. Howley (ed.), Fields Virology, 3rd ed. Lippincott-Raven Publishers, Philadelphia, Pa.). Primary infection with HCMV is usually asymptomatic, although heterophile negative mononucleosis has been observed. The virus is horizontally transmitted by sexual contact, breast milk, and saliva. Intrauterine transmission of HCMV from the pregnant mother to the fetus occurs and is often the cause of serious clinical consequences. HCMV remains in a latent state within the infected person for the remainder of his/her life. Cell-mediated immunity plays a central role in controlling reactivation from latency. Impaired cellular immunity leads to reactivation of latent HCMV in seropositive persons.

HCMV disease is associated with deficient or immature cellular immunity. There are 3 major categories of persons with HCMV disease (reviewed by Britt and Alford, 1996). (1) In immunocompromised (AIDS) patients, HCMV is one of the two most common pathogens causing clinical disease (the other is Pneumocystis). The most common manifestation of HCMV in AIDS is retinitis, although infection of other organs including the adrenal glands, lungs, GI tract, and central nervous system are also reported frequently. 90% of AIDs patients have active HCMV infection; 25–40% (~85,000 patients in the United States) have life- or sight-threatening HCMV disease. HCMV is the cause of death in 10% of persons with AIDs. (2) Due to immune system suppression to reduce the risk of graft rejection, HCMV reactivation or reinfection is common amongst kidney, liver, heart, and allogeneic bone marrow transplant patients. Pneumonia is the most common HCMV disease in these patients, occurring in up to 70% of these transplant patients. (3) Congenital infection due to HCMV occurs in 1% of all births, about 40K per year. Up to 25% of these infants are symptomatic for HCMV disease between ages 0–3 years. HCMV disease is progressive, causing mental retardation and neurological abnormalities, in children. Recent studies suggest that treatment with anti-HCMV drugs may reduce morbidity in these children.

Several antiviral drugs are currently being marketed (Bron, D., R. Snoeck, and L. Lagneaux. 1996. New insights into the pathogenesis and treatment of cytomegalovirus. Exp. Opin. Invest. Drugs 5:337–344; Crumpacker, C. 1996. Ganciclovir. New Eng. J. Med. 335:721–729; Sachs, S., and F. Alrabiah. 1996. Novel herpes treatments: a review. Exp. Opin. Invest. Drugs 5:169–183). These include: ganciclovir (Roche), a nucleoside analog with hemopoietic cell toxicity; foscarnet (Astra), a pyrophosphate analog with nephrotoxicity; and cidofovir, Gilead), a nucleoside phosphonate with acute nephrotoxicity. Each of these drugs target the viral-encoded DNA polymerase, are typically administered intravenously due to their low bioavailability, and, as noted above, are the source of significant toxicity. Ganciclovir-resistant mutants which arise clinically are often cross-resistant with cidofovir. Hence, there is a need for safer (i.e. less toxic), orally bioavailable anti-viral drugs which are directed against novel viral targets.

Phenyl thioureas are disclosed for use in a variety of pharmaceutical applications. Armistead, et al., WO 97/40028, teaches phenyl ureas and thioureas as inhibitors of the inosine monophosphate dehydrogenase (IMPDH) enzyme which is taught to play a role in viral replication diseases such herpes.

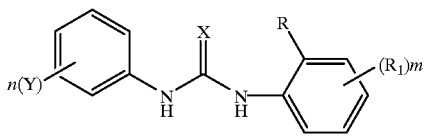

Widdowson, et al., WO 96/25157, teaches phenyl urea and thiourea compounds of the below formula for treating diseases mediated by the chemokine, interleukin-8.

Morin, Jr., et al., U.S. Pat. No. 5,593,993 teaches certain phenyl thiourea compounds for treatment of AIDs and the inhibition of the replication of HIV and related viruses.

Therefore, it is an object of this invention to provide compounds, and pharmaceutically acceptable salts thereof, to inhibit and/or treat diseases associated with herpes viruses including human cytomegalovirus, herpes simplex viruses, Epstein-Barr virus, varicella-zoster virus, human herpesviruses-6 and -7, and Kaposi herpesvirus.

DESCRIPTION OF THE INVENTION

In accordance with the present invention are provided compounds having the formula:

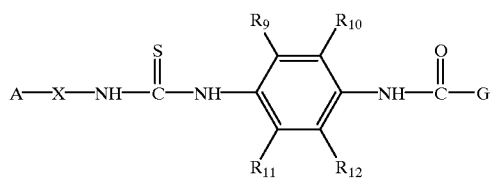

wherein

A is heteroaryl;

$R_9$–$R_{12}$ are independently hydrogen, alkyl of 1 to 4 carbon atoms, perhaloalkyl of 1 to 4 carbon atoms, halogen, alkoxy of 1 to 4 carbon atoms, or cyano, or $R_9$ and $R_{10}$ or $R_{11}$ and $R_{12}$ may be taken together to form aryl of 5 to 7 carbon atoms;

W is O, $NR_6$, or is absent;

G is aryl or heteroaryl;

X is a bond, —NH, alkyl of 1 to 6 carbon atoms, alkenyl of 1 to 6 carbon atoms, alkoxy of 1 to 6 carbon atoms, thioalkyl of 1 to 6 carbon atoms, alkylamino of 1 to 6 carbon atoms, or (CH)J; and J is alkyl of 1 to 6 carbon atoms, cycloalkyl of 3 to 7 carbon atoms, phenyl or benzyl; and n is an integer from 1 to 6; or a pharmaceutically acceptable salt thereof.

In some preferred embodiments of the present invention A is a 5 or 10 membered mono or bicyclic heteroaryl having 1 or 2 heteroatoms. More preferably, A is pyridyl, furyl, imidazolyl, pyrrolyl, thienyl, or indanyl. Still more preferably, A is 3-pyridyl.

In some preferred embodiments of the present invention A is substituted with one or more substitutents selected from alkyl of 1 to 6 carbon atoms, alkenyl of 2 to 6 carbon atoms, alkynyl of 2 to 6 carbon atoms, perhaloalkyl of 1 to 6 carbon atoms, cycloalkyl of 3 to 10 carbon atoms, heterocycloalkyl of 3 to 10 carbon members, aryl, heteroaryl, halogen, —CN, —$NO_2$, —$CO_2R_6$, —$COR_6$, —$OR_6$, —$SR_6$, —$SOR_6$, —$SO_2R_6$, —$CONR_7R_8$, —$NR_6N(R_7R_8)$, —$N(R_7R_8)$ or W—Y—$(CH_2)_n$—Z wherein $R_6$ and $R_7$ are independently hydrogen, alkyl of 1 to 6 carbon atoms, perhaloalkyl of 1 to 6 carbon atoms, or aryl; $R_8$ is hydrogen, alkyl of 1 to 6 carbon atoms, perhaloalkyl of 1 to 6 carbon atoms, cycloalkyl of 3 to 10 carbon atoms, heterocycloalkyl of 3 to 10 members, aryl or heteroaryl, or $R_7$ and $R_8$, taken together may form a 3 to 7 membered heterocycloalkyl;

W is O, $NR_6$, or is absent;

Y is —(CO)— or —($CO_2$)—, or is absent;

Z is alkyl of 1 to 4 carbon atoms, —CN, —$CO_2R_6$, $COR_6$, —$CONR_7R_8$, —$OCOR_6$, —$NR_6COR_7$, —$OCONR_6$, —$OR_6$, —$SR_6$, —$SOR_6$, —$SO_2R_6$, $SR_6N(R_7R_8)$, —$N(R_7R_8)$ or phenyl; and n is 1 to 6.

In still more preferred embodiments A is substituted with one or more substitutents selected from halogen or alkyl of 1–6 carbon atoms.

In some embodiments of the present invention, at least 1 of $R_9$–$R_{12}$ is not hydrogen. Preferably when one of $R_9$–$R_{12}$ is not hydrogen, one or more of $R_9$–$R_{12}$ are selected from halogen, methyl, methoxy, and cyano. More preferably each of $R_9$–$R_{12}$ is hydrogen.

G is preferably a 5 or 6 membered heteroaryl having 1 or 2 heteroatoms. More preferably, G is furyl or thiadiazole and in still more preferred embodiments, G is 1,2,3 thiadiazolyl or 2-furyl. Alternatively, G may be alkyl of 1 to 6 carbon atoms which optionally may be substituted, preferably by a halogen.

X is preferably a bond or straight chain lower alkyl group. When X is a lower alkyl group it is preferred that X is methyl or ethyl.

Preferred compounds of the present invention are the following compounds which include pharmaceutically acceptable salts thereof.

Furan-2-carboxylic acid [4-(3-pyridin-2-yl-thioureido)-phenyl]-amide;

Furan-2-carboxylic acid [4-(3-pyridin-4-yl-thioureido)-phenyl]-amide;

Furan-2-carboxylic acid [4-(3-pyridin-3-yl-thioureido)-phenyl]-amide;

[1,2,3]Thiadiazole-4-carboxylic acid {4-[3-(6-chloro-pyridin-3-yl)-thioureido]-phenyl}-amide;

Furan-2-carboxylic acid [4-(3-pyrimidin-4-yl-thioureido)-phenyl]-amide;

[1,2,3]Thiadiazole-4-carboxylic acid {4-[3-(5-chloro-pyridin-3-yl)-thioureido]-phenyl}-amide;

[1,2,3]Thiadiazole-4-carboxylic acid {4-[3-(5-bromo-pyridin-3-yl)-thioureido]-phenyl}-amide;

[1,2,3]Thiadiazole-4-carboxylic acid {4-[3-(1-tert-butyl-1H-imidazol-2-yl)-thioureido]-phenyl}-amide;

Furan-2-carboxylic acid {4-[3-(1-tert-butyl- 1H-imidazol-2-yl)-thioureido]-phenyl}-amide;

[1,2,3]Thiadiazole-4-carboxylic acid {4-[3-(5-trifluoromethyl-pyridin-3-yl)-thioureido]-phenyl}-amide;

Furan-2-carboxylic acid [4-(3-pyridin-3-ylmethyl-thioureido)-phenyl]-amide;

[1,2,3]Thiadiazole-4-carboxylic acid [4-(3-pyridin-3-ylmethyl-thioureido)-phenyl]-amide;

[1,2,3]Thiadiazole-4-carboxylic acid [4-(3-indan-1-yl-thioureido)-phenyl]-amide;

Furan-2-carboxylic acid [4-(3-pyridin-4-ylmethyl-thioureido)-phenyl]-amide;

[1,2,3]Thiadiazole-4-carboxylic acid [4-(3-pyridin-4-ylmethyl-thioureido)-phenyl]-amide;

2-Fluoro-N-[4-(3-pyridin-3-yl-thioureido)-phenyl]-benzamide;

2-Fluoro-N-[4-(3-pyridin-2-yl-thioureido)-phenyl]-benzamide;

2-Fluoro-N-[4-(3-pyridin-4-yl-thioureido)-phenyl]-benzamide;
2-Fluoro-N-[4-(3-pyridin-3-ylmethyl-thioureido)-phenyl]-benzamide;
2-Fluoro-N-{4-[3-(1H-indazol-5-yl)-thioureido]-phenyl}-benzamide;
N-{4-[3-(1-tert-Butyl-1H-imidazol-2-yl)-thioureido]-phenyl}-2-fluoro-benzamide;
2-Fluoro-N-[4-(3-pyridin-4-ylmethyl-thioureido)-phenyl]-benzamide;
2-Fluoro-N-{4-[3-(1-furan-2-yl-ethyl)-thioureido]-phenyl}-benzamide;
2-Fluoro-N-{4-[3-(1-pyridin-4-yl-ethyl)-thioureido]-phenyl}-benzamide;
2-Fluoro-N-(4-{3-[1-(1-methyl-1H-pyrrol-2-yl)-ethyl]-thioureido}-phenyl)-benzamide; and
2-Fluoro-N-{4-[3-(1-thiophen-3-yl-ethyl)-thioureido]-phenyl}-benzamide.

Alkyl as used herein refers to straight or branched chain lower alkyl of 1 to 6 carbon atoms. Exemplary alkyl groups include methyl, ethyl, propyl, isopropyl, butyl, isobutyl, t-butyl, pentyl and hexyl.

Alkenyl as used herein refers to straight or branched chain lower alkyl of 2 to 6 carbon atoms containing at least one carbon-carbon double bond. Alkenyl includes vinyl groups.

Alkynyl as used herein refers to straight or branched chain lower alkyl of 2 to 6 carbon atoms containing at least one carbon-carbon triple bond.

Alkyl, alkenyl and alkynyl groups of the present invention may be substituted or unsubstituted.

Cycloalkyl refers to a saturated mono or bicyclic ring system of 3 to 10 carbon atoms. Exemplary cycloalkyl groups include cyclopentyl, cyclohexyl and cycloheptyl. Cycloalkyl groups of the present invention may be substituted or unsubstituted.

Heterocycloalkyl refers to a saturated mono or bicyclic ring system of 3 to 10 members having 1 to 3 heteroatoms selected from N, S and 0, including, but not limited to aziridinyl, azetidinyl, imidazolidinyl, morpholinyl, thiomorpholinyl, piperazinyl, pyrazolidinyl, piperidinyl, and pyrrolidinyl. Heterocycloalkyl groups of the present invention may be substituted or unsubstituted.

Aryl, as used herein refers to an aromatic mono or bicyclic ring of 5 to 10 carbon atoms. Exemplary aryl groups include phenyl, naphthyl, and biphenyl. Aryl groups of the present invention may be substituted or unsubstituted.

Heteroaryl as used herein refers to an aromatic mono or bicyclic ring of 5 to 10 members having 1 to 3 heteroatoms selected from N, S or O including, but not limited to thiazolyl, thiadiazolyl, oxazolyl, furyl, indolyl, benzothiazolyl, benzotriazolyl, benzodioxyl, indazolyl, and benzofuryl. Preferred heteroaryls include quinolyl, isoquinolyl, napthalenyl, benzofuranyl, benzothienyl, indolyl, pyridyl, pyrazinyl, thienyl, furyl, pyrrolyl, isoxazolyl, oxazolyl, isothiazolyl, thiazolyl, pyrazolyl, triazolyl, thiadiazolyl, and imidazolyl. Heteroaryl groups of the present invention may be substituted or unsubstituted.

Perhaloalkyl refers to an alkyl group of 1 to 6 carbon atoms in which three or more hydrogens are substituted with halogen.

Phenyl as used herein refers to a 6 membered aromatic ring.

Halogen, as used herein refers to chlorine, bromine, iodine and fluorine.

Unless otherwise limited substitutents are unsubstituted and may include alkyl of 1 to 6 carbon atoms, cycloalkyl of 1 to 6 carbon atoms, heterocycloalkyl of 1 to 6 members, perhaloalkyl of 1 to 6 carbon atoms, alkylamino, dialkylamino, aryl or heteroaryl.

Carbon number refers to the number of carbons in the carbon backbone and does not include carbon atoms occurring in substituents such as an alkyl or alkoxy substituents.

Where terms are used in combination, the definition for each individual part of the combination applies unless defined otherwise. For instance, alkylcycloalkyl is an alkyl-cycloalkyl group in which alkyl and cycloalkyl are as previously described.

Pharmaceutically acceptable salts are the acid addition salts which can be formed from a compound of the above general formula and a pharmaceutically acceptable acid such as phosphoric, sulfuric, hydrochloric; hydrobromic, citric, maleic, succinic, fumaric, acetic, lactic, nitric, sulfonic, p-toluene sulfonic, methane sulfonic acid, and the like.

The compounds of this invention contain a chiral center, providing for various seteroisomeric forms of the compounds such as racemic mixtures as well as the individual optical isomers. In some preferred embodiments of the present invention the compounds of the present invention are substantially pure optical isomers. By substantially pure is meant the composition contains greater than 75% of the desired isomer and may include no more than 25% of the undesired isomer. In more preferred embodiments the pure optical isomer is greater than 90% of the desired isomer. In some preferred embodiments, when the target is VZV, the (S) isomer is preferred. The individual isomers can be prepared directly or by asymmetric or stereospecific synthesis or by conventional separation of optical isomers from the racemic mixture.

Compounds of the present invention may be prepared by those skilled in the art of organic synthesis employing methods described below which utilize readily available reagents and starting materials unless otherwise described. Compounds of the present invention are thus prepared in accordance with the following schemes.

The novel compounds of the present invention are prepared according to the following reaction schemes. Similarly, reaction of appropriately substituted isothiocyanates 4, wherein the substitutents of A, and X are described as above with appropriately substituted anilines 5, wherein the substituents $R_9$–$R_{12}$ and G are described above, in a convenient solvent such as those listed above affords the desired thioureas 1.

Methods 31 and 34

Alternatively, appropriately substituted thioureas 1 can be prepared as described by Methods 32 and 33 by reacting amines 2 and 5 in the presence of either one molar equivalent of 1,1'-thiocarbonyl diimidazole in an appropriate solvent such as dichloro-methane and tetrahydrofuran or mixtures thereof or one molar equivalent of 1,1'-thiocarbonyl-di-(1,2,4)-triazole in an appropriate solvent such as dichloromethane and tetrahydrofuran or mixtures thereof at room temperature.

In certain instances, subsequent chemical modification of the final thioureas 1 was required. These methods, Methods 35–39, are summarized below.

Thioureas 1 wherein A comprises at least one substituent which is 1-hydroxyethoxy or carboxy-methoxy, $R_9$–$R_{12}$ and G are defined as above and X equals a bond, may be prepared from the corresponding alkyl esters by alkaline hydrolysis with aqueous sodium or potassium hydroxide in a suitable solvent such as methanol, tetrahydrofuran or mixtures thereof at room temperature in accordance with Methods 35 and 36.

Thioureas 1 wherein A comprisese at least one substituent which is 1 -acyloxyethoxy or methansulfonoxyethoxy, $R_9$–$R_{12}$ and G are defined as above and X equals a bond, may be prepared from the corresponding 1-hydroxyethoxy derivative by acylation with appropriate acylating agents such as benzoic acid chloride or methanesulfonic acid chloride in the presence of a suitable tertiary amine base such as triethylamine or diisopropylethylamine in a suitable solvent such as dichloromethane or the like at room temperature in accordance with Methods 37 and 38.

Thioureas 1 wherein A comprises at least one substituent which is 1-aminoethoxy, $R_9$–$R_{12}$ and G are defined as above and X equals a bond, may be prepared from the corresponding 1-methanesulfonoxy-ethoxy derivative by reaction with an appropriate secondary amine such as dimethylamine in a suitable solvent mixture such as tetrahydrofuran and water or the like at room temperature in accordance with Method 39.

Thioureas 1 wherein A comprises at least one substituent which is 1-aminoalkyl, $R_9$–$R_{12}$ and G are defined as above and X equals a bond, may be prepared from the corresponding 1-azidoalkyl derivative by reaction with stannous chloride in a suitable solvent such as methanol, ethanol or the like at room temperature in accordance with Method 40.

The intermediate isothiocyanates 3 and 4 shown above in Methods 31 and 34 are prepared in accordance with Method 41 (below) essentially according to the procedures of Staab, H. A. and Walther, G. *Justus Liebigs Ann. Chem.* 657, 104 (1962)) by reacting appropriately substituted amines 5 or 2, respectively, X is defined above with one molar equivalent of 1,1′-thiocarbonyldiimidazole in an appropriate solvent such as dichloromethane and tetrahydrofuran or mixtures thereof.

Method 41

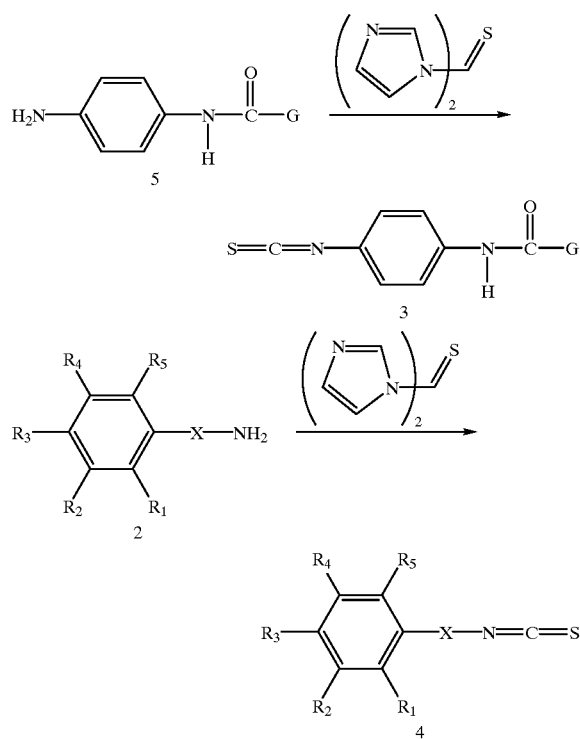

The intermediates 2 and 5 may be prepared according to the following protocols:

According to Methods 1A–1G, amines 2, wherein A is defined above and X is defined above and amines 5, wherein $R_9$–$R_{12}$ are defined above, may be prepared by reduction of the appropriately substituted nitrobenzenes and corresponding heteroaryls according to a variety of procedures known to those skilled in the art and described in R. J. Lindsay, *Comprehensive Organic Chemistry* (ed. Sutherland), Volume 2, Chapter 6.3.1, Aromatic Amines, 1979. Such procedures include the reduction of nitrobenzenes to form anilines upon exposure to:

a) iron powder and a strong acid, such as hydrochloric acid (Methods 1A) either neat or in alcohol solvent such as methanol or ethanol, at temperatures ranging from room temperature to the refluxing temperature of the solvent, or;

b) iron powder and glacial acetic acid (Method 1B), either neat or in alcohol solvent such as methanol or ethanol, at temperatures ranging from room temperature to the refluxing temperature of the solvent, or;

c) iron powder and aqueous ammonium chloride (Method 1C), either neat or in alcohol solvent such as methanol or ethanol, at temperatures ranging from room temperature to the refluxing temperature of the solvent, or;

d) tin and a strong mineral acid, such as hydrochloric acid (Method 1D), either neat or in alcohol solvent such as methanol or ethanol, at temperatures ranging from room temperature to the refluxing temperature of the solvent, or;

e) when substitutents of A and $R_9$–$R_{12}$ are selected from Cl, Br, I, —($OSO_2$)—$CF_3$, or —($OSO_2$)-1-(4-methylphenyl), by catalytic reduction such as with hydrogen and palladium on carbon (Method 1E) in an appropriate solvent such as methanol, ethanol, or ethyl acetate, under one or more atmospheres of pressure or;

f) when substituents of A and $R_9$–$R_{12}$ are selected from Cl, Br, I, —($OSO_2$)—$CF_3$, or —($OSO_2$)-1-(4-methylphenyl), by catalytic reduction such as with cyclohexene and palladium on carbon (Method 1F) in an appropriate solvent such as methanol or ethanol, at temperatures ranging from room temperature to the refluxing temperature of the solvent, or;

g) aqueous sodium hydrosulfite in alcohol solvent at temperatures ranging from room temperature to the refluxing temperature of the solvent (Method 1G).

Alternatively, according to Methods 3A–3C, amines 2, wherein A is defined above and X is defined above and anilines 5, wherein $R_9$–$R_{12}$ are defined above, may be prepared by the cleavage of the aniline nitrogen-carbon bond of amide and carbamate derivatives of these anilines according to a variety of procedures known to those skilled in the art and described in Greene, *Protective Groups in Organic Synthesis* volume 2, Chapter 7, 1991, and references therein. Such procedures include:

a) the exposure of appropriately substituted arylamino-tert-butyl-carbamates to a strong acid such as trifluoroacetic acid (Method 3A) either neat or in an appropriate solvent such as dichloromethane at temperatures between 0° C. and room temperature, or;

b) the exposure of appropriately substituted arylamino-(2-trimethylsilylethyl)-carbamates to a fluoride ion source such as tetrabutylammonium fluoride or potassium fluoride (Method 3B) in aqueous acetonitrile or tetrahydrofuran or mixtures thereof at temperatures ranging from room temperature to the reflux temperature of the solvent, or;

c) the exposure of appropriately substituted arylamino-trifluoroacetamides to a strong base such as sodium or potassium hydroxide or sodium or potassium carbonate in an alcohol solvent such as methanol or ethanol (Method 3C) at temperatures ranging from room temperature to the reflux temperature of the solvent.

Alternatively, according to Method 11, amines 2, wherein A is defined above, and X equals a bond and at least one substituent of A is vinyl, may be prepared by the palladium catalyzed coupling of a vinyl trialkyltin reagent, such as tributylvinyltin, with an appropriately substituted bromo- or iodo-aniline, for example 3-chloro-4-iodo-aniline, employing a palladium catalyst, such as tris(dibenzylidineacetone)-bipalladium, and a ligand, such as triphenylarsine, in a suitable solvent such as tetrahydrofuran or N-methylpyrrolidinone, at temperatures ranging from room temperature to the reflux temperature of the solvent, essentially according to the procedures of V. Farina and G. P. Roth in *Advances in Metal-Organic Chemistry*, Vol. 5, 1–53, 1996 and references therein.

Alternatively, according to Method 42, amines 2, wherein A is defined above and X is defined above and at least one substituent of A is defined as dialkylamino, may be prepared by the palladium catalyzed amination of an appropriately substituted 3- or 5-bromo- or iodo-aniline, by secondary amines under conditions which employ a palladium catalyst, such as bis(dibenzylidineacetone)palladium, and a ligand, such as tri-o-tolylphosphine, and at least two molar equivalents of a strong base, such as lithium bis-(trimethylsilyl) amide in a sealed tube, in a suitable solvent such as tetrahydrofuran or toluene, at temperatures ranging from room temperature to 100 ° C., essentially according to the procedures of J. F. Hartwig and J. Louie *Tetrahedron Letters* 36 (21), 3609 (1995).

Alternatively, according to Method 43, amines 2, wherein A is defined above and X is defined above and at least one substituent of A is defined as alkyl, may be prepared by the palladium catalyzed alkylation of an appropriately substituted 3- or 5-bromo-or iodo-aniline, by alkenes under condiditons which employ a palladium catalyst such as [1,1'-bis(diphenylphosphino)ferrocene]palladium(II) chloride-dichloromethane complex and in the presence of 9-borabicyclo[3.3.1] nonane and a suitable base such as aqueous sodium hydroxide in a suitable solvent such as tetrahydrofuran or the like at temperatures ranging from room temperature to the reflux temperature of the solvent.

The acyl and carbamoyl amine derivatives utilized as starting materials in Methods 3A–3C may be prepared by the derivatization of the corresponding amines as described in Methods 2A–2G according to a variety of procedures known to those skilled in the art and described in Greene, *Protective Groups in Organic Synthesis* volume 2, Chapter 7, 1991, and references therein. Such procedures include:

a) the reaction of an appropriately substituted amine with di-tert-butyl-dicarbonate (Method 2A) in the presence or absence of one or more molar equivalents of a tertiary amine such as triethylamine or N,N-diisopropylethylamine in a suitable solvent such as acetone, tetrahydrofuran, dimethylformamide, dichloromethane, and the like, at temperatures ranging from room temperature to the reflux temperature of the solvent to produce the corresponding arylamino-tert-butyl-carbamate, or;

b) the reaction of an appropriately substituted aniline with 1-[2-(trimethylsilyl)ethoxycarbonyl-oxy]benzotriazole (Method 2B) in the presence of a tertiary amine such as triethylamine or diisopropylethylamine in a suitable solvent such as dimethylformamide at room temperature to produce the corresponding heteroarylamino-(2-trimethylsilylethyl)-carbamate, or;

c) the reaction of an appropriately substituted aniline with a carboxylic acid chloride or acid anhydride (Method 2C) either neat or in an appropriate solvent such as tetrahydrofuran, dimethylformamide, dichloromethane, pyridine and the like, in the presence of one or more molar equivalents of a teriary amine base such as triethylamine or N,N-diisopropylethyl-amine to produce the corresponding arylaminoamide, or;

d) the reaction of an apptopriately substituted nitro aniline with a carboxylic acid chloride (Method 2D) in the absence of one or more molar equivalents of a teriary amine base such as triethylamine or N,N-diisopropylethylamine either neat or in an appropriate solvent such as tetrahydrofuran, 1,4-dioxane and the like at temperatures ranging from room temperature to the reflux temperature of the solvent to produce the corresponding nitro arylaminoamide, or;

e) the reaction of an appropriately substituted aniline with a carboxylic acid (Method 2E) in the presence of a coupling agent such as benzotriazole-1-yloxy-tris-(dimethylamino)-phosphonium hexafluorophosphate, 2-(1H-benzotriazole-1-yloxy)-1,1,3,3-tetramethyluronium hexafluorophosphate, dicyclohexyl carbodiimide and the like and in the presence of a tertiary amine such as triethylamine or diisopropylethylamine in a suitable solvent such as diichloromethane, dimethylformamide and the like, at room temperature to produce the corresponding arylaminoamide, or;

f) the reaction of an appropriately protected aniline such as an heteroarylamino-tert-butyl-carbamate or the like in which at least one substituent of A and $R_1$–$R_{12}$ is defined as —W—Y—$(CH_2)_n$—Z wherein W, Y, and Z are defined as above, with a carboxylic acid anhydride (Method 2F) in the presence of a suitable base such as pyridine in an appropriate such as dichloromethane, dimethylformamide or the like at temperatures ranging from 0° C. to room temperature to produce the corresponding carboxylic acid ester, or;

g) the reaction of an appropriately substituted aniline in which at least one substituent of A is defined as hydroxyl with di-tert-butyl-dicarbonate (Method 2G) in the absence of one or more molar equivalents of a tertiary amine such as triethylamine or N,N-diisopropylethylamine in a suitable solvent such as acetone, tetrahydrofuran, dimethylformamide, dichloromethane, and the like, at temperatures ranging from room temperature to the reflux temperature of the solvent to produce the corresponding heteroarylamino-tert-butyl-carbamate.

Nitrobenzene intermediates that are ultimately converted to amines 2 and 5 by methods shown above in Methods 1A–1G may be prepared in accordance with Methods 4A, 4C, 4E–4F.

Referring to Methods 4A, 4C, and 4E–4H, the nitrobenzene intermediates which are ultimately converted into amines 2, where A comprises substituent defined as alkoxy, thioalkoxy, alkylsulfenyl, alkylsulfinyl, and dialkylamino may be prepared by the nucleophilic displacement of appropriately substituted 2-, 4-, and/or 6-fluoro-, chloro-, bromo-, iodo-, trifluoromethylsulfonyl-, or (4-methylphenyl) sulfonyl-substituted nitrobenzenes or corresponding heteroaryls by methods which include the following:

a) reaction of alcohols with appropriately substituted 2- or 4-halo- or sulfonate esters of nitrobenzenes, benzonitriles or corresponding heteroaryls (Method 4A) either neat or in an appropriate solvent such as tetrahydrofuran, dioxane, acetonitrile, N,N-dimethylformamide or dimethylsulfoxide in the presence or absence of one or more molar equivalents of a base such as sodium carbonate, potassium carbonate, sodium hydroxide, potassium hydroxide, sodium hydride, potassium hydride, or the like, at temperatures ranging from room temperature to the reflux temperature of the solvent;

b) reactions of preformed sodium, lithium, or potassium phenoxides with appropriately substituted 2- or 4- halo- or sulfonate esters of nitrobenzenes, benzonitriles or corresponding heteroaryls (Method 4H) either neat or in an appropriate solvent such as tetrahydrofuran, dioxane, acetonitrile, N,N-dimethylformamide or dimethylsulfoxide, at temperatures ranging from room temperature to the reflux temperature of the solvent, or;

c) reaction of ammonia, primary or secondary amines with appropriately substituted 2- or 4-halo- or sulfonate esters of nitrobenzenes, benzonitriles or corresponding heteroaryls (Methods 4C,F) either neat or in an appropriate solvent such as tetrahydrofuran, dioxane, acetonitrile, N,N-dimethyl-formamide or dimethylsulfoxide, at temperatures ranging from room temperature to the reflux temperature of the solvent;

d) reaction of preformed sodium, lithium, or potassium salts of amines with appropriately substituted 2- or 4- halo- or sulfonate esters of nitrobenzenes or benzonitriles (Method 4G) in an appropriate solvent such as tetrahydrofuran at temperatures ranging from 0C to the reflux temperature of the solvent, or;

e) reaction of sodium sulfide with appropriately substituted 2- or 4- halo- or sulfonate esters of nitrobenzenes or benzonitriles either neat or in an appropriate solvent such as tetrahydro-furan, dioxane, acetonitrile, N,N-dimethylformamide or dimethylsulfoxide, at temperatures ranging from room temperature to the reflux temperature of the solvent, followed by the addition of an alkyl halide directly to the reaction mixture (Method 4E).

Alternatively, referring to Methods 5C and 6, the nitrobenzene intermediates and corresponding heteroaryls which are ultimately converted into amines 2, wherein at least one substituent of A is defined as alkoxy may be prepared from the corresponding substituted hydroxynitrobenzenes and corresponding heteroaryls by methods which include the following:

a) reaction of the hydroxy-nitrobenzene with an alkyl halide or dialkyl sulfonate ester (Method 5C) in the presence of a base, such as potassium carbonate, sodium carbonate, potassium hydroxide, sodium hydroxide, potassium hydride, or sodium hydride, in an appropriate solvent such as acetone, N,N-dimethylformamide, tetrahydrofuran or dimethylsulfoxide at temperatures ranging from room temperature to the reflux temperature of the solvent, or;

b) reaction of the hydroxy-nitrobenzene or corresponding heteroaryl with an alkyl alcohol, triphenylphosphine, and a dialkylazadicarboxylate reagent (Method 6), such as diethylazodicarboxylate, in an anhydrous aprotic solvent such as diethyl ether or tetrahydrofuran at temperatures ranging from 0° C. to the reflux temperature of the solvent, essentially according to methods described in *Mitsunobu, O,* Synthesis 1981, 1 and references therein.

In addition, referring to Method 5A and 5E, the carbamoyl amine derivatives utilized as starting materials in Methods 3A-3C which are ultimately converted into amines 2, wherein at least one substituent of A is defined as alkoxy may be prepared the corresponding substituted hydroxy aryl- or heteroarylamino-tert-butyl-carbamate by reaction with alkyl halides, trifluormethane-sulfonates, 4-methylbenzenesulfonates, dialkylsulfonate, ethylene carbonate and the like in the presence of a suitable base such as potassium carbonate in an appropriate solvent such as acetone, toluene, or N,N-dimethyl-formamide at temperatures ranging from room temperature to the reflux temperature of the solvent.

Alternatively, referring to Methods 7A–G, the nitrobenzene and corresponding heteroaryls which are ultimately converted into amines 2, comprising at least one alkoxy at least one halogen, and X equals a bond, may be prepared by standard halogenation reactions which include the following:

a) reaction of a 2- or 4- hydroxy-nitrobenzene or corresponding heteroaryl with aqueous sodium hypochlorite (Methods 7A and 7B), at room temperature or;

b) reaction of a 2-hydroxy-4-methoxy or 2,4-dimethoxynitrobenzene or corresponding heteroaryl (Method 7C and 7D) with bromine in suitable solvent such as chloroform, dichlormethane, glacial acetic acid or the like in the presence or the absence of silver trifluoroacetate at room temperature, or;

c) reaction of a 2,4-dimethoxynitrobenzene or corresponding heteroaryl (Method 7E) with benzyltrimethylammonium dichloroiodate in the presence of anhydrous zinc chloride in a suitable solvent such as glacial acetic acid, at room temperature or;

d) reaction of a 2-hydroxy-4-methoxynitrobenzene or corresponding heteroaryl (Method 7F) with benzyltrimethyl-ammonium dichloroiodate in the presence of sodium bicarbonate in a suitable solvent mixture such as dichloromethane and methanol, at room temperature or;

e) reaction of a 2,4-dimethoxynitrobenzene or corresponding heteroaryl (Method 7G) with 3,5-dichloro-1-fluoropyridine triflate in a suitable solvent such as tetrachloroethane, at a temperature ranging from room temperature to the reflux temperature of the solvent.

Referring to Method 8, the nitrobenzene intermediates or corresponding heteroaryl which are ultimately converted into amines 2, wherein A is substituted by $CF_3$ and X equals a bond may be prepared from the corresponding substituted 4-iodo-nitrobenzenes or corresponding heteroaryl by reaction with trimethyl(trifluoromethyl)silane in the presence of cuprous iodide and potassium fluoride in a suitable solvent such as N,N-dimethyl-formamide or the like at a temperature ranging from room temperature to the reflux temperature of the solvent in a sealed reaction vessel.

Referring to Methods 19A and 19B, the nitrobenzene intermediates which are ultimately converted into amines 2, wherein A comprises a substituent defined as —$HNCOCH_2NR_7R_8$ or —$HNCOCH_2SR_6$, and X equals a bond may be prepared from the corresponding substituted 4-(N-chloroacetyl)-nitroaniline by reaction with either a suitable secondary amine such as dimethylamine, morpholine or the like in a suitable solvent such as tetrahydrofuran and/or water mixtures at temperatures ranging from room temperature to the reflux temperature of the solvent or by reaction with an appropriate thiol in the presence of a suitable base such as sodium or potassium carbonate or the like in a suitable solvent such as tetrahydrofuran, 1,4-dioxane or the like at temperatures ranging from room temperature to the reflux temperature of the solvent.

Referring to Method 25, the nitrobenzene intermediates or corresponding heteroaryl which are ultimately converted into amines 2, wherein at least one substituent of A is defined as triflate and X equals a bond may be prepared from the corresponding phenol by reaction with trifluoromethane sulfonic anhydride in the presence of a tertiary amines such as triethylamine or diisopropyl-ethylamine or the like in a suitable solvent such as dichloromethane at temperatures ranging from 0° C. to room temperature.

Referring to Methods 9, 9B, and 10, the carbamoyl amine derivatives utilized as starting materials in Methods 3A–3C which are ultimately converted into amines 2, wherein at least one substituent A is defined as either alkylsulfenyl or alkylsulfinyl, may be prepared by reaction of the appropriate 4-alkylthio acylarylamino or acylheteroarylamino or carbamoylarylamino or carbamoylheteroarylamino derivative with an appropriate oxidizing agent such as dimethyloxirane or sodium periodate in a suitable solvent mixture such as acetone and dichloromethane or water at room temperature.

Referring to Method 12, the carbamoyl amine derivatives utilized as starting materials in Methods 3A–3C which are ultimately converted into amines 2, wherein a substituent of A is defined as 1-hydroxyethyl and X equals a bond may be prepared by reacting the corresponding 4-vinyl carbamoyl aniline with sodium borohydride in the presence of mercuric acetate in a suitable solvent such as tetrahydrofuran, 1,4-dioxane or the like and water at room temperature.

Referring to Method 13, the carbamoyl amine derivatives utilized as starting materials in Methods 3A–3C which are ultimately converted into amines 2, wherein a substituent of A is defined as 2-hydroxyethyl and X equals a bond, may be prepared by reacting the corresponding 4-vinyl carbamoyl aniline with sodium borohydride in the presence of glacial acetic acid in a suitable solvent such as tetrahydrofuran, 1,4-dioxane or the like at temperatures ranging from 0° C. to room temperature.

Referring to Method 14, the carbamoyl amine derivatives utilized as starting materials in Methods 3A–3C which are ultimately converted into amines 2, wherein a substituent of A is defined as 1-azidoethyl and and X is defined above, may be prepared by reacting the corresponding 4-(1-hydroxyethyl) carbamoyl aniline with hydrazoic acid in the presence of a dialkylazodicarboxylate such as diethylazodicarboxylate and triphenylphosphine in a suitable solvent mixture such as tetrahydrofuran and dichloromethane at temperatures ranging from 0° C. to room temperature.

Referring to Method 15, the carbamoyl amine derivatives utilized as starting materials in Methods 3A–3C which are ultimately converted into amines 2, wherein a substituent of A is defined as 3-dimethylaminoprop-1-ynyl and X is defined above, may be prepared by reacting the corresponding 4-iodocarbamoyl aniline with 1-dimethylamino-2-propyne in a suitable tertiary amine solvent such as triethylamine or diisopropylethylamine in the presence of bis(triphenylphosphine)palladium(II) chloride and cuprous iodide at temperatures ranging from room temperature to the reflux temperature of the solvent.

Referring to Method 16, the carbamoyl amine derivatives utilized as starting materials in Methods 3A–3C which are ultimately converted into amines 2, wherein a substituent of A is defined as 3-dimethylaminoacryloyl and X equals a bond, may be prepared by reacting the corresponding 4-(3-dimethylaminoprop-1-ynyl)carbamoyl aniline with a suitable peracid such as 3-chloroperoxybenzoic acid in a suitable solvent mixture such as dichloromethane and methanol at temperatures ranging from 0° C. to room temperature.

Referring to Methods 17 and 18, the carbamoyl amine derivatives utilized as starting materials in Methods 3A–3C which are ultimately converted into amines 2, wherein a substituent of A is defined as either 4-isoxazol-5-yl or 4-(1H-pyrazol-3-yl) and X equals a bond, may be prepared by reacting the corresponding 4-(3-dimethylamino-acryloyl) carbamoyl aniline with either hydroxylamine hydrochloride or hydrazine hydrate in a suitable solvent such as 1,4-dioxane or ethanol and the like at room temperature.

Referring to Method 20, the carbamoyl amine derivatives utilized as starting materials in Methods 3A–3C which are ultimately converted into amines 2, wherein a substituent of A is defined as —HNCO$_2$Z, Z is defined above and X equals a bond, may be prepared by reacting the corresponding 4-aminocarbamoyl aniline with 1,1-carbonyl-di-(1,2,4)-triazole and an appropriately substituted alcohol in a suitable solvent mixture such as tetrahydrofuran and dichloromethane and the like at temperatures ranging from room temperature to the reflux temperature of the solvent.

Referring to Methods 26 and 30, the carbamoyl amine derivatives utilized as starting materials in Methods 3A–3C which are ultimately converted into amines 2, wherein at least one substituent of A is defined as dialkylamino and X is defined above may be prepared by reaction of appropriately substituted aldehydes in the presence of either sodium cyanoboro-hydride or hydrogen gas and 10% palladium on carbon in a suitable solvent such as water, methanol, tetrahydrofuran mixtures or toluene or the like at room temperature.

Referring to Methods 27 and 28, amines 2 wherein at least one substituent of A is defined as hydroxy and X is defined above can be prepared by reaction of the corresponding ester such as acetate with an appropriate base such as sodium bicarbonate or sodium hydroxide in a suitable solvent mixture such as methanol-water mixtures at temperatures ranging from room temperature to the reflux temperature of the solvent.

Referring to Method 29, amines 2 wherein at least one substituent of A is defined as 2-hydroxybenzamido and X is defined above can be prepared by reaction of the corresponding N-(4-aminophenyl)phthalimide with lithium borohydride in an appropriate solvent such as tetrahydrofuran, diethyl ether, or the like at room temperature.

The intermediate amines 2 wherein X equals either —CH$_2$— or —(CH$_2$)$_2$— can be prepared by the following procedures:

a) reduction of an appropriately substituted benzophenyl- or corresponding heteroarylacetonitrile with borane-dimethylsulfide complex in a suitable solvent such as ethylene glycol dimethyl ether, tetrahydrofuran or the like a temperatures ranging from room temperature to the reflux temperature of the solvent. (Method 44);

17. reduction under one or more atmospheres of hydrogen in the presence of a suitable catalyst such as 5% or 10% palladium on carbon and an acid such as 4-methylbenzenesulfonic acid, hydrochloric acid or the like in a suitable solvent such as ethylene glycol monomethyl ether, ethyl acetate, ethanol or the like at room temperature. (Method 50);

18. reduction with lithium aluminum hydride in a suitable solvent such as tetrahydrofuran or diethyl ether at temperatures ranging from 0° C. to room temperature. (Method 51);

The unsaturated nitro precursors which are utilized as starting materials in Method 51 and are ultimately converted to amines 2 wherein X equals —(CH$_2$)$_2$— can be prepared by reaction of an appropriately substituted benzaldehyde or corresponding heteroaryl with nitro-methane in the presence of ammonium acetate in a suitable solvent such as acetic acid at temperatures ranging from room temperature to the reflux temperature of the solvent.(Method 53); The benzaldehydes or corresponding heteroaryls, utilized as starting materials in Method 53, can be prepared by diisobutylaluminum hydride reduction of an appropriately substituted benzonitrile or corresponding heteroaryl. (Method 52) The substituted benzonitriles or corresponding heteroaryls, utilized as starting materials in Method 52, can be prepared from the corresponding aryl or heteroaryl bromide by reaction with copper cyanide in a suitable solvent such as N,N-dimethylformamide at temperatures ranging from room temperatture to the reflux temperature of the solvent. (Method 59)

For amines 2, wherein X equals either —O(CH$_2$)$_2$NH$_2$ or —S(CH$_2$)$_2$NH$_2$, the requisite nitrile precursors may be prepared by reaction of an appropriately substituted phenol, thiophenol or corresponding heteroaryl with bromoacetonitrile in the presence of a suitable base such as potassium carbonate in an appropriate solvent such as acetone at room temperature according to Method 49.

Alternatively, for amines 2, wherein X equals —(CH$_2$)$_3$—, the nitrile precursors can be prepared essentially according to the procedure of Wilk, B. *Synthetic Comm.* 23, 2481 (1993), by reaction of an appropriately substituted phenethanol or corresponding heteroaryl with acetone cyanohydrin and triphenylphosphine in the presence of a suitable azodicarboxylate such as diethyl azodicarboxylate in an appropriate solvent such as diethyl ether or tetrahydrofuran or the like at temperatures ranging from 0° C. to room temperature. (Method 54)

Alternatively, intermediate amines 2 wherein X equals —(CH(CH$_3$))— can be prepared by acid or base catalyzed hydrolysis of the corresponding formamide using an appropriate acid catalyst such as 6N hydrochloric acid or a suitable base catalyst such as 5N sodium or potassium hydroxide in an appropriate solvent mixture such as water and methanol or water and ethanol at temperatures ranging from room temperature to the reflux temperature of the solvent. (Method 46)

The formamide precursors utilized as starting materials in Method 46 and which are ultimately converted into amines 2, are prepared according to Method 45 by treatment of an appropriately substituted acetophenone with ammonium formate, formic acid and formamide at temperatures ranging from room temperature to the reflux temperature of the solvent.

Alternatively, amines 2 wherein X equals —(CH(CH$_3$))— can be prepared by reduction of an appropriately substituted O-methyl oxime in the presence of sodium borohydride and zirconium tetrachloride in a suitable solvent such as tetrahydrofuran or diethyl ether at room temperature Method 48 essentially according to the procedure of Itsuno, S., Sakurai, Y., Ito, K. *Synthesis* 1988, 995. The requisite O-methyl oximes can be prepared from the corresponding acetophenone by reaction with methoxylamine hydrochloride and pyridine in a suitable solvent such as ethanol or methanol at temperatures ranging from room temperature to the reflux temperature of the solvent. (Method 47)

Amines 2 for which X equals —CH(J)— where J is defined as above, can be prepared by reduction of the appropriately substituted ketone by the methods described above (Methods 45, 47, and 48). These requisite ketones, when not commercially available, can be prepared by reaction of a suitably substituted benzaldehyde with an appropriate organometallic reagent such as phenyllithium, isopropylmagnesium bromide or ethylmagnesium bromide or the like in a suitable solvent such as diethyl ether or tetrahydrofuran at temperatures ranging from -78° C. to 0° C. (Method 57) The resulting alcohols can be oxidized to the corresponding ketone with an appropriate oxidizing agent such as chromium trioxide in aqueous sulfuric acid and acetone or pyridinium chlorochromate or pyridium dichromate in an appropriate solvent such as dichloromethane or the like at room temperature. (Method 58)

The intermediate anilines 5 may be prepared as previously described Method 3A. Thus treating phenyl carbamic acid tert-butyl ester 6, wherein G is described as above, with neat trifluoroacetic acid at room temperature followed by neutralization with aqueous sodium hydroxide affords the desired anilines 5. The requisite carbamic acid esters 6, wherein R$_9$–R$_{12}$ and G are described as above, are prepared as shown in Method 2C by reaction of substituted acid chlorides, 8, where G is described as above, and 4-aminophenylcarbamic acid tert-butyl esters 7, wherein R$_9$–R$_{12}$ are described above, in the presence of triethylamine in an appropriate solvent such as dichloromethane, dimethylsulfoxide, or dimethylformamide or mixturestthereof. Carboxylic acid chlorides 8 are either commercially available or prepared from the corresponding carboxylic acid by reaction with oxalyl chloride in a suitable solvent such as dichloromethane at room temperature.

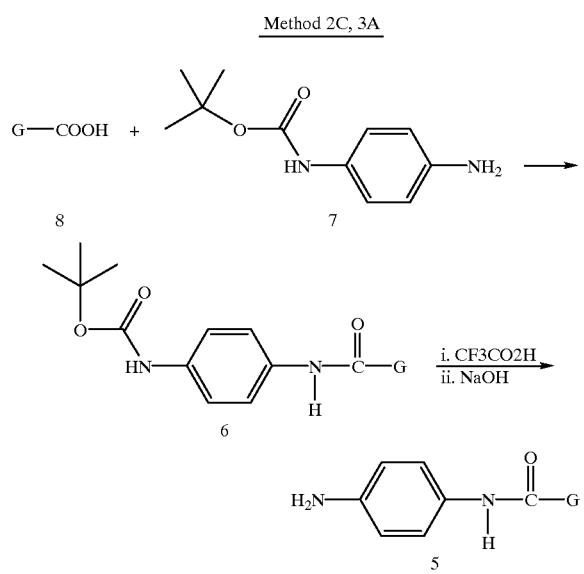

Method 2C, 3A

Alternatively, carbamic acid esters 6, wherein R$_1$–R$_{12}$ and G are described as above, are prepared as shown in Method 2E by reaction of substituted carboxylic acids 8a, wherein G is described as above, and an appropriately substituted 4-aminophenyl carbamic acid tert-butyl esters 7 in the presence of a suitable coupling agent such as benzotriazole-1-yloxy-tris-(dimethylamino)phosphonium hexafluorophosphate, 2-(1H-benzotriazole-1-yloxy)-1,1,3,3-tetramethyluronium hexafluorophosphage, dicyclo-hexyl carbodiimide or the like and in the presence of a tertiary amine base such as triethylamine or diisopropylethylamine in a suitable solvent such as dichloromethane, dimethylformamide and the like, at room temperature to produce the corresponding arylaminoamide.

Carboxylic acids 8a are either commercially available or are prepared according to literature methods. For example, when G is a substituted thiadiazole, the acid is available from the corresponding carboxylic acid ester by reaction with an appropriate base such as sodium or potassium hydroxide in a suitable solvent mixture such as methanol or ethanol and water at room temperature.

Similarly, when G is either substituted or unsubstituted thiazole, substituted or unsubstituted oxazole, substituted or unsubstituted isothiazole or substituted or unsubstituted isoxazole, when not commercially available, the corresponding carboxylic acid 8a is available from the corresponding ethyl or methyl ester by reaction with an appropriate base such as sodium or potassium hydroxide in a suitable solvent mixture such as methanol or ethanol and water at room temperature. These esters are either commercially available or can be prepared according to literature methods.

When the carboxylic acid ester precursors which are ultimately converted to acids 8a are not commmercially available, they may be prepared by methods known in the literature. For example, 5-substituted-1,2,3-thiadiazole-4 carboxylic acid esters may be prepared essentially according to the procedure of Caron, M *J. Org. Chem.* 51, 4075 (1986) and Taber, D. F., Ruckle, R. E. *J. Amer. Chem. Soc.* 108, 7686 (1986). Thus, according to Method 21, treatment of a beta-keto carboxylic acid ester with 4-methylbenzenesulfonyl azide or methanesulfonyl azide or the like in the presence of a tertiary amine base such triethylamine or diisopropylethylamine in a suitable solvent such as acetonitrile affords the corresponding diazo-beta-keto carboxylic acid ester. Treatment of this compound with 2,4-bis(4-methoxyphenyl)-1,3-dithia-2,4-diphosphetane-2,4-disulfide in a suitable solvent such as benzene or toluene or the like at temperatures ranging from room temperature to the reflux temperature of the solvent gives the desired 5-substituted-1,2,3-thiadiazole-4-carboxylic acid ester.

Alternatively, 4-substituted-1,2,3-thiadiazole -5-carboxylic acid esters may be prepared essentially according to the procedure of Shafiee, A., Lalezari, I., Yazdani, S., Shahbazian, F. M., Partovi, T. *J. Pharmaceutical Sci.* 65, 304 (1976). Thus, according to Method 22 and 23, reaction of an appropriately substituted beta-keto carboxylic acid ester in a suitable alcoholic solvent such as methanol or ethanol with an aqueous solution semicarbazide hydrochloride at temperatures ranging from room temperature to the reflux temperature of the solvent in the presence of a suitable base such as pyridine gives corresponding semicarbazone derivative. Treatment of this compound with neat thionyl chloride at 0° C. followed by treatment with an excess aqueous solution of sodium bicarbonate affords the corresponding 4-substituted-1,2,3-thiadiazole -5-carboxylic acid esters.

4-carboalkoxythiazoles are prepared essentially according to the procedure of Schöllkopf, U., Porsch, P., Lau, H. *Liebigs Ann. Chem.* 1444 (1979). Thus, according to Method 55 and 56, reaction of ethyl isocyanoacetate with N,N-dimethylformamide dimethyl acetal in a suitable alcoholic solvent such as ethanol at room temperature gives the corresponding 3-dimethylamino-2-isocyano-acrylic acid ethyl ester. A solution of this compound in a suitable solvent such as tetrahydrofuran is treated with gaseous hydrogen sulfide in the presence of a suitable tertiary amine base such as triethylamine or diiso-propylethylamine or the like at room temperature to give the corresponding 4-carboethoxythiazole.

Additional appropriately substituted thiazoles may be prepared essentially according to the procedure of Bredenkamp, M. W., Holzafel, C. W., van Zyl, W. J. *Synthetic Comm.* 20, 2235 (1990). Appropriate unsaturated oxazoles are prepared essentially according to the procedure of Henneke, K. H., Schöllkopf, U., Neudecker, T. *Liebigs Ann. Chem.* 1979 (1979). Substituted oxazoles may be prepared essentially according to the procedures of Galeotti, N., Montagne, C., Poncet, J., Jouin, P. *Tetrahedron Lett.* 33, 2807, (1992) and Shin, C., Okumura, K., Ito, A., Nakamura, Y. *Chemistry Lett.* 1305, (1994).

The following specific examples are illustrative, but are not meant to be limiting of the present invention.

EXAMPLE 1

(Method 1A)

4-Methoxy-3-trifluoromethyl-phenylamine

A suspension of 4-methoxy-3-trifluoromethyl-nitrobenzene (2.2 g) and iron powder (1.68 g) in ethanol (35 mL) and water (15 mL) is treated with a solution of concentrated hydrochloric acid (0.42 mL) in ethanol (6 mL) and water (3 mL) and the mixture is heated to reflux for approximately 1 hour. The mixture is then cooled, filtered, and concentrated under reduced pressure. The resulting oil is dissolved in ethyl acetate and extracted three times with 5% aqueous hydrochloric acid. The pooled acidic extracts are then cooled in an ice bath and basified with solid potassium carbonate, then extracted with ethyl acetate. These organic extracts are washed with saturated aqueous sodium chloride, dried over anhydrous sodium sulfate, concentrated under reduced pressure, then passed through a short column of silica gel (ethyl acetate is used as the eluant) to provide the desired compound as an amber oil.

Using the above procedure and appropriate starting materials the following compounds were prepared:

2,6-Dichloro-benzene-1,4-diamine
3-Chloro-4-methylsulfanyl-phenylamine
2,6-Dibromo-benzene-1,4-diamine
3-Chloro-4-trifluoromethyl-phenylamine
3-Chloro-4-ethylsulfanyl-phenylamine
4-Methoxy-3-trifluoromethyl-phenylamine
3,5-Dichloro-4-methoxy-2-methyl-phenylamine
5-Chloro-2-ethoxy-4-methoxy-phenylamine
5-Chloro-4-ethoxy-2-methoxy-phenylamine
5-Iodo-2,4-dimethoxy-phenylamine
3,5-Diiodo-2,4-dimethoxy-phenylamine
3,5-Dibromo-2,4-dimethoxy-phenylamine
5-Chloro-2-methoxy-4-methyl-phenylamine
2-Chloro-N(1),N(1)-dimethyl-benzene-1,4-diamine
3-Chloro-4-piperidin-1-yl-phenylamine
3-Chloro-4-pyrrolidin-1-yl-phenylamine
N(1)-Benzyl-2-chloro-benzene-1,4-diamine
3-Chloro-4-(4-methyl-piperazin-1-yl)-phenylamine
2-Chloro-N(1)-methyl-N(1)-(1-methyl-piperidin-4-yl)-benzene-1,4-diamine
2-Chloro-N(1)-methyl-N(1)-(1-methyl-pyrrolidin-3-yl)-benzene-1,4-diamine
2-Chloro-N(1)-methyl-N(1)-phenyl-benzene-1,4-diamine
N(1)-(1-Benzyl-pyrrolidin-3-yl)-2-chloro-N(1)-methyl-benzene-1,4-diamine
2-Chloro-N(1)-cyclopentyl-N(1)-methyl-benzene-1,4-diamine
2-[(4-Amino-2-chloro-phenyl)-(2-hydroxy-ethyl)-amino]-ethanol
2-Chloro-N(1)-hexyl-N(1)-methyl-benzene-1,4-diamine
2-Chloro-N(1)-isobutyl-N(1)-methyl-benzene-1,4-diamine
2-[(4-Amino-2-chloro-phenyl)-methyl-amino]-ethanol
2-Chloro-N(1)-(3-dimethylamino-propyl)-N(1)-methyl-benzene-1,4-diamine
2-Chloro-N(1)-(2-dimethylamino-ethyl)-N(1)-methyl-benzene-1,4-diamine
2-Chloro-N(1)-(2-dimethylamino-ethyl)-benzene-1,4-diamine
N(1)-(1-Benzyl-piperidin-4-yl)-2-chloro-benzene-1,4-diamine
2-Chloro-N(1)-(2-methoxy-ethyl)-N(1)-methyl-benzene-1,4-diamine
2-Chloro-N(1)-(3-dimethylamino-propyl)-benzene-1,4-diamine
N(1)-(1-Benzyl-pyrrolidin-3-yl)-2-chloro-benzene-1,4-diamine
3-Chloro-4-(1-methyl-piperidin-4-yloxy)-phenylamine
3-Chloro-4-(2-dimethylamino-ethoxy)-phenylamine
3-Chloro-4-(3-dimethylamino-propoxy)-phenylamine
3-Chloro-4-(1-methyl-pyrrolidin-3-yloxy)-phenylamine
3-Chloro-4-cyclohexyloxy-phenylamine

EXAMPLE 2

(Method 1B)

4-Bromo-2,4-dimethoxy-phenylamine

A suspension of 4-bromo-2,4-dimethoxy-nitrobenzene (0.48 g) and iron powder (0.42 g) in acetic acid (10 mL) and ethanol (10 mL) is heated to 120° C. for approximately 5 hours. The mixture is then cooled, filtered, and concentrated under reduced pressure. Water is added and the mixture is cooled in an ice bath and neutralized with solid potassium carbonate and then extracted with dichloromethane. These organic extracts are washed with saturated aqueous sodium chloride, dried over anhydrous sodium sulfate, concentrated under reduced pressure, then chromatographed over silica gel (20% ethyl acetate in hexanes is used as the eluant) to provide the desired compound as an amber oil.

EXAMPLE 3

(Method 1C)

(4-Amino-2,6-dichloro-phenoxy)-acetic Acid Tert-butyl Ester

A soution of (4-nitro-2,6-dichloro-phenoxy)-acetic acid tert-butyl ester (1 g) in ethanol (17 mL) and water (8.6 mL) is treated with iron powder (0.861 g) and ammonium chloride (86 mg) and the mixture is heated to reflux for approximately 1 hour. The mixture is then filtered and concentrated under reduced pressure. The resulting oil is partitioned between water and ethyl acetate, and the organic phase is then washed with saturated aqueous sodium chloride, dried over anhydrous sodium sulfate, and concentrated under reduced pressure to provide the desired compound as a pale yellow solid.

Using the above procedure and appropriate starting materials the following compounds were prepared:
4-Chloro-benzene-1,2-diamine
N-(4-Amino-2-chloro-phenyl)-acetamide
(4-Amino-2,6-dichloro-phenoxy)-acetonitrile
(4-Amino-2,6-dichloro-phenoxy)-acetic acid tert-butyl ester
(2-Amino-4-chloro-5-methoxy-phenoxy)-acetonitrile
(4-Amino-2-chloro-5-methoxy-phenoxy)-acetic acid methyl ester
(4-Amino-2-chloro-5-methoxy-phenoxy)-acetic acid tert-butyl ester
(2-Amino-4-chloro-5-methoxy-phenoxy)-acetic acid tert-butyl ester
N(1)-Benzyl-4-chloro-5-methoxy-benzene-1,2-diamine
N-(4-Amino-2-chloro-phenyl)-2-fluoro-benzamide
N-(4-Amino-5-chloro-2-hydroxy-phenyl)-acetamide
N-(4-Amino-5-chloro-2-hydroxy-phenyl)-2-fluoro-benzamide
Furan-2-carboxylic acid (4-amino-2-chloro-phenyl)-amide
(4-Amino-2-chloro-phenyl)-carbamic acid ethyl ester
N-(4-Amino-5-chloro-2-methyl-phenyl)-acetamide
N-(4-Amino-5-chloro-2-methyl-phenyl)-2-fluoro-benzamide
Furan-2-carboxylic acid (4-amino-5-chloro-2-methyl-phenyl)amide
N-(4-Amino-3-chloro-phenyl)-2-fluoro-benzamide
Furan-2-carboxylic acid (4-amino-3-chloro-phenyl)-amide
N-(4-Amino-2-chloro-phenyl)-2-dimethylamino-acetamide
N-(4-Amino-2-chloro-phenyl)-2-piperidin-1-yl-acetamide
N-(4-Amino-2-chloro-phenyl)-2-morpholin-4-yl-acetamide
N-(4-Amino-2-chloro-phenyl)-methanesulfonamide
N-(4-Amino-2-chloro-phenyl)-benzamide
N-(4-Amino-2-chloro-phenyl)-2-diethylamino-acetamide
N-(4-Amino-2-chloro-phenyl)-2-pyrrolidin-1-yl-acetamide
N-(4-Amino-2-chloro-phenyl)-2-azepan-1-yl-acetamide
N-(4-Amino-2-chloro-phenyl)-2-(2-methyl-piperidin-1-yl)-acetamide
N-(4-Amino-2-chloro-phenyl)-2-(3-methyl-piperidin-1-yl)-acetamide
3-Chloro-benzene-1,2-diamine
4-Chloro-N,N-dimethyl-benzene-1,2-diamine

EXAMPLE 4

(Method 1D)

3,5-Dichloro-4-phenoxy-phenylamine

To a slurry of 3,5-dichloro-4-phenoxy-nitrobenzene (6.1 g) and tin powder (12 g) is added dropwise concentrated hydrochloric acid (60 mL). Ethanol (60 mL) is added and the mixture is heated to reflux for approximately 1 hour. The mixture is then cooled in an ice bath and basified by addition of solid sodium hydroxide. The resulting suspension is filtered through a pad of diatomaceous earth and extracted three times with ethyl acetate. The combined organic extracts are then washed with saturated aqueous sodium chloride, dried over anhydrous magnesium sulfate, and concentrated under reduced pressure to provide the desired product as a yellow solid. Recrystallization from ethyl acetate-hexanes provided the product as a pale yellow solid.

Using the above procedure and appropriate starting materials the following compounds were prepared:
1-Furan-2-yl-ethylamine
3-Chloro-4-isopropoxy-phenylamine
2-Butoxy-5-chloro-4-methoxy-phenylamine
3,5-Dichloro-2-methoxy-4-methyl-phenylamine
2-Benzyloxy-5-chloro-4-methoxy-phenylamine
4-Benzyloxy-5-chloro-2-methoxy-phenylamine
5-Fluoro-2,4-dimethoxy-phenylamine
(4-Amino-2,6-dichloro-phenoxy)-acetic acid ethyl ester
3,5-Dichloro-4-phenoxy-phenylamine
2-(4-Amino-2-chloro-5-methoxy-phenoxy)-acetamide
(4-Amino-2-chloro-5-methoxy-phenoxy)-acetonitrile
2-(2-Amino-4-chloro-5-methoxy-phenoxy)-ethanol
2-(4-Amino-2-chloro-5-methoxy-phenoxy)-ethanol
4-(4-Amino-2-chloro-5-methoxy-phenoxy)-butyronitrile
4-Amino-2-chloro-5-methoxy-phenol
2-Amino-4-chloro-5-methoxy-phenol
5-Chloro-4-methoxy-2-morpholin-4-yl-phenylamine
4-Chloro-5-methoxy-N(1),N(1)-dimethyl-benzene-1,2-diamine
5-Chloro-4-methoxy-2-piperidin-1-yl-phenylamine
5-Chloro-4-methoxy-2-pyrrolidin-1-yl-phenylamine
2-Chloro-N(1)-cyclohexyl-N(1)-methyl-benzene-1,4-diamine
N(2)-Benzyl-4-methoxy-benzene-1,2-diamine
2-(4-Amino-2-chloro-phenoxy)-ethanol
2-Chloro-N(1)-cyclohexyl-N(1)-ethyl-benzene-1,4-diamine
4-Butoxy-3-chloro-phenylamine
(4-Amino-2-chloro-phenoxy)-acetonitrile
2-Chloro-N(1)-cyclohexyl-benzene-1,4-diamine
2-Chloro-N(1),N(1)-dipropyl-benzene-1,4-diamine
3-Chloro-4-(2,2,2-trifluoro-ethoxy)-phenylamine
3-Chloro-4-(octahydro-quinolin-1-yl)-phenylamine
N(1)-Allyl-2-chloro-N(1)-cyclohexyl-benzene-1,4-diamine
N-(4-Amino-2-methoxy-5-methyl-phenyl)-2-fluoro-benzamide
Furan-2-carboxylic acid (4-amino-2-methoxy-5-methyl-phenyl)amide N-(4-Amino-naphthalen-1-yl)-2-fluoro-benzamide
3-Chloro-N,N-dimethyl-benzene-1,2-diamine
3-Chloro-4-propoxy-phenylamine
3-Iodo-4-methoxy-phenyl amine
3-Chloro-2,4-dimethoxy-aniline
3-Bromo-4-methoxy-phenylamine
3-Chloro-4-ethoxy-phenylamine

EXAMPLE 5

(Method 1E)

(4-Amino-phenyl)-carbamic Acid Isobutyl Ester

To a solution of N-(4-Nitro-phenyl)-isobutyrlamide (2.0 g) in 100 mL ethylene glycol monomethyl ether (100 mL) is added 10% palladium on carbon (275 mg). The mixture is hydrogenated for 2 hours at room temperature under 30 psi of hydrogen on a Parr hydrogenation apparatus. The catalyst is then removed by filtration through diatomaceous earth and the filtrate is evaporated to dryness under reduced pressure by azeotroping three times with heptane. Trituration of the residue with heptane provides the desired product as a white solid.

Using the above procedure and appropriate starting materials the following compounds were prepared:
2-Methyl-3H-benzoimidazol-5-ylamine
N-(4-Amino-phenyl)-formamide
1H-Benzoimidazol-5-ylamine
(4-Amino-phenyl)-carbamic acid isobutyl ester
N-(4-Amino-phenyl)-isobutyramide
N-(5-Amino-pyridin-2-yl)-2-methyl-benzamide
Furan-2-carboxylic acid (5-amino-pyridin-2-yl)-amide
N-(5-Amino-pyridin-2-yl)-2-fluoro-benzamide
[6-(2,2,2-Trifluoro-acetylamino)-pyridin-3-yl]-carbamic acid tert-butyl ester
N-(5-Amino-pyridin-2-yl)-2,2,2-trifluoro-acetamide
(4-Amino-benzyl)-carbamic acid tert-butyl ester
2-(3,5-Bis-trifluoro methyl-phenyl)-ethyl amine
1-tert-Butyl-1H-imidazol-2-ylamine
3-(3-Dimethylamino-propyl)-5-trifluoromethyl-phenylamine

EXAMPLE 6

(Method 1F)

N-(4-Amino-2-methylphenyl)-2-fluorobenzamide

A mixture of 2-fluoro-N-(2-methyl-4-nitrophenyl) benzamide (4.55 g), cyclohexene (30 mL), ethanol (70 mL), water (30 mL) and 10% palladium on charcoal (3 g) is heated at reflux for 30 minutes. The mixture is filtered through diatomaceous earth and concentrated under reduced pressure. The resulting oil is dissolved in 50 mL of ethyl acetate and cooled at 4° C. for 12 hours. Filtration provides the product as a tan solid.

Using the above procedure and appropriate starting materials the following compounds were prepared:
N-(4-Amino-2-methyl-phenyl)-acetamide
2-Methyl-benzooxazol-6-ylamine
N-(4-Amino-3-methoxy-phenyl)-acetamide
2-Acetylamino-5-amino-benzoic acid
N-(4-Amino-phenyl)-acetamide
[4-(3-Amino-benzoylamino)-phenyl]-carbamic acid tert-butyl ester
[4-(2-Amino-benzoylamino)-phenyl]-carbamic acid tert-butyl ester
N-(4-Amino-2-cyano-phenyl)-acetamide
N-(4-Amino-2,5-dimethoxy-phenyl)-2-fluoro-benzamide
Furan-2-carboxylic acid (4-amino-2,5-dimethoxy-phenyl)-amide
N-(4-Amino-2-cyano-phenyl)-2-fluoro-benzamide
Furan-2-carboxylic acid (4-amino-2-methoxy-phenyl)-amide
N-(4-Amino-2-methoxy-phenyl)-2-fluoro-benzamide
N-(4-Amino-2-methoxy-5-methyl-phenyl)-acetamide
N-(4-Amino-2-benzoyl-phenyl)-acetamide
N-(4-Amino-2-benzoyl-phenyl)-2-fluoro-benzamide
Furan-2-carboxylic acid (4-amino-2-benzoyl-phenyl)-amide
N-(4-Amino-3-methyl-phenyl)-acetamide
N-(4-Amino-3-methyl-phenyl)-2-fluoro-benzamide
Furan-2-carboxylic acid (4-amino-3-methyl-phenyl)-amide
5-Amino-2-[(2-fluorobenzoyl)amino]-N-phenylbenzamide
Furan-2-carboxylic acid (4-amino-2-phenylcarbamoyl-phenyl)amide
N-(4-Amino-naphthalen-1-yl)-acetamide
Furan-2-carboxylic acid (4-amino-naphthalen-1-yl)-amide
N-(4-Amino-2-trifluoromethyl-phenyl)-acetamide
Furan-2-carboxylic acid (4-amino-2-cyano-phenyl)-amide
Furan-2-carboxylic acid (4-amino-2-trifluoromethyl-phenyl)-amide
N-(4-Amino-2-methyl-phenyl)-2-fluoro-benzamide
Furan-2-carboxylic acid (4-amino-2-methyl-phenyl)-amide
5-Amino-2-(2-fluoro-benzoylamino)-benzoic acid
5-Amino-2-[(furan-2-carbonyl)-amino]-benzoic acid
N-(4-Amino-2-cyano-phenyl)-2,2,2-trifluoro-acetamide
N-(4-Amino-3-methyl-phenyl)-2,6-difluoro-benzamide
N-(4-Amino-3-trifluoromethyl-phenyl)-acetamide
N-(4-Amino-3-trifluoromethyl-phenyl)-2-fluoro-benzamide
N-(4-Amino-2-trifluoromethyl-phenyl)-2,2,2-trifluoro-acetamide
N-(4-Amino-2-methoxy-phenyl)-2,2,2-trifluoro-acetamide
N-(4-Amino-2-trifluoromethyl-phenyl)-2-fluoro-N-(2-fluoro-benzoyl)-benzamide
N-(4-Amino-2-trifluoromethyl-phenyl)-2-fluoro-benzamide

EXAMPLE 7

(Method 1G)

N-(4-Amino-2-chlorophenyl)-2-thiomorpholino-4-yl-acetamide

A solution of N-(2-chloro-4-nitrophenyl)-2-thiomorpholino-4-yl-acetamide (3.02 g) in ethanol (200 mL) is added to a solution of sodium thiosulfate (12 g) in water (60 mL). The mixture is heated at reflux for 12 hours, cooled and poured into water. The mixture is then extracted with ethyl acetate. The ethyl acetate solution is washed twice with saturated aqueous sodium chloride, dried over anhydrous potassium carbonate, filtered through a pad of diatomaceous earth and concentrated under reduced pressure to give an oil. Toluene is added and the solution chilled to give the desired product as a light orange crystalline solid.

Using the above procedure and appropriate starting materials the following compounds were prepared:
N-(4-Amino-2-chloro-phenyl)-2-thiomorpholin-4-yl-acetamide
N-(4-Amino-2-chloro-phenyl)-2-dipropylamino-acetamide

EXAMPLE 8

(Method 2A)

(3-Chloro-4-iodo-phenyl)-carbamic Acid Tert-butyl Ester

To a solution of 3-chloro-4-iodo-aniline (10 g) in tetrahydrofuran (40 mL) containing diiso-propylethylamine (6.9 mL) is added di-tert-butyl-dicarbonate (8.6 g) and the mixture is heated to reflux. After approximately 15 hours additional portions of diisopropylethylamine (6.9 mL) and di-tert-butyl-dicarbonate (21 g) is added and heating is continued for approximately 24 hours. The solution is then cooled, concentrated under reduced pressure, diluted with ethyl acetate, and washed successively three times with 5% aqueous hydrochloric acid then once with saturated aqueous sodium chloride. The solution is dried over anhydrous sodium sulfate then concentrated under reduced pressure to provide the desired crude product as a brown oil. Crystallization is induced by addition of hexanes, and the collected solid material is recrystallized from hexanes to give the desired product as a white solid.

Using the above procedure and appropriate starting materials the following compounds were prepared:

N'-(4-Nitro-benzoyl)-hydrazinecarboxylic acid tert-butyl ester
(3-Chloro-4-iodo-phenyl)-carbamic acid tert-butyl ester
(4-Bromo-3-chloro-phenyl)-carbamic acid tert-butyl ester
(3-Chloro-4-vinyl-phenyl)-carbamic acid tert-butyl ester
(3-Chloro-4-methylsulfanyl-phenyl)-carbamic acid tert-butyl ester
(4-Amino-3-chloro-phenyl)-carbamic acid tert-butyl ester
(4-Chloro-2-nitro-phenyl)-carbamic acid tert-butyl ester
(3-tert-Butoxycarbonylamino-5-chloro-phenyl)-carbamic acid tert-butyl ester
(4-Nitro-benzyl)-carbamic acid tert-butyl ester
(3-Bromo-5-trifluoromethyl-phenyl)-carbamic acid tert-butyl ester
(2-Amino-3-chloro-5-trifluoromethyl-phenyl)-carbamic acid tert-butyl ester

EXAMPLE 9

(Method 2B)

(3-Chloro-4-vinyl-phenyl)-carbamic Acid 2-trimethylsilanyl-ethyl Ester

To a solution of 3-chloro-4-vinyl-phenylamine (3.4 g) in N,N-dimethylformamide (44 mL) containing diisopropylethylamine (5.8 mL) is added 1-[2-(trimethylsilyl)-ethoxycarbonyl-oxy]benzotriazole (7.1 g) and the mixture is stirred at room temperature under an atmosphere of argon for three days. The solution is then diluted with water and extracted three times with diethyl ether. The combined organic extracts are washed successively with water, saturated aqueous sodium chloride, dried over anhydrous magnesium sulfate, and concentrated under reduced pressure. The resulting residue is chromatographed over silica gel (10% ethyl acetate in hexanes is used as the eluant) to provide the desired product as a yellow oil.

EXAMPLE 10

(Method 2C)

[4-(2-Fluoro-benzoylamino)-phenyl]-carbamic Acid tert-butyl Ester

To a solution of mono-N-(t-butoxycarbonyl)-1,4-phenylenediamine (1.58 g) and triethylamine (1.50 mL) in 25 mL of dichloromethane is added o-fluorobenzoyl chloride (1.20 g). A solid formed immediately forms and is filtered and washed with fresh solvent to yield a white solid, 1.90 g.

Using the above procedure and appropriate starting materials the following compounds were prepared:

N-(3-Methoxy-4-nitro-phenyl)-acetamide
N-(4-Amino-phenyl)-isobutyrlamide
2,2,2-Trifluoro-N-(2-methoxy-4-nitro-phenyl)-acetamide
[4-(2-Methyl-benzoylamino)-phenyl]-carbamic acid tert-butyl ester
Acetic acid 2-(4-tert-butoxycarbonylamino-phenylcarbamoyl)-phenyl ester
[4-(4-Fluoro-benzoylamino)-phenyl]-carbamic acid tert-butyl ester
[4-(3-Fluoro-benzoylamino)-phenyl]-carbamic acid tert-butyl ester
[4-(2-Fluoro-benzoylamino)-phenyl]-carbamic acid tert-butyl ester
[4-(2-Methoxy-benzoylamino)-phenyl]-carbamic acid tert-butyl ester
[4-(3-Methoxy-benzoylamino)-phenyl]-carbamic acid tert-butyl ester
[4-(4-Methoxy-benzoylamino)-phenyl]-carbamic acid tert-butyl ester
[4-(2,2-Dimethyl-propionylamino)-phenyl]-carbamic acid tert-butyl ester
[4-(2-Bromo-acetylamino)-phenyl]-carbamic acid tert-butyl ester
[4-(2,2,2-Trifluoro-acetylamino)-phenyl]-carbamic acid tert-butyl ester
(4-Benzoylamino-phenyl)-carbamic acid tert-butyl ester
(4-Methanesulfonylamino-phenyl)-carbamic acid tert-butyl ester
(4-Phenylacetylamino-phenyl)-carbamic acid tert-butyl ester
{4-[(Thiophene-2-carbonyl)-amino]-phenyl}-carbamic acid tert-butyl ester
[4-(3-Nitro-benzoylamino)-phenyl]-carbamic acid tert-butyl ester
[4-(3-Acetylamino-benzoylamino)-phenyl]-carbamic acid tert-butyl ester
[4-(3-Methanesulfonylamino-benzoylamino)-phenyl]-carbamic acid tert-butyl ester
Ethyl [3-[[[4-[[(1,1-dimethylethoxy)carbonyl]amino]phenyl]amino]carbonyl]phenyl]carbamate
[4-(2-Trifluoromethyl-benzoylamino)-phenyl]-carbamic acid tert-butyl ester
[4-(2,6-Difluoro -benzoylamino)-phenyl]-carbamic acid tert-butyl ester
[4-(2-Chloro-benzoylamino)-phenyl]-carbamic acid tert-butyl ester
[4-(2-Bromo-benzoylamino)-phenyl]-carbamic acid tert-butyl ester
[4-(2-Nitro-benzoylamino)-phenyl]-carbamic acid tert-butyl ester
{(4-[(Benzo [b]thiophene-2-carbonyl)-amino]-phenyl}-carbamic acid tert-butyl ester
{(4-[(Pyridine-4-carbonyl)-amino]-phenyl}-carbamic acid tert-butyl ester
{(4-[(Naphthalene-2-carbonyl)-amino]-phenyl}-carbamic acid tert-butyl ester
{4-[(Naphthalene-1-carbonyl)-amino]-phenyl)}-carbamic acid tert-butyl ester
{(4-[(3-Bromo-thiophene-2-carbonyl)-amino]-phenyl}-carbamic acid tert-butyl ester
{4-[(Biphenyl-2-carbonyl)-amino]-phenyl}-carbamic acid tert-butyl ester
N-(4-tert-Butoxycarbonylamino-phenyl)-phthalamic acid
[4-(2,3-Difluoro-benzoylamino)-phenyl]-carbamic acid tert-butyl ester
[4-(2,5-Difluoro-benzoylamino)-phenyl]-carbamic acid tert-butyl ester

[4-(2,4-Difluoro-benzoylamino)-phenyl]-carbamic acid tert-butyl ester
[4-(2-Acetylamino-benzoylamino)-phenyl]-carbamic acid tert-butyl ester
[4-(2-Methanesulfonylamino-benzoylamino)-phenyl]-carbamic acid tert-butyl ester
[4-(2,3,4-Trifluoro-benzoylamino)-phenyl]-carbamic acid tert-butyl ester
[4-(2,3,4,5,6-Pentafluoro-benzoylamino)-phenyl]-carbamic acid tert-butyl ester
N-(4-tert-Butoxycarbonylamino-phenyl)-isophthalamic acid methyl ester
2-Methylsulfanyl-N-[4-(2,2,2-trifluoro-acetylamino)-phenyl]-benzamide
[4-(3-Benzyloxy-benzoylamino)-phenyl]-carbamic acid tert-butyl ester
[4-(3-Butoxy-benzoylamino)-phenyl]-carbamic acid tert-butyl ester
{4-[(5-Difluoromethyl-furan-2-carbonyl)-amino]-phenyl}-carbamic acid tert-butyl ester
{4-[(Thiophene-3-carbonyl)-amino]-phenyl}-carbamic acid tert-butyl ester
{4-[(5-Methyl-furan-2-carbonyl)-amino]-phenyl}-carbamic acid tert-butyl ester
{4-[(5-Bromo-furan-2-carbonyl)-amino]-phenyl}-carbamic acid tert-butyl ester
(4-Hexanoylamino-phenyl)-carbamic acid tert-butyl ester
[4-(2-Thiophen-2-yl-acetylamino)-phenyl]-carbamic acid tert-butyl ester
{4-[(Pyridine-3-carbonyl)-amino]-phenyl}-carbamic acid tert-butyl ester
{4-[(4-Bromo-furan-2-carbonyl)-amino]-phenyl}-carbamic acid tert-butyl ester
{4-[(Furan-3-carbonyl)-amino]-phenyl}-carbamic acid tert-butyl ester
(4-Phenoxycarbonylamino-phenyl)-carbamic acid tert-butyl ester
{4-[(Benzo[1,3]dioxole-4-carbonyl)-amino]-phenyl}-carbamic acid tert-butyl ester
[4-(3-Trifluoromethoxy-benzoylamino)-phenyl]-carbamic acid tert-butyl ester
N-(2,5-Dimethoxy-4-nitro-phenyl)-2-fluoro-benzamide
{4-[(Furan-2-carbonyl)-amino]-phenyl}-carbamic acid tert-butyl ester
[4-(2-Phenoxy-acetylamino)-phenyl]-carbamic acid tert-butyl ester
{4-[(5-Nitro-furan-2-carbonyl)-amino]-phenyl}-carbamic acid tert-butyl ester
{4-[(5-Chloro-furan-2-carbonyl)-amino]-phenyl}-carbamic acid tert-butyl ester
{4-[(3-Methyl-furan-2-carbonyl)-amino]-phenyl}-carbamic acid tert-butyl ester
[4-(2-Methoxy-acetylamino)-phenyl]-carbamic acid tert-butyl ester
{4-[(4-Furan-3-yl-[1,2,3]thiadiazole-5-carbonyl)-amino]-phenyl}-carbamic acid tert-butyl ester
{4-[(5-tert-Butyl-furan-2-carbonyl)-amino]-phenyl}-carbamic acid tert-butyl ester
N-[3-Cyano-4-(2,2,2-trifluoro-acetylamino)-phenyl]-2-fluoro-benzamide
Furan-2-carboxylic acid [3-cyano-4-(2,2,2-trifluoro-acetylamino)-phenyl]amide
N-(4-Acetylamino-2-cyano-phenyl)-2,2,2-trifluoro-acetamide
2,2,2-Trifluoro-N-(4-nitro-2-trifluoromethyl-phenyl)-acetamide
N-(4-Acetylamino-2-trifluoromethyl-phenyl)-2,2,2-trifluoro-acetamide
2-Fluoro-N-[4-(2,2,2-trifluoro-acetylamino)-3-trifluoromethyl-phenyl]benzamide
Furan-2-carboxylic acid [4-(2,2,2-trifluoro-acetylamino)-3-trifluoromethyl-phenyl]amide
2-Fluoro-N-(2-methyl-benzooxazol-6-yl)-benzamide
4-(2-Fluoro-benzoylamino)-2-hydroxy-benzoic acid phenyl ester
{4-[(Isoxazole-5-carbonyl)-amino]-phenyl}-carbamic acid tert-butyl ester
N-(4-Acetylamino-2-methoxy-phenyl)-2,2,2-trifluoro-acetamide
2-Fluoro-N-[3-methoxy-4-(2,2,2-trifluoro-acetylamino)-phenyl]benzamide
2-Fluoro-N-(2-fluoro-benzoyl)-N-(4-nitro-2-trifluoromethyl-phenyl)benzamide
{4-[(1H-Pyrazole-4-carbonyl)-amino]-phenyl}-carbamic acid tert-butyl ester
{4-[(4H-Imidazole-4-carbonyl)-amino]-phenyl}-carbamic acid tert-butyl ester
{4-[(5-Methyl-[1,2,3]thiadiazole-4-carbonyl)-amino]-phenyl}-carbamic acid tert-butyl ester
{4-[(5-Furan-3-yl-[1,2,3]thiadiazole-4-carbonyl)-amino]-phenyl}-carbamic acid tert-butyl ester
2,2,2-Trifluoro-N-(5-nitro-pyridin-2-yl)-acetamide
{4-[(1-Methyl-1H-pyrazole-4-carbonyl)-amino]-phenyl}-carbamic acid tert-butyl ester
4-(2-Fluoro-benzoylamino)-2-hydroxy-benzoic acid methyl ester
N-(5-Chloro-2,4-dimethoxy-phenyl)-oxalamic acid
Isoxazole-5-carboxylic acid (4-amino-phenyl)-amide
2-Fluoro-N-(4-nitro-benzyl)-benzamide
Furan-2-carboxylic acid 4-nitro-benzylamide
N-[3-Chloro-5-(2,2,2-trifluoro-acetylamino)-phenyl]-2,2,2-trifluoro-acetamide
N-(3-Amino-5-chloro-phenyl)-2,2,2-trifluoro-acetamide
[4-(2-Fluoro-benzoylamino)-benzyl]-carbamic acid tert-butyl ester
[4-(2,6-Difluoro-benzoylamino)-benzyl]-carbamic acid tert-butyl ester
2,6-Difluoro-N-(4-nitro-benzyl)-benzamide
{4-[(Furan-2-carbonyl)-amino]-benzyl}-carbamic acid tert-butyl ester
N-(3-Amino-5-chloro-phenyl)-acetamide
[4-(3-Chloro-benzoylamino)-phenyl]-carbamic acid tert-butyl ester
[4-(4-Chloro-benzoylamino)-phenyl]-carbamic acid tert-butyl ester
[4-(4-Dimethylamino-benzoylamino)-phenyl]-carbamic acid tert-butyl ester
(4-Benzenesulfonylamino-phenyl)-carbamic acid tert-butyl ester
[4-(3-Trifluoromethyl-benzoylamino)-phenyl]-carbamic acid tert-butyl ester
2,2,2-Trifluoro-N-(5-nitro-pyrimidin-2-yl)-acetamide

EXAMPLE 11

(Method 2D)

2-Chloro-N-(2-chloro-4-nitrophenyl)acetamide

A solution of 2-chloro-4-nitroaniline (19.0 g) and chloroacetyl chloride (30 mL) in tetrahydrofuran (150 mL) is heated at reflux for 1 hour. The solution is cooled and concentrated under reduced pressure, giving a wet yellow solid. Ether (250 mL) is added and the yellow solid is collected.

Using the above procedure and appropriate starting materias the following compounds were prepared:

N-(4-Nitro-3-trifluoromethyl-phenyl)-acetamide
(2-Chloro-4-nitro-phenyl)-carbamic acid ethyl ester
2-Acetylamino-5-nitro-benzoic acid
Furan-2-carboxylic acid (5-chloro-2-hydroxy-4-nitro-phenyl)-amide
Furan-2-carboxylic acid (2-methyl-4-nitro-phenyl)-amide
Furan-2-carboxylic acid (2-methoxy-4-nitro-phenyl)-amide
N-(2-Chloro-4-nitro-phenyl)-benzamide
2-Methoxy-N-(4-nitro-phenyl)-acetamide
N-(4-Nitro-phenyl)-acrylamide
N-(4-Nitro-phenyl)-isobutyrlamide
[4-)acryloylamino)-phenyl]carbamic acid tert-butyl ester
(4-Nitro-phenyl)-carbamic acid isobutyl ester
[1,2,3]Thiadiazole-4-carboxylic acid (5-nitro-pyridin-2-yl)-amide
Furan-2-carboxylic acid (5-nitro-pyridin-2-yl)-amide
2-Fluoro-N-(5-nitro-pyridin-2-yl)-benzamide
N-(2-Chloro-4-nitro-phenyl)-2-fluoro-benzamide
Furan-2-carboxylic acid (2,5-dimethoxy-4-nitro-phenyl)-amide
N-(2-Cyano-4-nitro-phenyl)-2-fluoro-benzamide
2-Fluoro-N-(2-methoxy-4-nitro-phenyl)-benzamide
2-Methyl-N-(5-nitro-pyridin-2-yl)-benzamide
Furan-2-carboxylic acid (2-methoxy-5-methyl-4-nitro-phenyl)-amide
2-Fluoro-N-(2-methoxy-5-methyl-4-nitro-phenyl)-benzamide
N-(2-Benzoyl-4-nitro-phenyl)-acetamide
N-(2-Benzoyl-4-nitro-phenyl)-2-fluoro-benzamide
Furan-2-carboxylic acid (2-benzoyl-4-nitro-phenyl)-amide
N-(3-Methyl-4-nitro-phenyl)-acetamide
2-Fluoro-N-(3-methyl-4-nitro-phenyl)-benzamide
Furan-2-carboxylic acid (3-methyl-4-nitro-phenyl)-amide
2-Acetylamino-5-nitro-N-phenyl-benzamide
2-[(2-Fluorobenzoyl)amino]-5-nitro-N-phenylbenzamide
Furan-2-carboxylic acid (4-nitro-2-phenylcarbamoyl-phenyl)-amide
2-Fluoro-N-(4-nitro-naphthalen-1-yl)-benzamide
Furan-2-carboxylic acid (4-nitro-naphthalen-1-yl)-amide
N-(5-Chloro-2-hydroxy-4-nitro-phenyl)-acetamide
N-(5-Chloro-2-hydroxy-4-nitro-phenyl)-2-fluoro-benzamide
Furan-2-carboxylic acid (2-chloro-4-nitro-phenyl)-amide
N-(4-Nitro-2-trifluoromethyl-phenyl)-acetamide
Furan-2-carboxylic acid (2-cyano-4-nitro-phenyl)-amide
2-Fluoro-N-(4-nitro-2-trifluoromethyl-phenyl)-benzamide
Furan-2-carboxylic acid (4-nitro-2-trifluoromethyl-phenyl)-amide
2-Fluoro-N-(2-methyl-4-nitro-phenyl)-benzamide
N-(5-Chloro-2-methyl-4-nitro-phenyl)-2-fluoro-benzamide
Furan-2-carboxylic acid (5-chloro-2-methyl-4-nitro-phenyl)-amide
2-(2-Fluoro-benzoylamino)-5-nitro-benzoic acid
2-[(Furan-2-carbonyl)-amino]-5-nitro-benzoic acid
N-(3-Chloro-4-nitro-phenyl)-2-fluoro-benzamide
Furan-2-carboxylic acid (3-chloro-4-nitro-phenyl)-amide
2,6-Difluoro-N-(3-methyl-4-nitro-phenyl)-benzamide
2-Fluoro-N-(4-nitro-3-trifluoromethyl-phenyl)-benzamide
Furan-2-carboxylic acid (4-nitro-3-trifluoromethyl-phenyl)-amide
2-Chloro-N-(2-chloro-4-nitro-phenyl)-acetamide
N-(2-Chloro-4-nitrophenyl)methanesulfonamide
Furan-2-carboxylic acid [3-methoxy-4-(2,2,2-trifluoro-acetylamino)-phenyl]-amide
N-(2-Chloro-4-nitro-phenyl)-2,2,2-trifluoro-acetamide

EXAMPLE 12

{4-[(4-Phenyl-[1,2,3]thiadiazole-5-carbonyl)-amino]-phenyl}-carbamic acid tert-butyl A solution of 1-(N-tert-butoxycarbonyl)-1,4-phenylenediamine (0.8 g) and 4-phenyl-[1,2,3]thiadiazole-5-carboxylic acid (0.7 g) in dichloromethane (10 mL) is treated with triethylamine (1.3 mL) and benzotriazole-1-yloxy-tris(dimethylamino)- phosphonium hexafluorophosphate (1.6 g). After stirring at room temperature, the reaction is diluted with water and extracted with dichloromethane. The organic layer is washed with 0.5 N hydrochloric acid, saturated sodium bicarbonate, and water then dried over magnesium sulfate, filtered, and concentrated under reduced pressure to give the desired product.

Using the above procedure and appropriate starting materials the following compounds were prepared:
{4-[(1H-Pyrrole-2-carbonyl)-amino]-phenyl}-carbamic acid tert-butyl ester
{4-[(Pyrazine-2-carbonyl)-amino]-phenyl}-carbamic acid tert-butyl ester
{4-[(5-Methyl-thiophene-2-carbonyl)-amino]-phenyl}-carbamic acid tert-butyl ester
{4-[(1-Methyl-1H-pyrrole-2-carbonyl)-amino]-phenyl}-carbamic acid tert-butyl ester
{4-[(Quinoline-8-carbonyl)-amino]-phenyl}-carbamic acid tert-butyl ester
{4-[(Benzofuran-2-carbonyl)-amino]-phenyl}-carbamic acid tert-butyl ester
{4-[(Isoquinoline-1-carbonyl)-amino]-phenyl}-carbamic acid tert-butyl ester
{4-[(Quinoline-2-carbonyl)-amino]-phenyl}-carbamic acid tert-butyl ester
{4-[(Pyridine-2-carbonyl)-amino]-phenyl}-carbamic acid tert-butyl ester
{4-[(Isoquinoline-4-carbonyl)-amino]-phenyl }-carbamic acid tert-butyl ester
{4-[([1,2,3]Thiadiazole-4-carbonyl)-amino]-phenyl)-carbamic acid tert-butyl ester
{4-[(1H-[1,2,3]Triazole-4-carbonyl)-amino]-phenyl}-carbamic acid tert-butyl ester
[4-(2-Methylsufanyl-benzoylamino)-phenyl]-carbamic acid tert-butyl ester
{4-[(Quinoline-4-carbonyl)-amino]-phenyl}-carbamic acid tert-butyl ester
{4-[(4-Methyl-[1,2,3]thiadiazole-5-carbonyl)-amino]-phenyl}-carbamic acid tert-butyl ester
{4-[(4-Phenyl-[1,2,3]thiadiazole-5-carbonyl)-amino]-phenyl}-carbamic acid tert-butyl ester
{4-[(1H-Indole-2-carbonyl)-amino]-phenyl}-carbamic acid tert-butyl ester
[1,2,3]Thiadiazole-4-carboxylic acid 4-nitro-benzylamide
{4-[([1,2,3]Thiadiazole-4-carbonyl)-amino]-benzyl}-carbamic acid tert-butyl ester
Acetic acid 4-(4-tert-butoxycarbonylamino-phenylcarbamoyl)-phenyl ester
{4-[(Quinoline-6-carbonyl)-amino]-phenyl}-carbamic acid tert-butyl ester

EXAMPLE 13

(Method 2F)

Acetic acid 2-(4-tert-butoxycarbonylamino-2,6-dichloro-phenoxy)-ethyl Ester

A solution of [3,5-dichloro-4-(2-hydroxy-ethoxy)-phenyl]-carbamic acid tert-butyl ester (0.85 g) in pyridine (14 mL) is treated with acetic anhydride (1.24 mL) and the mixture is stirred at room temperature for 15 hours. The solvent is removed under reduced pressure and the residue dissolved in ethyl acetate. This solution is then washed twice with 5% aqueous hydrochloric acid, once with saturated aqueous sodium bicarbonate, and then with saturated aqueous sodium chloride. The solution is dried over anhydrous magnesium sulfate and the solvent is removed under reduced pressure to provide the desired product as a colorless oil.

Using the above procedure and appropriate starting materials the following compounds were prepared:
Phenylsulfanyl-acetonitrile
Acetic acid 2-(4-tert-butoxycarbonylamino-2,6-dichloro-phenoxy)-ethyl ester

EXAMPLE 14

(Method 2G)

(3,5-Dichloro-4-hydroxy-phenyl)-carbamic Acid Tert-butyl Ester

To a solution of 2,6-dichloro-4-amino phenol (9.5 g) in tetrahydrofuran (130 mL) is added di-tert-butyl-dicarbonate (11.7 g) and the mixture is heated to reflux for approximately 15 hours. The solution is then cooled, concentrated under reduced pressure, diluted with ethyl acetate, and washed successively three times with 5% aqueous hydrochloric acid then once with saturated aqueous sodium chloride. The solution is dried over anhydrous sodium sulfate then concentrated under reduced pressure to provide the desired crude product. This material is then triturated with cold dichloromethane to provide the product as a white solid.

Using the above procedure and appropriate starting materials the following compound was prepared:
(3-Amino-5-chloro-phenyl)-carbamic acid tert-butyl ester

EXAMPLE 15

(Method 3A)

3,5-Dichloro-4-ethoxy-phenylamine

Trifluoroacetic acid (5 mL) is added to solid (3,5-dichloro-4-ethoxy-phenyl)-carbamic acid tert-butyl ester (0.97 g) and the mixture is stirred for approximately 45 minutes at room temperature. Water is then added, and the mixture is cooled in an ice bath and basified with solid potassium carbonate. The solution is extracted three times with ethyl acetate and the combined organic phases are washed with saturated aqueous sodium chloride then dried over anhydrous sodium sulfate. Concentration under reduced pressure and recrystallization from hexanes provides the desired product as a pale yellow crystalline solid.

Using the above procedure and appropriate starting materials the following compounds were prepared:
5-Bromo-pyridin-3-ylamine
3-Chloro-4-methanesulfonyl-phenylamine
N-(4-Amino-phenyl)-2-methyl-benzamide
Acetic acid 2-(4-amino-phenylcarbamoyl)-phenyl ester
N-(4-Amino-phenyl)-4-fluoro-benzamide
N-(4-Amino-phenyl)-3-fluoro-benzamide
N-(4-Amino-phenyl)-2-fluoro-benzamide
N-(4-Amino-phenyl)-2-methoxy-benzamide
N-(4-Amino-phenyl)-3-methoxy-benzamide
N-(4-Amino-phenyl)-4-methoxy-benzamide
N-(4-Amino-phenyl)-2-phenyl-acetamide
N-(4-Amino-phenyl)-2,2-dimethyl-propionamide
N-(4-Amino-phenyl)-2,2,2-trifluoro-acetamide
Thiophene-2-carboxylic acid (4-amino-phenyl)-amide
1H-Pyrrole-2-carboxylic acid (4-amino-phenyl)-amide
N-(4-Amino-phenyl)-3-nitro-benzamide
3-Acetylamino-N-(4-amino-phenyl)-benzamide
N-(4-Amino-phenyl)-3-dimethylamino-benzamide
N-(4-Amino-phenyl)-3-methanesulfonylamino-benzamide
N-(4-Amino-phenyl)-2-trifluoromethyl-benzamide
N-(4-Amino-phenyl)-2,6-difluoro-benzamide
N-(4-Amino-phenyl)-2-chloro-benzamide
N-(4-Amino-phenyl)-2-bromo-benzamide
N-(4-Amino-phenyl)-2-nitro-benzamide
Pyrazine-2-carboxylic acid (4-amino-phenyl)-amide
5-Methyl-thiophene-2-carboxylic acid (4-amino-phenyl)-amide
Quinoline-8-carboxylic acid (4-amino-phenyl)-amide
1-Methyl-1H-pyrrole -2-carboxylic acid (4-amino-phenyl)-amide
Benzo[b]thiophene-2-carboxylic acid (4-amino-phenyl)-amide
Benzofuran-2-carboxylic acid (4-amino-phenyl)-amide
N-(4-Amino-phenyl)-isonicotinamide
Naphthalene-2-carboxylic acid (4-amino-phenyl)-amide
Naphthalene-1-carboxylic acid (4-amino-phenyl)-amide
Isoquinoline-1-carboxylic acid (4-amino-phenyl)-amide
Quinoline-2-carboxylic acid (4-amino-phenyl)-amide
3,5-Dichloro-4-ethoxy-phenylamine
4-Butoxy-3,5-dichloro-phenylamine
Isoquinoline-4-carboxylic acid (4-amino-phenyl)-amide
[1,2,3]Thiadiazole-4-carboxylic acid (4-amino-phenyl)-amide
1H-[1,2,3]Triazole-4-carboxylic acid (4-amino-phenyl)-amide
3-Bromo-thiophene-2-carboxylic acid (4-amino-phenyl)-amide
4-Benzyloxy-3,5-dichloro-phenylamine
2-(4-Amino-2,6-dichloro-phenoxy)-acetamide
(4-Amino-2,6-dichloro-phenoxy)-acetic acid methyl ester
[3-(4-Amino-phenylcarbamoyl)-phenyl]-carbamic acid ethyl ester
2-Amino-N-(4-amino-phenyl)-benzamide
Biphenyl-2-carboxylic acid (4-amino-phenyl)-amide
N-(4-Amino-phenyl)-2,3-difluoro-benzamide
N-(4-Amino-phenyl)-2,5-difluoro-benzamide
N-(4-Amino-phenyl)-2,4-difluoro-benzamide
2-Acetylamino-N-(4-amino-phenyl)-benzamide
N-(4-Amino-phenyl)-2-methanesulfonylamino-benzamide
N-(4-Amino-phenyl)-2,3,4-trifluoro-benzamide
N-(4-Amino-phenyl)-2,3,4,5,6-pentafluoro-benzamide
N-(4-Amino-phenyl)-2-methylsulfanyl-benzamide
Acetic acid 2-(4-amino-2,6-dichloro-phenoxy)-ethyl ester
N-(4-Amino-phenyl)-isophthalamic acid methyl ester
N-(4-Amino-phenyl)-3-benzyloxy-benzamide
N-(4-Amino-phenyl)-3-butoxy-benzamide
[3-(4-Amino-phenylcarbamoyl)-phenoxy]-acetic acid ethyl ester
Pyridine-2-carboxylic acid (4-amino-phenyl)-amide
Quinoline-4-carboxylic acid (4-amino-phenyl)-amide
5-Methyl-furan-2-carboxylic acid (4-amino-phenyl)-amide
5-Difluoromethyl-furan-2-carboxylic acid (4-amino-phenyl)-amide
1H-Indole-2-carboxylic acid (4-amino-phenyl)-amide
4-Methyl-[1,2,3]thiadiazole-5-carboxylic acid (4-amino-phenyl)-amide
Thiophene-3-carboxylic acid (4-amino-phenyl)-amide
5-Chloro-furan-2-carboxylic acid (4-amino-phenyl)-amide
5-Nitro-furan-2-carboxylic acid (4-amino-phenyl)-amide
N-(4-Amino-phenyl)-2-thiophen-2-yl-acetamide
3-Methyl-furan-2-carboxylic acid (4-amino-phenyl)-amide
5-Bromo-furan-2-carboxylic acid (4-amino-phenyl)-amide
4-Bromo-furan-2-carboxylic acid (4-amino-phenyl)-amide
N-(4-Amino-phenyl)-nicotinamide N-(4-Aminophenyl)-3-furancarboxamide
4-Phenyl-[1,2,3]thiadiazole-5-carboxylic acid (4-aminophenyl)-amide
Acetic acid 3-(4-amino-phenylcarbamoyl)-phenyl ester
Benzo[1,3]dioxole-4-carboxylic acid (4-amino-phenyl)-amide
N-(4-Amino-phenyl)-3-(2-dimethylamino-ethoxy)-benzamide
N-(4-Amino-phenyl)-3-trifluoromethoxy-benzamide
N-(4-Amino-phenyl)-3-(2-morpholin-4-yl-ethoxy)-benzamide
(4-Amino-phenyl)-carbamic acid hexyl ester
Furan-2-carboxylic acid (4-amino-phenyl)-amide
(4-Amino-phenyl)-carbamic acid phenyl ester
Hexanoic acid (4-amino-phenyl)-amide
N-(4-Amino-phenyl)-acrylamide
N-(4-Amino-phenyl)-2-methoxy-acetamide
4-Furan-3-yl-[1,2,3]thiadiazole-5-carboxylic acid (4-amino-phenyl)-amide
5-tert-Butyl-furan-2-carboxylic acid (4-amino-phenyl)-amide
3-Chloro-4-methanesulfinyl-phenylamine
5-Methyl-[1,2,3]thiadiazole-4-carboxylic acid (4-amino-phenyl)-amide
2-(4-Amino-2-chloro-phenyl)-ethanol
(4-Amino-2-chloro-phenyl)-carbamic acid 2-piperidin-1-yl-ethyl ester
5-Chloro-N,N-dimethyl-benzene-1,3-diamine
3-(2-Methyl-butyl)-5-trifluoromethyl-phenylamine
3-Isobutyl-5-trifluoromethyl-phenylamine
Furan-2-carboxylic acid (4-aminomethyl-phenyl)-amide
N-(4-Aminomethyl-phenyl)-2-fluoro-benzamide
[1,2,3]Thiadiazole-4-carboxylic acid (4-aminomethyl-phenyl)-amide
N-(4-Aminomethyl-phenyl)-2,6-difluoro-benzamide
Oxazole-4-carboxylic acid (4-amino-phenyl)-amide
N-(4-Amino-phenyl)-3-chloro-benzamide
N-(4-Amino-phenyl)-4-chloro-benzamide
Acetic acid 4-(4-amino-phenylcarbamoyl)-phenyl ester
N-(4-Amino-phenyl)-4-dimethylamino-benzamide
1-(4-Amino-phenyl)-3-(3,5-bis-trifluoromethyl-phenyl)-thiourea
N-(4-Amino-phenyl)-2-iodo-benzamide
N-(4-Amino-phenyl)-3-trifluoromethyl-benzamide

EXAMPLE 16

(Method 3B)

1-(4-Amino-2-chloro-phenyl)-ethanol

A 1M solution of tetrabutylammonium fluoride in tetrahydrofuran (5.7 mL) is added to [3-chloro-4-(1-hydroxyethyl)-phenyl]-carbamic acid 2-trimethylsilanyl-ethyl ester (0.5 g) and the mixture is stirred at room temperature for approximately 3.5 hours. The solution is then concentrated under reduced pressure, dissolved in a 1:1 mixture of ethyl acetate and hexanes, washed successively with water then saturated aqueous sodium chloride, and dried over anhydrous magnesium sulfate. Removal of the solvent under reduced pressure followed by chromatography over silica gel (40% ethyl acetate in hexanes is used as the eluant) provides the product as an amber oil.

EXAMPLE 17

(Method 3C)

N-(4-Amino-3-cyanophenyl)-2-fluoro-benzamide

Potassium carbonate (5.0 g) is added to a solution of N-[3-cyano-4-(2,2,2-trifluoroacetyl-amino)-phenyl]-2-fluoro-benzamide (2.5 g) in methanol (270 mL) and water (16 mL) and the mixture is refluxed overnight. After removing the solvent under reduced pressure, the residue is suspended in water and extracted with dichloromethane. The organic extracts are pooled, washed with water and then saturated aqueous sodium chloride, dried over anhydrous magnesium sulfate, filtered and concentrated under reduced pressure to provide the desired compound as a white solid.

Using the above procedure and appropriate starting materials the following compounds were prepared:
N-(4-Amino-phenyl)-2-methanesulfinyl-benzamide
N-(4-Amino-3-cyano-phenyl)-2-fluoro-benzamide
Furan-2-carboxylic acid (4-amino-3-cyano-phenyl)-amide
N-(4-Amino-3-cyano-phenyl)-acetamide
Furan-2-carboxylic acid (4-amino-3-trifluoromethyl-phenyl)-amide
N-(4-Amino-3-methoxy-phenyl)-acetamide
N-(4-Amino-3-methoxy-phenyl)-2-fluoro-benzamide
Furan-2-carboxylic acid (4-amino-3-methoxy-phenyl)-amide

EXAMPLE 17

(Method 4A)

2-Chloro-1-cyclohexyloxy-4-nitro-benzene

Cylcohexanol (2.9 g) in dimethylsulfoxide (20 mL) is added slowly to a flask containing potassium hydride (0.90 g, pre-washed three times with hexanes) under an atmosphere of argon and the solution is stirred for about 1 hour at room temperature. A solution of 3-chloro-4-fluoro-nitrobenzene (1 g) in dimethylsulfoxide (10 mL) is added and the resulting dark red colored solution is then heated for three hours to approximately 100 degrees. The reaction mixture is then cooled, diluted with diethyl ether (300 mL), and washed successively with saturated aqueous ammonium chloride, three times with water, then with saturated aqueous sodium chloride. The organic layer is then dried over anhydrous magnesium sulfate, the solvent is removed under reduced pressure, and the resulting oil is chromatographed over silica gel (5% ethyl acetate in hexanes is used as the eluant) to provide the desired product as an orange solid.

EXAMPLE 18

(Method 4C)

(2-Chloro-4-nitro-phenyl)-methyl-(1-methyl-pyrrolidin-3-yl)-amine

3-Chloro-4-fluoronitrobenzene (1.0 g) and N,N'-dimethyl-3-aminopyrrolidine (1.72 g) are combined and stirred for approximately 24 hours. The mixture is then diluted with ethyl acetate, washed twice with water and once with saturated sodium chloride, and dried over anhydrous sodium sulfate. After removal of the solvent under reduced pressure the residue is chromatographed over silica gel (pure ethyl acetate followed by pure methanol is used as the eluants) to provide the desired product as a yellow oil.

Using the above procedure and appropriate starting materials the following compounds were prepared:
(2-Chloro-4-nitro-phenyl)-dipropyl-amine
1-(2-Chloro-4-nitro-phenyl)-piperidine
1-(2-Chloro-4-nitro-phenyl)-pyrrolidine
(2-Chloro-4-nitro-phenyl)-cyclohexyl-methyl-amine
Benzyl-(2-chloro-4-nitro-phenyl)-amine
(2-Chloro-4-nitro-phenyl)-methyl-(1-methyl-piperidin-4-yl)-amine (2-Chloro-4-nitro-phenyl)-cyclohexyl-ethyl-amine
(2-Chloro-4-nitro-phenyl)-cyclohexyl-amine
(2-Chloro-4-nitro-phenyl)-methyl-(1-methyl-pyrrolidin-3-yl)-amine
(1-Benzyl-pyrrolidin-3-yl)-(2-chloro-4-nitro-phenyl)-methyl-amine
(2-Chloro-4-nitro-phenyl)-cyclopentyl-methyl-amine
1-(2-Chloro-4-nitro-phenyl)-decahydro-quinoline
Allyl-(2-chloro-4-nitro-phenyl)-cyclohexyl-amine
2-[(2-Chloro-4-nitro-phenyl)-(2-hydroxy-ethyl)-amino]-ethanol
(2-Chloro-4-nitro-phenyl)-isobutyl-methyl-amine
(2-Chloro-4-nitro-phenyl)-hexyl-methyl-amine
2-[(2-Chloro-4-nitro-phenyl)-methyl-amino]-ethanol
N-(2-Chloro-4-nitro-phenyl)-N,N',N'-trimethyl-ethane-1,2-diamine
N-(2-Chloro-4-nitro-phenyl)-N,N',N'-trimethyl-propane-1,3-diamine
(1-Benzyl-piperidin-4-yl)-(2-chloro-4-nitro-phenyl)-amine
N-(2-Chloro-4-nitro-phenyl)-N',N'-dimethyl-ethane-1,2-diamine
N-(2-Chloro-4-nitro-phenyl)-N',N'-dimethyl-propane-1,3-diamine
(2-Chloro-4-nitro-phenyl)-(2-methoxy-ethyl)-methyl-amine
(1-Benzyl-pyrrolidin-3-yl)-(2-chloro-4-nitro-phenyl)-amine
4-Piperidin-1-yl-3-trifluoromethyl-benzonitrile
4-Dimethylamino-3-trifluoromethyl-benzonitrile
4-(4-Methyl-piperazin-1-yl)-3-trifluoromethyl-benzonitrile

EXAMPLE 19

(Method 4E)

Butyl-(2-chloro-4-nitro-phenyl)thioether

A solution of 3-chloro-4-fluoro-nitrobenzene (5.0 g) and sodium sulfide (2.5 g) in N,N-dimethylformamide (30 mL) is stirred at room temperature for 1 hour and then treated with 1-iodobutane (12.6 g). The solvent is then removed under reduced pressure and the resulting residue is treated with ethyl acetate and hexanes to precipitate the inorganic salts. The solids are removed by filtration and the filtrate is reduced under reduced pressure. The resulting residue is then passed through hydrous magnesium silicate using dichloromethane as the eluent to provide the desired compound as a yellow solid.

Using the above procedure and appropriate starting materials the following compounds were prepared:
1-Butylsulfanyl-2-chloro-4-nitro-benzene
2-Chloro-1-cyclohexylsulfanyl-4-nitro-benzene
2-Chloro-1-ethylsulfanyl-4-nitro-benzene

EXAMPLE 20

(Method 4F)

(4-Chloro-5-methoxy-2-nitro-phenyl)-dimethyl-amine

To a solution of trifluoro-methanesulfonic acid 4-chloro-5-methoxy-2-nitro-phenyl ester (1.0 g) in tetrahydrofuran (2.0 mL) is added dimethylamine (4.0 mL of a 40% aqueous solution) and the mixture is stirred at room temperature for approximately 15 hours. The solution is then concentrated under reduced pressure and the residue is dissolved in ethyl acetate and then washed with water. The aqueous layer is extracted once with ethyl acetate and the combined organic layers are washed with saturated aqueous sodium chloride and dried over anhydrous sodium sulfate. The solvent is removed by evaporation under reduced pressure and the residue is triturated with hexanes to provide the desired product as a colorless solid.

Using the above procedure and appropriate starting materials the following compounds were prepared:
(4-Chloro-2-nitro-phenyl)-dimethyl-amine
4-(4-Chloro-5-methoxy-2-nitro-phenyl)-morpholine
(4-Chloro-5-methoxy-2-nitro-phenyl)-dimethyl-amine
1-(4-Chloro-5-methoxy-2-nitro-phenyl)-piperidine
1-(4-Chloro-5-methoxy-2-nitro-phenyl)-pyrrolidine
Benzyl-(4-chloro-5-methoxy-2-nitro-phenyl)-amine
(2-Chloro-6-nitro-phenyl)-dimethyl-amine

EXAMPLE 21

(Method 4G)

(2-Chloro-4-nitro-phenyl)-methyl-phenyl-amine n-Butyl lithium (12.3 mL of a 2.5 M solution in hexanes) is added dropwise to a solution of N-methyl aniline (3.0 g) in tetrahydrofuran (75 mL) at 0° C. The mixture is allowed to warm slowly to room temperature and is then re-cooled to 0° C. and added by cannula to a solution of 3-chloro-4-fluoronitrobenzene (4.9 g) in tetrahydrofuran (35 mL) that is kept at −78° C. Following the addition, the reaction mixture is permitted to warm to room temperature over the course of 1 hour, and is then concentrated under reduced pressure, quenched by addition of saturated aqueous ammonium chloride, and extracted three times with ethyl acetate. The pooled organic layers are washed three times with 5% aqueous hydrochloric acid, once with water, once with saturated aqueous sodium bicarbonate, once with saturated aqueous sodium chloride, and then dried over anhydrous magnesium sulfate. Following removal of the solvent under reduced pressure the residue is chromatographed over silica gel (5% diethyl ether in hexanes is used as the eluant) to provide the desired product as a clear colorless oil.

EXAMPLE 22

(Method 4H)

2,6-Dichloro-4-nitrophenol 3,4,5-Trichloronitrobenzene (14.86 g) is added to a solution of potassium phenoxide (8.66 g) in diethylene glycol (66 mL) and the mixture is heated to 160° C. for approximately 15 hours. The resulting dark brown solution is cooled to room temperature, poured onto 100 mL cold water, and extracted twice with diethyl ether. The pooled organic extracts are washed with water, 10% aqueous sodium hydroxide, and then dried over anhydrous magnesium sulfate. Following removal of the solvent under reduced pressure the resulting oil is distilled in a Kugelrohr apparatus to provide a yellow oil that solidifies on standing. Recrystallization from ethanol-water provides the desired product as a pale yellow solid.

EXAMPLE 23

(Method 5A)

(3,5-Dichloro-4-ethoxy-phenyl)-carbamic Acid Tert-butyl Ester

To a solution of (3,5-dichloro-4-hydroxy-phenyl)-carbamic acid tert-butyl ester (1.0 g) and potassium carbonate (1.0 g) in acetone (18 mL) is added ethyl iodide (0.36 mL) and the mixture is stirred for approximately 15 hours at room temperature. The solution is then filtered, concentrated under reduced pressure, and partitioned between ethyl acetate and water. The separated aqueous layer is further extracted twice with ethyl acetate, and the pooled organic extracts are washed successively with 10% aqueous sodium hydroxide, with water, and then dried over anhydrous sodium sulfate. Evaporation of the solvent under reduced pressure gave the desired product as a tan solid.

Using the above procedure and appropriate starting materials the following compounds were prepared:
(3,5-Dichloro-4-ethoxy-phenyl)-carbamic acid tert-butyl ester
(4-Butoxy-3,5-dichloro-phenyl)-carbamic acid tert-butyl ester
(4-Benzyloxy-3,5-dichloro-phenyl)-carbamic acid tert-butyl ester
(4-Carbamoylmethoxy-3,5-dichloro-phenyl)-carbamic acid tert-butyl ester
[3,5-Dichloro-4-(2-nitrilo-ethoxy)-phenyl]-carbamic acid tert-butyl ester
(4-tert-Butoxycarbonylamino-2,6-dichloro-phenoxy)-acetic acid methyl ester
3-Butoxy-benzoic acid methyl ester
3-tert-Butoxycarbonylmethoxy-benzoic acid methyl ester
3-Carbamoylmethoxy-benzoic acid methyl ester
[4-(3-Carbamoylmethoxy-benzoylamino)-phenyl]-carbamic acid tert-butyl ester
{4-[3-(2-Chloro-ethoxy)-benzoylamino]-phenyl}-carbamic acid tert-butyl ester

EXAMPLE 24

(Method 5C)

(2,6-Dichloro-4-nitro-phenoxy)-acetic acid tert-butyl ester

To a solution of 2,6-dichloro-4-nitrophenol (2.5 g) and potassium carbonate (3.3 g) in dimethyl-formamide (50 mL) is added tert-butyl-bromoacetate (10 mL) and the mixture is stirred at room temperature for two days. The solution is then poured into 500 mL water, extracted three times with hexanes, and the pooled organic extracts are washed with saturated aqueous ammonium chloride and then dried over anhydrous magnesium sulfate. Evaporation of the solvent under reduced pressure followed by trituration of the resulting oil with hexanes provides the desired product as a white solid.

Using the above procedure and starting materials the following compounds were prepared:
3-Dimethylamino-1-(4-nitro-phenyl)-propenone
2-Chloro-1-isopropoxy-4-nitro-benzene
1,3-Dichloro-2-methoxy-4-methyl-5-nitro-benzene
1-Chloro-4-ethoxy-2-methoxy-5-nitro-benzene
1-Butoxy-4-chloro-5-methoxy-2-nitro-benzene
1-Chloro-2-methoxy-5-nitro-4-(phenylmethoxy)benzene (CA name)
1-Chloro-4-methoxy-5-nitro-2-(phenylmethoxy)benzene (CA name)
(2,6-Dichloro-4-nitro-phenoxy)-acetic acid tert-butyl ester
(2,6-Dichloro-4-nitro-phenoxy)-acetonitrile
1-Chloro-4-methoxy-2-methyl-5-nitro-benzene
2-(4-Chloro-5-methoxy-2-nitro-phenoxy)-acetamide
2-(2-Chloro-5-methoxy-4-nitro-phenoxy)-acetamide
(4-Chloro-5-methoxy-2-nitro-phenoxy)-acetonitrile
(2-Chloro-5-methoxy-4-nitro-phenoxy)-acetonitrile
4-(2-Chloro-5-methoxy-4-nitro-phenoxy)-butyronitrile
2-(4-Chloro-5-methoxy-2-nitro-phenoxy)-ethanol
2-(2-Chloro-5-methoxy-4-nitro-phenoxy)-ethanol
(2-Chloro-5-methoxy-4-nitro-phenoxy)-acetic acid tert-butyl ester
(2-Chloro-5-methoxy-4-nitro-phenoxy)-acetic acid methyl ester
(4-Chloro-5-methoxy-2-nitro-phenoxy)-acetic acid methyl ester
(4-Chloro-5-methoxy-2-nitro-phenoxy)-acetic acid tert-butyl ester
(2-Chloro-4-nitro-phenoxy)-acetonitrile
1-Butoxy-2-chloro-4-nitro-benzene
2-Chloro-4-nitro-1-(2,2,2-trifluoro-ethoxy)-benzene
2-Chloro-4-nitro-1-propoxy-benzene
2-Chloro-1-ethoxy-4-nitro-benzene
1,3-Diiodo-2,4-dimethoxy-5-nitro-benzene
1,3-Dibromo-2,4-dimethoxy-5-nitro-benzene
3-Chloro-2,4-dimethoxy-nitrobenzene

EXAMPLE 25

(Method 5E)

[3,5-Dichloro-4-(2-hydroxy-ethoxy)-phenyl]-carbamic Acid Tert-butyl Ester

To a solution of (3,5-dichloro-4-hydroxy-phenyl)-carbamic acid tert-butyl ester (1.0 g) and potassium carbonate (0.55 g) in toluene (20 mL) is added ethylene carbonate (1.6 g) and the mixture is heated to reflux for 3 hours. To the cooled reaction mixture is added 2.5 M aqueous sodium hydroxide (50 mL), and the separated organic layer is then washed successively with water, then saturated aqueous sodium chloride, and then dried over anhydrous sodium sulfate. The solvent is then removed by evaporation under reduced pressure and the resulting residue is chromatographed over silica gel (30% ethyl acetate in hexanes is used as the eluant) to provide the desired product as a white foam.

EXAMPLE 26

(Method 6)

3-(2-Chloro-4-nitro-phenoxy)-1-methyl-pyrrolidine

To a solution of 2-chloro-4-nitrophenol (2.0 g) in tetrahydrofuran (60 mL) is added 1-methyl-3-pyrrolidinol (2.3 g), triphenyl phosphine (6.0 g), and diethylazo-dicarboxylate (3.6 mL) and the mixture is stirred at room temperature under an atmosphere of argon for 1.5 hours. The solution is then concentrated under reduced pressure, diluted with ethyl acetate, washed successively with 10% aqueous sodium hydroxide, water, saturated aqueous sodium chloride, and dried over anhydrous magnesium sulfate. The solvent is removed by evaporation under reduced pressure and the residue is chromatographed over silica gel (ethyl acetate then 10% methanol in dichloromethane is used as the eluant). Pooled product fractions are then recrystallized from hexanes to provide the desired product as a yellow solid.

Using the above procedure and appropriate starting materials the following compounds were prepared:
4-(2-Chloro-4-nitro-phenoxy)-1-methyl-piperidine
3-(2-Chloro-4-nitro-phenoxy)-1-methyl-pyrrolidine
[2-(2-Chloro-4-nitro-phenoxy)-ethyl]-dimethyl-amine
[3-(2-Chloro-4-nitro-phenoxy)-propyl]-dimethyl-amine

EXAMPLE 27

(Method 7A)

2-Chloro-3-methoxy-6-nitro-phenol and 2,4-Dichloro-3-methoxy-6-nitro-phenol

To a flask containing 3-methoxy-6-nitro-phenol (0.5 g) is added aqueous sodium hypochlorite (5.25% aqueous solution, 21 mL) and the mixture is stirred at room temperature for approximately 24 hours. The mixture is then cooled in an ice-bath, acidified by addition of concentrated hydrochloric acid, then extracted twice with ethyl acetate. These organic extracts are dried over anhydrous magnesium sulfate, the solvent is removed by evaporation under reduced pressure, and the residue is chromatographed over silca gel (15% acetone in hexanes is used as the eluant) to provide both the mono- and di-chlorinated products as yellow solids.

Using the above procedure and appropriate starting materials the following compounds were prepared:
3-Chloro-2-hydroxy-4-methoxy-nitrobenzene
3,5-Dichloro-2-hydroxy-4-methoxy-nitrobenzene

EXAMPLE 28

(Method 7B)

2,4-Dichloro-3-methyl-6-nitro-phenol

To a solution of 3-methyl-4-nitro-phenol (5.0 g) in water (150 mL) is added aqueous sodium hypochlorite (5.25% aqueous solution, 230 mL) and the mixture is stirred at room temperature for approximately 15 hours. Additional aqueous sodium hypochlorite (5.25% aqueous solution, 230 mL) is added and the mixture is permitted to stir at room temperature for 2.5 days. The mixture is then cooled in an ice-bath, acidified by addition of concentrated hydrochloric acid, then extracted twice with ethyl acetate. These organic extracts are dried over anhydrous magnesium sulfate, the solvent is removed by evaporation under reduced pressure, and the residue is chromatographed over silca gel (ethyl acetate is used as the eluant) to provide the desired product as a yellow solid. An analytically pure sample is obtained by a single recrystallization from chloroform.

EXAMPLE 29

(Method 7C)

1-Bromo-2,4-dimethoxy-5-nitro-benzene

To a solution of 2,4-dimethoxy-nitrobenzene (0.50 g) in chloroform (3 mL) is added dropwise a solution of bromine (0.23 g) in chloroform (1 mL) and the mixture is allowed to stir at room temperature for approximately 15 hours. Additional bromine (0.15 g) in chloroform (1 mL) is added and the reaction is stirred for an additional 4 hours. The mixture is then poured onto 5% aqueous sodium bisulfite and then extracted with chloroform. Pooled organic extracts are then washed successively with 5% aqueous sodium bisulfite then saturated sodium chloride, and then dried over anhydrous sodium sulfate. Removal of the solvent under reduced pressure and recrystallization of the residue from toluene provides the desired product as a yellow solid.

EXAMPLE 30

(Method 7D)

2,4-Dibromo-3-methoxy-6-nitro-phenol

To a solution of 5-methoxy-2-nitro-phenol (0.25 g) and silver trifluoroacetate (0.49 g) in glacial acetic acid (3 mL) is added dropwise a solution of bromine (1.42 g) in glacial acetic acid (3 mL) and the mixture is stirred at room temperature for approximately 24 hours. The solution is then partitioned between ethyl acetate and water, and the organic layer is washed successively three times with 5% aqueous sodium bisulfite, three times with saturated aqueous sodium bicarbonate, and once with saturated aqueous sodium chloride. The organic layer is then dried over anhydrous magnesium sulfate and the solvent is removed under reduced pressure. The residue is chromatographed over silica gel (20% ethyl acetate in hexanes is used as the eluant) then recrystallized from chloroform to provide the desired dibrominated product as an orange solid.

EXAMPLE 31

(Method 7E)

1-Iodo-2,4-dimethoxy-5-nitro-benzene

To a solution of 2,4-dimethoxy-nitrobenzene (1.0 g) in glacial acetic acid (30 mL) is added benzyltrimethylammonium dichloroiodate (1.90 g) and anhydrous zinc chloride (1.0 g) and the mixture is stirred at room temperature under an atmosphere of argon. Additional benzyltrimethylammonium dichloroiodate (0.4 g) is added after 5 hours and again after 24 hours. Additional zinc chloride (0.5 g) and glacial acetic acid (15 mL) is added after 24 hours. The mixture is permitted to stir at room temperature for 3 days and is then filtered, diluted with 5% aqueous sodium bisulfite, and extracted three times with ethyl acetate. These pooled organic extracts are washed successively with 5% aqueous sodium bisulfite, saturated aqueous sodium chloride, then dried over anhydrous magnesium sulfate. After removal of the solvent under reduced pressure the residue is triturated with hexanes to provide the desired product as a pale yellow solid.

EXAMPLE 32

(Method 7F)

2,4-Diiodo-3-methoxy-6-nitro-phenol

To a solution of 5-methoxy-2-nitro-phenol (0.25 g) in dichloromethane (15 mL) and methanol (6 mL) is added benzyltrimethylammonium dichloroiodate (1.08 g) and sodium bicarbonate (0.85 g) and the mixture is allowed to stir at room temperature for 24 hours. The solution is then filtered, the filtrate is concentrated under reduced pressure, the residue is dissolved in ethyl acetate and then washed successively with 5% aqueous sodium bicarbonate, 5% aqueous sodium bisulfite, and saturated aqueous sodium chloride. After drying over anhydrous magnesium sulfate the solvent is removed by evaporation under reduced pressure and the residue is recrystallized from toluene to provide the desired product as yellow needles.

EXAMPLE 33

(Method 7G)

1-Fluoro-2,4-dimethoxy-5-nitro-benzene

To a solution of 2,4-dimethoxy-nitrobenzene (1.0 g) in tetrachloroethane (10 mL) is added 3,5-dichloro-1-fluoropyridinium triflate (85%, 5.07 g) and the mixture is heated to 120° C. for 5 hours. Additional 3,5-dichloro-1-fluoropyridinium triflate (85%, 0.25 g) is added and heating is continued for 1 hour. The solution is then cooled to room temperature and passed over a column of silica gel (hexanes followed by 30% ethyl acetate in hexanes is used as the eluant). Product containing fractions are combined, evaporated under reduced pressure, and the residue is crystallized from hexanes to provide the desired product as a tan solid.

EXAMPLE 34

(Method 8)

3-Chloro-4-trifluoromethyl-nitrobenzene

A solution of 3-chloro-4-iodo-nitrobenzene (2.26 g), trimethyl(trifluoromethyl)silane (5.68 g), copper(I) iodide (2.28 g), and potassium fluoride (0.56 g) in N,N-dimethylformamide (8 mL) is heated in a sealed tube to 80° C. for 40 hours. The solution is then cooled, diluted with diethyl ether, filtered through diatomaceous earth, and the filtrate is washed successively with water, saturated aqueous sodium chloride, and then dried over anhydrous sodium sulfate. The solvent is removed under reduced pressure and the residue is chromatographed over silica gel (1% diethyl ether in hexanes followed by 10% ethyl acetate in hexanes is used as the eluant) to provided the desired product as a colorless oil.

EXAMPLE 35

(Method 9)

(3-Chloro-4-methanesulfinyl-phenyl)-carbamic Acid Tert-butyl Ester

To a solution of (3-chloro-4-thiomethyl-phenyl)-carbamic acid tert-butyl ester (0.89 g) in dichloromethane (15 mL) at 0° C. is added a solution of dimethyldioxirane (0.11 M in acetone, 34 mL) and the mixture is stirred at 0° C. for 1 hour. The solvent is removed under reduced pressure and the residue is dissolved in dichloromethane, washed with saturated aqueous sodium chloride, and then dried over anhydrous magnesium sulfate. Removal of the solvent under reduced pressure gave the desired product as an orange foam.

EXAMPLE 36

(Method 9B)

[4-(2-Methylsulfinyl-benzoylamino)-phenyl]-carbamic Acid Tert-butyl Ester

To a solution of 2-methylsulfanyl-N-[4-(2,2,2-trifluoro-acetylamino)-phenyl]-benzamide (234 mg) is added a saturated solution of sodium periodate (5 mL) and the mixture is stirred for 12 hours. The purple mixture is poured into water, extracted with ethyl acetate, dried over anhydrous potassium carbonate and evaporated to yield a red solid, 101 mg.

Using the above procedure and appropriate starting materials the following compounds were prepared:
[4-(2-Methanesulfinyl-benzoylamino)-phenyl]-carbamic acid tert-butyl ester
2-Methanesulfinyl-N-[4-(2,2,2-trifluoro-acetylamino)-phenyl]-benzamide

EXAMPLE 37

(Method 10)

(3-Chloro-4-methanesulfonyl-phenyl)-carbamic Acid Tert-butyl Ester

To a solution of (3-chloro-4-thiomethyl-phenyl)-carbamic acid tert-butyl ester (0.90 g) in dichloromethane (30 mL) at 0° C. is added a solution of dimethyldioxirane (0.11 M in acetone, 80 mL) and the mixture is stirred at 0° C. for 1 hour. The solvent is removed under reduced pressure and the residue is dissolved in dichloromethane, washed with saturated aqueous sodium chloride, and then dried over anhydrous magnesium sulfate. Removal of the solvent under reduced pressure gives the desired product as an orange foam.

EXAMPLE 38

(Method 11)

3-Chloro-4-vinyl-phenylamine

To a deoxygenated solution of 3-chloro-4-iodo-aniline (6.95 g), triphenyl arsine (0.67 g), and tris (dibenzylideneacetone)palladium(O) (0.50 g) in tetrahydrofuran (120 mL) at 50° C. is added tributylvinyltin (10 g) and the mixture is stirred for approximately 15 hours at 50° C. under an atmosphere of argon. The reaction is then cooled, filtered through diatomaceous earth, and the filtrate is evaporated to dryness under reduced pressure. The residue is dissolved in hexanes and then extracted three times with 5% aqueous hydrochloric acid. These aqueous acidic extracts are then basified with solid potassium carbonate and extracted three times with ethyl acetate. These pooled organic extracts are then washed with saturated aqueous sodium chloride, dried over anhydrous magnesium sulfate, and the solvent is removed under reduced pressure. The resulting residue is chromatographed over silica gel (hexanes and then 10% ethyl acetate in hexanes is used as the eluant) to provide the desired product as an amber oil.

EXAMPLE 39

(Method 12)

[3-Chloro-4-(1-hydroxy-ethyl)-phenyl]-carbamic Acid 2-trimethylsilanyl-ethyl Ester (3-Chloro-4-vinyl-phenyl)-carbamic acid 2-trimethylsilanyl-ethyl ester (2.6 g) is added to a solution of mercuric acetate (3.48 g) in water (7 mL) and tetrahydrofuran (5.25 mL) and the mixture is stirred for approximately 15 hours. 3N Aqueous sodium hydroxide (8.7 mL) and a 0.5 M solution of sodium borohydride in 3N aqueous sodium hydroxide (8.7 mL) are then added and stirring is continued for 6 hours. The solution is then saturated with sodium chloride and extracted with ethyl acetate. These organic extracts are then washed with saturated aqueous sodium chloride and dried over anhydrous sodium sulfate. Following removal of the solvent under reduced pressure the residue is chromatographed over silica gel (20% ethyl acetate in hexanes is used as the eluant) to provide the desired product as a white solid.

EXAMPLE 40

(Method 13)

[3-Chloro-4-(2-hydroxy-ethyl)-phenyl]-carbamic Acid Tert-butyl Ester

To a stirring suspension of sodium borohydride (0.45 g) in tetrahydrofuran (13 mL) at 0° C. is added glacial acetic acid (0.75 mL) and the mixture is stirred at 0° C. for 1 hour. The solution is then warmed to room temperature and (3-chloro-4-vinyl-phenyl)-carbamic acid 2-trimethylsilanyl-ethyl ester (1.0 g) is added. The reaction is stirred at room temperature for approximately 15 hours and then heated to reflux for approximately 20 hours. The mixture is then cooled and solutions of 5 N aqueous sodium hydroxide (0.80 mL) and 30% aqueous hydrogen peroxide (0.56 mL) are added. After stirring for an additional 15 hours the layers are separated, the aqueous layer is extracted three times with diethyl ether, and these organic extracts are dried over anhydrous magnesium sulfate. Following removal of the solvent under reduced pressure the residue is chromatographed over silica gel (40% ethyl acetate in hexanes is used as the eluant) to provide the desired product as an amber oil.

EXAMPLE 41

(Method 14)

[4-(1-Azido-ethyl)-3-chloro-phenyl]-carbamic Acid 2-trimethylsilanyl-ethyl Ester To a solution of [3-chloro-4-(1-hydroxy-ethyl)-phenyl]-carbamic acid 2-trimethylsilanyl-ethyl ester (1.25 g) in tetrahydrofuran (20 mL) at 0° C. under an atmosphere of argon is added triphenyl-phosphine (2.6 g), hydrazoic acid (approximately 2.5 molar equivalents in dichloromethane, prepared by the method of Fieser and Fieser, *Reagents for Organic Synthesis,* Vol. 1, pg. 446; Wiley, New York) and diethyl azodicarboxylate (1.72 g). After approximately 10 minutes the solvent is removed under reduced pressure and the residue is chromatographed over silica gel (5% ethyl acetate in hexanes is used as the eluant) to provide the desired product as a colorless oil.

EXAMPLE 42

(Method 15)

[3-Chloro-4-(3-dimethylamino-prop-1-ynyl)-phenyl]-carbamic Acid Tert-butyl Ester To a deoxygenated solution of (3-chloro-4-iodo-phenyl)-carbamic acid tert-butyl ester (10.0 g) in triethylamine (120 ml) is added 1-dimethylamino-2-propyne (2.82 g), bis(triphenyl-phosphine)palladium(II) chloride (0.4 g), and cuprous iodide (0.054 g). The mixture is stirred at room temperature under an atmosphere of argon for approximately 6 hours and is then heated briefly (ca. 10 minutes) to 60° C. The reaction mixture is then cooled, filtered through diatomaceous earth, and the solvent is removed by evaporation under reduced pressure. The residue is dissolved in ethyl acetate, washed three times with water, once with saturated aqueous sodium chloride, and dried over anhydrous magnesium sulfate. The solvent is removed by evaporation under reduced pressure, and the residue is chromatographed over silica gel (80% ethyl acetate in hexanes is used as the eluant) to give the purified product as an amber oil that solidified on standing.

Using the above procedure and appropriate starting materials the following compounds were prepared:
[3-Chloro-4-(3-dimethylamino-prop-1-ynyl)-phenyl]-carbamic acid tert-butyl ester
[3-(4-Methoxy-phenyl)-prop-2-ynyl]-dimethyl-amine
4-(3-Dimethylamino-prop-1-ynyl)-benzonitrile
Dimethyl-[3-(4-nitro-phenyl)-prop-2-ynyl]-amine

EXAMPLE 43

(Method 16)

[3-Chloro-4-(3-dimethylamino-acryloyl)-phenyl]-carbamic Acid Tert-butyl Ester

To an ice cold solution of [3-chloro-4-(3-dimethylamino-prop-1-ynyl)-phenyl]-carbamic acid tert-butyl ester (4.0 g) in dichloromethane (30 ml) is added in small portions 3-chloroperoxybenzoic acid (2.34 g). After the reaction is stirred at 0° C. for 20 minutes, the mixture is passed over twenty weight equivalents of basic alumina (Brockmann Grade I, 150 mesh) and the N-oxide is eluted using a solution of 5% methanol in dichloromethane. All fractions containing the desired amine N-oxide were combined and evaporated to near dryness under reduced pressure. The residue is treated successively three times with small portions of methanol (ca. 50 ml) followed by evaporation to near dryness under reduced pressure, and the volume of the solution is adjusted to 250 mL by addition of methanol. The methanolic solution of the N-oxide is then heated to reflux for approximately 15 hours, then cooled, and the solvent is evaporated to dryness under reduced pressure. The residue is purified by chromatography over silica gel (80% ethyl acetate in hexanes is used as the eluant) to give the desired product as a pale yellow solid.

EXAMPLE 44

(Method 17)

(3-Chloro-4-isoxazol-5-yl-phenyl)-carbamic Acid Tert-butyl Ester

A solution of [3-chloro-4-(3-dimethylamino-acryloyl)-phenyl]-carbamic acid tert-butyl ester (270 mg) in dioxane (3 ml) is treated with hydroxylamine hydrochloride (122 mg) and the mixture is stirred at room temperature for 10 days. The mixture is diluted with ethyl acetate, washed successively with water, 5% aqueous sodium bicarbonate, saturated aqueous sodium chloride, and then dried over anhydrous magnesium sulfate. The solvent is removed by evaporation under reduced pressure and the resulting residue is chromatographed over silica gel (33% ethyl acetate in hexanes is used as the eluant) to provide the desired product as a colorless solid.

EXAMPLE 45

(Method 18)

[3-Chloro-4-(1H-pyrazol-3-yl)-phenyl]-carbamic acid tert-butyl ester

A solution of [3-chloro-4-(3-dimethylamino-acryloyl)-phenyl]-carbamic acid tert-butyl ester (250 mg) in ethanol (1.25 ml) is treated with hydrazine hydrate (0.25 ml) and the mixture is stirred at room temperature for 3 hours. The mixture is then diluted with 30 mL of diethyl ether, washed three times with water, once with saturated aqueous sodium chloride, and dried over anhydrous magnesium sulfate. The solvent is removed by evaporation under reduced pressure and the resulting residue is chromatographed over silica gel (67% ethyl acetate in hexanes is used as the eluant) to provide the desired product as an oil.

EXAMPLE 46

(Method 19A)

N-(2-Chloro-4-nitrophenyl)-2-thiomorpholino-4-yl-acetamide

To a solution N-(chloroacetyl)-2-chloro-4-nitroaniline (3.80 g) in tetrahydrofuran (50 mL) is added thiomorpholine (10 mL) and the solution allowed to stand for 1 hour. This reaction mixture is poured into water a pale yellow solid is collected and then recrystallized from hot 2-propanol to give a pale yellow crystalline solid.

Using the above procedure and appropriate starting materials the following compounds were prepared:
(4-{2-[Bis-(2-hydroxy-ethyl)-amino]-acetylamino}-phenyl)-carbamic acid tert-butyl ester
[4-(2-Dimethylamino-acetylamino)-phenyl]-carbamic acid tert-butyl ester
{4-[3-(2-Dimethylamino-ethoxy)-benzoylamino]-phenyl}-carbamic acid tert-butyl ester
{4-[3-(2-Morpholin-4-yl-ethoxy)-benzoylamino]-phenyl)-carbamic acid tert-butyl ester
N-(2-Chloro-4-nitro-phenyl)-2-dimethylamino-acetamide
N-(2-Chloro-4-nitro-phenyl)-2-piperidin-1-yl-acetamide
N-(2-Chloro-4-nitro-phenyl)-2-morpholin-4-yl-acetamide
N-(2-Chloro-4-nitro-phenyl)-2-dipropylamino-acetamide
N-(2-Chloro-4-nitro-phenyl)-2-thiomorpholin-4-yl-acetamide
N-(2-Chloro-4-nitro-phenyl)-2-diethylamino-acetamide
N-(2-Chloro-4-nitro-phenyl)-2-pyrrolidin-1-yl-acetamide
2-Azepan-1-yl-N-(2-chloro-4-nitro-phenyl)-acetamide
N-(2-Chloro-4-nitro-phenyl)-2-(2-methyl-piperidin-1-yl)-acetamide
N-(2-Chloro-4-nitro-phenyl)-2-(3-methyl-piperidin-1-yl)-acetamide
N-(2-Chloro-4-nitro-phenyl)-2-(4-methyl-piperidin-1-yl)-acetamide

EXAMPLE 47

(Method 19B)

N-(2-Chloro-4-nitrophenyl)-2-(2-dimethylaminoethylsulfanyl)acetamide

To a solution of N-(chloroacetyl)-2-chloro-4-nitroaniline (3.01 g) in N,N-dimethylformamide (100 mL) is added powdered sodium carbonate (6.0 g) and 2-dimethylaminoethanethiol hydrochloride (6.0 g). The mixture is stirred for 1 hour at 25° C., poured into water and extracted into ethyl acetate. The ethyl acetate solution is dried over anhydrous potassium carbonate and concentrated under reduced pressure to give an oil. The oil is crystallized from toluene-hexanes (3:1) to yield a pale yellow crystalline solid.

EXAMPLE 48

(Method 20)

(4-tert-butoxycarbonylamino-2-chloro-phenyl)-carbamic Acid 2-piperidin-1-yl-ethyl Ester To a suspension of 1,1-carbonyl-di-(1,2,4)-triazole (4.0 g) in dichloromethane (40 mL) is added a solution of (4-amino-3-chloro-phenyl) carbamic acid tert-butyl ester (5.0 g) in dichloromethane (45 mL) dropwise over 20 minutes. The reaction is stirred at room temperature for 30 minutes at which point a precipitate forms. To this mixture is added piperidineethanol (6.6 mL) and tetra-hydrofuran (20 mL) is added to maintain homogeneity. After heating at reflux overnight the reaction is cooled and then poured into water, the organic layer separated and then washed with saturated aqueous sodium chloride. The solution is dried over anhydrous sodium sulfate, filtered and concentrated under reduced pressure to a crude oil that is purified by chromatography over silica gel (5% methanol in dichloromethane is used as the eluant) to give the desired product as a white foam.

EXAMPLE 49

5-Phenyl-[1,2,3]thiadiazole-4-carboxylic Acid Methyl Ester

A solution of ethyl benzoylacetate (1.1 g) in acetonitrile (10 mL) is treated with 4-methylbenzenesulfonyl azide (1.3 g) and triethylamine (1.6 g). After stirring overnight at room temperature, the reaction is concentrated under reduced pressure and the resulting crude product is dissolved in ethyl acetate and washed with 1N sodium hydroxide. The organic layer is then dried over anhydrous magnesium sulfate, filtered and concentrated under reduced pressure to yield a yellow oil. This oil is taken into dichloromethane and filtered through a pad of hydrous magnesium silicate, eluting with dichloromethane to give the partially purified diazoketone as a colorless oil. A sample of the diazoketone from above (1.2 g) is dissolved in toluene (25 mL) and treated with 2,4-bis(4-methoxyphenyl)-1,3-dithia-2,4-diphosphetane 2,4-disulfide (2.8 g) and the reaction is heated to reflux. After 3 hours, the reaction is cooled to room temperature, loaded onto a pad of silica gel and eluted with dichloromethane. After removing the solvent under reduced pressure, the resulting oil is purified by chromatography over silica gel (30% diethyl ether in petroleum ether is used as the eluant) and then recrystallized from hexanes to give the desired product as pale yellow needles.

Using the above procedure and appropriate starting materials the following compound was prepared:
5-Phenyl-[1,2,3]thiadiazole-4-carboxylic acid ethyl ester
5-Methyl-[1,2,3]thiadiazole-4-carboxylic acid methyl ester

EXAMPLE 50

Ethyl Benzoylacetate Semicarbazide

Ethyl benzoylacetate (5.0 g) is dissolved in methanol (10 mL) and added rapidly to a hot solution of semicarbazide hydrochloride (29 g) in water (130 mL). To this is added pyridine (4.1 g) and after heating to reflux for 5 minutes, the reaction mixture is cooled to −20° C. overnight. The resulting solid semicarbazone is collected by filtration, washed with water and then diethyl ether to give the desired product as white crystals.

Using the above procedure and appropriate starting materials the following compound was prepared:
Ethyl (Z)-3-[(aminocarbonyl)hydrazono]-4,4,4-trifluorobutanoate
3-[(Z)-2-(Aminocarbonyl)hydrazono]-3-phenylpropanoic acid ethyl ester
3-[(E)-2-(Aminocarbonyl)hydrazono]-3-(3-furyl)propanoic acid ethyl ster

EXAMPLE 51

5-Phenyl-[1,2,3]thiadiazole-5-carboxylic Acid Ethyl Ester

A solution of ethyl benzoylacetate semicarbazone (2.5 g) in neat thionyl chloride (5 mL) is stirred at 0° C. for 1 hour. Dichloromethane is then added (25 mL), the excess thionyl chloride is destroyed slowly with saturated aqueous sodium bicarbonate. The precipitate which forms on quenching is removed by filtration and the filtrate is extracted with dichloromethane. Pooled organic extracts are dried over anhydrous magnesium sulfate, filtered and concentrated under reduced pressure. Chromatography over silica gel (50% hexanes in dichloromethane is used as the eluant) affords the desired product as a colorless oil.

Using the above procedure and appropriate starting materials the following compounds were prepared:
4-Methyl-[1,2,3]thiadiazole-5-carboxylic acid methyl ester
4-Phenyl-[1,2,3]thiadiazole-5-carboxylic acid ethyl ester
4-Furan-3-yl-[1,2,3]thiadiazole-5-carboxylic acid ethyl ester

EXAMPLE 52

4-Methyl-[1,2,3]thiadiazole-5-carboxylic Acid

4-Methyl-[1,2,3]thiadiazole-5-carboxylic acid methyl ester (1.7 g) is dissolved in methanol (15 mL) and treated with 1N sodium hydroxide (16 mL). After stirring at room temperature for 1 hour, the reaction is treated with concentrated hydrochloric acid (1.5 mL) and concentrated under reduced pressure. The resulting turbid aqueous layer is extracted twice with diethyl ether and the pooled organic layers are dried over anhydrous magnesium sulfate, filtered and concentrated under reduced pressure to give the desired compound as a white powder.

Using the above procedure and appropriate starting materials the following compounds were prepared:
3-Ethoxycarbonylmethoxy-benzoic acid
5-Furan-3-yl-[1,2,3]thiadiazole-4-carboxylic acid
Thiazole-4-carboxylic acid
4-Methyl-[,2,3]thiadiazole-5-carboxylic acid
5-Methyl-[1,2,3]thiadiazole-4-carboxylic acid

EXAMPLE 53

(Method 25)

Trifluoro-methanesulfonic Acid 4-chloro-5-methoxy-2-nitro-phenyl Ester

To a solution of 4-chloro-5-methoxy-2-nitro-phenol (6.5 g) in dichloromethane (150 mL) at 0° C. under an atmosphere of argon is added triethylamine (10 g) and then a solution of trifluoro-methanesulfonic anhydride (13.5 g) in dichloromethane (30 mL). The solution is stirred at 0° C. for 10 minutes, and is then diluted with dichloromethane and washed successively with saturated aqueous sodium bicarbonate and saturated aqueous sodium chloride. After drying over anhydrous sodium sulfate the solvent is removed by evaporation under reduced pressure and the residue is dissolved in a solution of 20% dichloromethane in hexanes and passed through a short column of hydrous magnesium silicate (20% dichloromethane in hexanes is used as the eluant). Product containing fractions are pooled and the solvents removed by evaporation under reduced pressure to give the desired product as a yellow oil.

Using the above procedure and appropriate starting materials the following compounds were prepared:
Trifluoro-methanesulfonic acid 4-chloro-5-methoxy-2-nitro-phenyl ester
Trifluoro-methanesulfonic acid 4-chloro-2-nitro-phenyl ester
Trifluoro-methanesulfonic acid 2-chloro-6-nitro-phenyl ester

EXAMPLE 54

(Method 26)

[4-(3-Dimethylamino-benzoylamino)-phenyl]-carbamic Acid T-butyl Ester

A solution of [4-(3-amino-benzoylamino)-phenyl]-carbamic acid t-butyl ester (505 mg), sodium cyanoborohydride (250 mg), acetic acid (3 drops) and 40% aqueous formaldehyde (4 mL) in 1:2 tetrahydrofuran-methanol (15 mL) is stirred for 15 minutes, and then poured into saturated aqueous sodium bicarbonate and extracted into ethyl acetate. The ethyl acetate solution is dried over anhydrous potassium carbonate and concentrated under reduced pressure to give a solid which is recrystallized from acetonitrile to provide a pale pink crystalline solid.

Using the above procedure and appropriate starting materials the following compounds were prepared:
[4-(3-Dimethylamino-benzoylamino)-phenyl]-carbamic acid tert-butyl ester
(3-Bromo-5-trifluoromethyl-phenyl)-dimethyl-amine
N-(3-Chloro-5-dimethylamino-phenyl)-acetamide

EXAMPLE 55

(Method 27)

N-(4-Aminophenyl)-2-hydroxybenzamide

To a solution of 2-(4-aminophenylcarbamoyl) phenyl acetate (580 mg) in methanol (10 mL) is added saturated sodium bicarbonate (2 mL) and water (3 mL). The mixture is heated at 80° C. for 30 minutes, then poured into half-saturated aqueous sodium chloride and extracted with ethyl acetate. The ethyl acetate solution is dried over anhydrous sodium sulfate and concentrated under reduced pressure to give an oil which is then triturated with diethyl ether to provide the desired product as a white solid.

EXAMPLE 56

(Method 28)

[4-(3-(Hydroxybenzoylamino)phenyl}carbamic Acid T-butyl Ester

To a solution of of 3-(4-aminophenylcarbamoyl) phenyl acetate (4.34 g) in methanol (75 mL) is added 0.1 N aqueous sodium hydroxide (25 mL) and tetrahydrofuran (25 mL). This solution is heated at 40° C. for 30 minutes, then cooled, poured into 1 M hydrochloric acid and extracted with ethyl acetate. The ethyl acetate solution is dried over anhydrous sodium sulfate and concentrated under reduced pressure to give a white solid, which is further purified by trituration with diethyl ether.

EXAMPLE 57

(Method 29)

N-(4-Aminophenyl)-2-hydroxymethylbenzamide

To a solution of N-(4-aminophenyl)phthalimide (332 mg) in tetrahydrofuran (4 mL) is added lithium borohydride (1.0 g) and the mixture is stirred for 1 hour at 25° C. The mixture is poured into water and extracted into ethyl acetate. The ethyl acetate solution is dried over anhydrous sodium sulfate and concentrated under reduced pressure to give a white foam, which when triturated with diethyl ether provides the desired product as a white powder.

EXAMPLE 58

(Method 30)

(3-Chloro-5-dimethylamino-phenyl)-carbamic Acid Tert-butyl Ester

To a solution of (3-amino-5-chloro-phenyl)-carbamic acid tert-butyl ester (0.32 g) in toluene (10 mL) is added aqueous formaldehyde (37%, 1.5 mL) then 10% palladium on carbon (0.50 g) and the mixture is stirred under an atmosphere of hydrogen for approximately 15 hours. The solution is then filtered through diatomaceous earth and the filtrate is concentrated under reduced pressure. The residue is chromatographed over silica gel (50% dichloromethane in hexanes is used as the eluant) to provide the desired product as a white solid.

EXAMPLE 59

(Method 35)

N-(4{3-[3,5-Dichloro-4-(2-hydroxy-ethoxy)-phenyl]-thioureido}-phenyl)-acetamide

To a solution of acetic acid 2-{4-[3-(4-acetylamino-phenyl)-thioureido]-2,6-dichloro-phenoxy}-ethyl ester (0.16 g) in a 1:1 mixture of tetrahydrofuran and methanol (2.5 mL) is added 1N aqueous sodium hydroxide (1 mL) and the mixture is stirred for approximately 2 hours at room temperature. The solution is then poured into 2 M aqueous hydrochloric acid (3 mL), extracted into ethyl acetate, and the extracts are dried over anhydrous sodium sulfate. The solvent is removed by evaporation under reduced pressure and the residue is triturated with diethyl ether to provide the desired product as a white solid.

EXAMPLE 60

(Method 36)

{4-[3-(4-Acetylamino-phenyl)-thioureido]-2,6-dichloro-phenoxy}-acetic Acid

To a solution of {4-[3-(4-acetylamino-phenyl)-thioureido]-2,6-dichloro-phenoxy}-acetic acid ethyl ester (0.29 g) in a 1:1 mixture of tetrahydrofuran and methanol (4 mL) is added 1N aqueous sodium hydroxide (2 mL) and the mixture is stirred for approximately 2 hours at room temperature. The solution is then poured into 2 M aqueous hydrochloric acid (5 mL), extracted into ethyl acetate, and the extracts are dried over anhydrous sodium sulfate. The solvent is removed by evaporation under reduced pressure and the residue is triturated with diethyl ether to provide the desired product as a white solid.

Using the above procedure and appropriate starting materials the following compounds were prepared:
{4-[3-(4-Acetylamino-phenyl)-thioureido]-2,6-dichloro-phenoxy}-acetic acid
2-[3-(4-Acetylamino-phenyl)-thioureido]-4-chloro-5-methoxy-phenoxy}-acetic acid
{4-[3-(4-Acetylamino-phenyl)-thioureido]-2-chloro-5-methoxy-phenoxy}-acetic acid

EXAMPLE 61

(Method 37)

Benzoic acid 2-{4-[3-(4-acetylamino-phenyl)-thioureido]-2,6-dichloro-phenoxy}-ethyl ester To an ice cooled solution of N-(4-{3-[3,5-dichloro-4-(2-hydroxy-ethoxy)-phenyl]-thioureido}-phenyl)-acetamide (0.20 g) in pyridine (2 mL) and tetrahydrofuran (0.5 mL) is added benzoyl chloride (0.08 g) and the mixture is stirred at 0° C. for 1.5 hours. The mixture is then diluted with ethyl acetate, washed successively two times with 2% aqueous hydrochloric acid, once with saturated aqueous sodium chloride, then dried over anhydrous sodium sulfate. After removal of the solvent under reduced pressure the residue is chromatographed over silica gel (5% methanol in dichloromethane is used as the eluant) and product containing fractions are combined, evaporated under reduced pressure, and the residue is recrystallized from acetone-hexanes to provide the desired product as a white powder.

EXAMPLE 62

(Method 38)

Methanesulfonic Acid 2-{4-[3-(4-acetylamino-phenyl)-thioureido]-2,6-dichloro-phenoxy}-ethyl Ester To an ice cooled solution of N-(4-{3-[3,5-dichloro-4-(2-hydroxy-ethoxy)-phenyl]-thioureido}-phenyl)-acetamide (0.20 g) in pyridine (2 mL) and tetrahydrofuran (0.5 mL) is added methanesulfonyl chloride (0.11 g) and the solution is stirred at 0° C. for 45 minutes. The reaction mixture is then diluted with ethyl acetate, washed successively twice with 2% aqueous hydrochloric acid, once with saturated aqueous sodium chloride, and then dried over anhydrous magnesium sulfate. After removing the solvents by evaporation under reduced pressure the resulting residue is recrystallized from acetone-hexanes to give the desired product as a white powder.

EXAMPLE 63

(Method 39)

N-(4-{3-[3,5-Dichloro-4-(2-dimethylamino-ethoxy)-phenyl]-thioureido)-phenyl)-acetamide To a solution of methanesulfonic acid 2-{4-[3-(4-acetylamino-phenyl)-thioureido]- 2,6-dichlorophenoxy}-ethyl ester (0.33 g) in tetrahydrofuran (6 mL) is added aqueous dimethyl-amine (8.8 M, 0.5 mL) and the mixture is stirred at room temperature for 5 days. The reaction mixture is then diluted with ethyl acetate, then washed with saturated aqueous sodium chloride and dried over anhydrous magnesium sulfate. After removal of the solvent under reduced pressure the residue is chromatographed over silica gel (pure methanol is used as the eluant). Pooled product containing fractions are evaporated under reduced pressure and the residue is recrystallized from acetonitrile to provide the desired product as a white powder.

Using the above procedure and appropriate starting materials the following compounds were prepared:
N-(4-{3-[3,5-Dichloro-4-(2-dimethylamino-ethoxy)-phenyl]-thioureido}-phenyl)-acetamide
Benzoic acid 2-{4-[3-(4-acetylamino-phenyl)-thioureido]-2,6-dichloro-phenoxy}-ethyl ester

EXAMPLE 64

(Method 40)

Furan-2-carboxylic Acid (4-{3-[4-(1-amino-ethyl)-3-chloro-phenyl]-thioureido}-phenyl)-amide To a solution of tin(II) chloride dihydrate (0.25 g) in methanol (2.5 mL) is added furan-2-carboxylic acid (4-{3-[4-(1-azido-ethyl)-3-chloro-phenyl]-thioureido}-phenyl)-amide (0.22 g) and the solution is stirred for approximately 15 hours at room temperature. The solution is then diluted with ethyl acetate, washed successively with saturated aqueous sodium bicarbonate then saturated aqueous sodium chloride, then dried over anhydrous sodium sulfate. After removal of the solvent by evaporation under reduced pressure the residue is chromatographed over silica gel (8% methanol in dichloro-methane containing 1% triethylamine is used as the eluant) to provide the desired product as a yellow solid.

EXAMPLE 65

(Method 41)

[1,2,3]Thiadiazole-4-carboxylic Acid (4-isothiocyanato-phenyl)-amide

To a ice cooled solution of 1,1'-thiocarbonyldiimidazole (7.28 g) in tetrahydrofuran (50 mL) is added [1,2,3]-thiadiazole-4-carboxylic acid (4-amino-phenyl) amide (9.0 g) in tetrahydrofuran (100 mL). After approximately one hour the solvent is removed by evaporation and the residue is dissolved in ethyl acetate. Diethyl ether is added to precipitate the crude product, which is then collected by filtration, dissolved in dichloromethane, and passed through a plug of hydrous magnesium silicate. After removal of solvents, the residue is recrystallized from ethyl acetate-hexanes to provide the desired product as a slightly yellow solid.

Using the above procedure and appropriate starting materials the following compounds were prepared:
2-Fluoro-N-(4-isothiocyanato-phenyl)-benzamide
Furan-2-carboxylic acid (4-isothiocyanato-phenyl)-amide
[1,2,3]Thiadiazole-4-carboxylic acid (4-isothiocyanato-phenyl)-amide
Thiazole-4-carboxylic acid (4-isothiocyanato-phenyl)-amide

EXAMPLE 66

(Method 42)

N,N-Dimethyl-5-trifluoromethyl-benzene-1,3-diamine

To a solution of 3-amino-5-bromo-benzotrifluoride (1.0 g) in degassed (argon) tetrahydrofuran (2 mL) is added bis-(tri-o-tolylphosphino)palladium (0.15 g), a solution of dimethylamine in tetra-hydrofuran (2M, 4.2 mL), and a solution of lithium bis(trimethylsilyl)amide in tetrahydrofuran (1M, 10.4 mL). The reaction mixture is heated in a sealed vessel to 100° C. for approximately 2.5 hours to complete the reaction. The mixture is then cooled to room temperature, quenched by addition of water, and diluted with ethyl acetate. The product is extracted three times into 5% aqueous hydrochloric acid, and pooled acidic extracts are then basified with cooling by addition of 5N aqueous sodium hydroxide. This basic solution is then extracted with ethyl acetate, and these pooled organic extracts are washed with saturated aqueous sodium chloride, dried over anhydrous magnesium sulfate, and evaporated to dryness under reduced pressure. The resulting residue is chromatographed over silica gel (20–30% ethyl acetate in hexanes is used as the eluant) to provide the desired product as a slightly tinted solid.

Using the above procedure and appropriate starting materials the following compounds were prepared:
3-(4-Methyl-piperazin-1-yl)-5-trifluoromethyl-phenylamine
3-Morpholin-4-yl-5-trifluoromethyl-phenylamine
3-Piperidin-1-yl-5-trifluoromethyl-phenylamine
3-Pyrrolidin-1-yl-5-trifluoromethyl-phenylamine
N,N-Dimethyl-5-trifluoromethyl-benzene-1,3-diamine
N-Isobutyl-N-methyl-5-trifluoromethyl-benzene-1,3-diamine
N-Butyl-N-methyl-5-trifluoromethyl-benzene-1,3-diamine

EXAMPLE 67

(Method 43)

(3-Isobutyl-5-trifluoromethyl-phenyl)-carbamic Acid Tert-butyl Ester

To a sealed tube containing tetrahydrofuran (5 mL) that is capped with a rubber septum and cooled in a dry ice-acetone bath is bubbled isobutylene for about 5 minutes. A solution of 9-borabicyclo[3.3.1]nonane in tetrahydrofuran (0.5 M, 11 mL) is added, the vessel is sealed with a teflon cap, slowly warmed to room temperature and kept at room temperature for approximately 2.5 hours. The mixture is then re-cooled in a dry ice-acetone bath, the teflon cap is replaced by a rubber septum, and argon is bubbled through the mixture with venting to removed the excess isobutylene. A solution of (3-bromo-5-trifluoromethyl-phenyl)-carbamic acid tert-butyl ester (1.7 g) in tetrahydrofuran (12 mL) is added, followed by [1,1'-bis(diphenylphosphino)-ferrocene]palladium(II) chloride-dichlormethane complex (0.12 g), and then 3N aqueous sodium hydroxide. The vessel is again sealed with the teflon cap and is then heated to 65° C. for approximately 15 hours. The mixture is then cooled to room temperature, diluted with hexanes, washed with water, saturated aqueous sodium chloride, dried over anhydrous magnesium sulfate, and evaporated under reduced pressure. The resulting oil is chromatographed over silica gel (5% ethyl acetate in hexanes is used as the eluant) to provide the desired product as a white powder.

Using the above procedure and appropriate starting materials the following compounds were prepared:
[3-(2-Methyl-butyl)-5-trifluoromethyl-phenyl]-carbamic acid tert-butyl ester
(3-Isobutyl-5-trifluoromethyl-phenyl)-carbamic acid tert-butyl ester

EXAMPLE 68

(Method 44)

2-(3,5-Dichloro-phenylsulfanyl)-ethylamine

To a solution of (3,5-dichlorophenylthio)acetonitrile (1.2g) in 3.0 mL of ethylene glycol dimethyl ether is added 0.61 mL of 10M borane dimethyl sulfide complex and the mixture heated at reflux for 0.5 hours. The reaction is cooled in an ice bath and 2.0 mL of water and 2.0 mL of concentrated hydrochloric acid is added. This mixture is heated at reflux for 0.5 hr. The clear solution is then cooled and basified with 5N sodium hydroxide and extracted with ether. The ether extract is dried over potassium carbonate, filtered and concentrated to give 0.1 g of a colorless oil.

Using the above procedure and appropriate starting materials the following compounds were prepared:
2-(3-Bromo-phenylsulfanyl)-ethylamine
2-(4-Bromo-phenoxy)-ethylamine
2-(4-Iodo-phenoxy)-ethylamine
2-(3,4-Dichloro-phenoxy)-ethylamine
2-(3-Chloro-phenylsulfanyl)-ethylamine
2-(3,4-Dichloro-phenylsulfanyl)-ethylamine
3-(4-Bromo-phenyl)-propylamine
2-(2-Fluoro-phenoxy)-ethylamine
2-(2-Chloro-phenoxy)-ethylamine
2-(3-Bromo-phenoxy)-ethylamine
2-(3-Fluoro-phenoxy)-ethylamine 2-(3-Iodo-phenoxy)-ethylamine
2-(3,5-Dichloro-phenylsulfanyl)-ethylamine
2-Phenylsulfanyl-ethylamine
1-(2-Chloro-phenyl)-ethylamine

EXAMPLE 69

(Method 45)

N-(1-Naphthalen-2-yl-ethyl)-formamide

A mixture of 2-acetylnaphthylene (3.0 g), ammonium formate (11.0 g), formic acid 10 (3.3 mL), and formamide (3.5 mL) is heated at 190° C. for 3 hours. The mixture is cooled, poured into water and extracted with ether. The ether extract is dried with anhydrous potassium carbonate, filtered and concentrated to give a yellow oil, which is crystallized from toluene-hexanes to give a white solid, 1.97 g.

Using the above procedure and appropriate starting materials the following compounds were prepared:
N-[1-(4-Fluoro-phenyl)-2-methyl-propyl]-formamide
N-(1-Naphthalen-2-yl-ethyl)-formamide

EXAMPLE 70

(Method 46)

1-(2-Naphthyl)ethylamine

A mixture of N-(1-naphthalen-2-yl-ethyl)-formamide (1.12 g), ethanol (10 mL) and 5 N sodium hydroxide (10 mL) is heated at reflux for 1 hour. The solution is cooled, poured into water and extracted with ether. The ether solution is dried with anhydrous potassium carbonate, filtered and concentrated to give the product (0.95 g) as a pale yellow oil.

Using the above procedure and appropriate starting materials the following compounds were prepared:
1-(3-Trifluoromethyl-phenyl)-ethylamine
1-(4-Fluoro-phenyl)-2-methyl-propylamine
[3-(1-Amino-ethyl)-phenyl]-dimethyl-amine
3-(1-Amino-ethyl)-benzonitrile

EXAMPLE 71

(Method 47)

1-(3-Trifluoromethyl-phenyl)-ethanone O-methyl-oxime

Methoxylamine hydrochloride (2.33 g) is added to a solution of 3'-(trifluoromethyl) acetophenone (1.5 g) in ethanol (20 mL) and pyridine (2 mL). The solution is heated at reflux for 45 minutes. The reaction mixture is then cooled, concentrated under reduced pressure and partitioned between water and ethyl acetate. The aqueous layer is extracted with ethyl acetate. The combined organic layers are washed with saturated aqueous sodium chloride, dried over anhydrous magnesium sulfate and concentrated under reduced pressure to give the desired product as a colorless oil (1.61 g).
Using the above procedure and appropriate starting materials the following compounds were prepared:
3,5-Bis-trifluoromethyl-benzaldehyde oxime
1-(4-Fluoro-phenyl)-propan-1-one O-methyl-oxime
1-(2-Chloro-phenyl)-ethanone O-methyl-oxime
1-(3-Bromo-phenyl)-ethanone O-methyl-oxime
1-(3-Chloro-phenyl)-ethanone O-methyl-oxime
1-o-Tolyl-ethanone O-methyl-oxime
1-(4-Fluoro-phenyl)-pentan-1-one O-methyl-oxime
1-(4-Fluoro-phenyl)-2-phenyl-ethanone O-methyl-oxime
1-o-Tolyl-ethanone O-methyl-oxime
1-m-Tolyl-ethanone O-methyl-oxime
1-(2-Fluoro-phenyl)-ethanone O-methyl-oxime
3-(1-Methoxyimino-ethyl)-benzonitrile
4-(1-Methoxyimino-ethyl)-benzonitrile
1-(4-Methoxy-phenyl)-ethanone O-methyl-oxime
1-(2-Methoxy-phenyl)-ethanone O-methyl-oxime
1-(4-Dimethylamino-phenyl)-ethanone O-methyl-oxime
1-(2-Trifluoromethyl-phenyl)-ethanone O-methyl-oxime
1-(3-Methoxy-phenyl)-ethanone O-methyl-oxime
1-(3-Trifluoromethyl-phenyl)-ethanone O-methyl-oxime
1-(4-Trifluoromethyl-phenyl)-ethanone O-methyl-oxime
1-Furan-2-yl-ethanone O-methyl-oxime
1-Pyridin-4-yl-ethanone O-methyl-oxime
1-(1-Methyl-1H-pyrrol-2-yl)-ethanone O-methyl-oxime
1-Thiophen-3-yl-ethanone O-methyl-oxime
(4-Fluoro-phenyl)-phenyl-methanone O-methyl-oxime
1-(4-methoxyphenyl)ethanone O-methyloxime
1-(3-Chloro-4-methoxy-phenyl)-ethanone O-methyl-oxime
4-(1-Methoxyimino-ethyl)-benzenesulfonamide
4-(1-Methoxyimino-ethyl)-N,N-dimethyl-benzenesulfonamide
1-[4-(Piperidine-1-sulfonyl)-phenyl]-ethanone O-methyl-oxime
4-(1-Methoxyimino-ethyl)-N,N-dipropyl-benzenesulfonamide
2-Fluoro-N-[4-(1-methoxyimino-ethyl)-phenyl]-benzamide
1-(3,5-Bis-trifluoromethyl-phenyl)-ethanone O-methyl-oxime
1-[4-(1H-Imidazol-1-yl)phenyl]-1-ethanone, O-methyloxime
1-[4-(Trifluoromethyl)phenyl]-1-ethanone, O-methyloxime
1-[1,1'-Biphenyl]-4-yl-1-ethanone, O-methyloxime
1-(4-Methylphenyl)-1-ethanone, O-methyloxime
1-[4-fluoro-3-(trifluoromethyl)phenyl]ethanone O-methyloxime
1-[3,5-bis(trifluoromethyl)phenyl]ethanone O-benzyloxime
1-[4-chloro-3-(trifluoromethyl)phenyl]ethanone O-methyloxime
1-[3-fluoro-5-(trifluoromethyl)phenyl]ethanone O-methyloxime
1-[2-fluoro-4-(trifluoromethyl)phenyl]ethanone O-methyloxime
1-[2-fluoro-5-(trifluoromethyl)phenyl]ethanone O-methyloxime
1-(2,4-dichlorophenyl)ethanone O-methyloxime
1-(2,4-dimethylphenyl)ethanone O-methyloxime
1-[2,4-bis(trifluoromethyl)phenyl]ethanone O-methyloxime
1-(3-bromophenyl)ethanone O-methyloxime
1-(3-methylphenyl)ethanone O-methyloxime
1-[4-(4-morpholinyl)phenyl]ethanone O-methyloxime
1-(2-chloro-4-fluorophenyl)ethanone O-methyloxime
1-(4-bromo-2-fluorophenyl)ethanone O-methyloxime
1-(3,4-difluorophenyl)ethanone O-methyloxime
1-[3-(trifluoromethyl)phenyl]ethanone O-methyloxime
1-[2-(trifluoromethyl)phenyl]ethanone O-methyl oxime
1-(2,4-difluorophenyl)ethanone O-methyloxime
1-[3-fluoro-4-(trifluoromethyl)phenyl]ethanone O-methyloxime
1-(3,4-dichlorophenyl)ethanone O-methyloxime
1-[4-fluoro-2-(trifluoromethyl)phenyl]ethanone O-methyloxime
1-(3-chloro-4-fluorophenyl)ethanone O-methyloxime
1-(4-chloro-3-fluorophenyl)ethanone O-methyloxime
1-(2,5-difluorophenyl)ethanone O-methyloxime 1-(2-bromo-4-fluorophenyl)ethanone O-methyloxime
1-(3,4-dibromophenyl)ethanone O-methyloxime
1-(2-bromophenyl)ethanone O-methyloxime

EXAMPLE 72

(Method 48)

1-(2-Trifluoromethyl-phenyl)-ethylamine

Sodium borohydride (1.17 g) is added slowly to a flask containing zirconium tetrachloride (1.8 g) in tetrahydrofuran (27 mL). A solution of 1-(2-trifluoromethyl-phenyl)-ethanone O-methyl-oxime (1.34 g) in tetrahydrofuran (7.7 mL) is added and the resulting solution is stirred at 25° C. for 12 hours. The reaction mixture is then cooled to 0° C. and water (16 mL) is slowly added. Excess ammonium hydroxide is added and the solution is extracted twice with ethyl acetate. The organic portion is washed twice with 1N hydrochloric acid. The aqueous (acid) layer is basified with sodium hydroxide and extracted twice with ethyl acetate. The organic layer is then washed with saturated aqueous sodium chloride and dried over anhydrous magnesium sulfate. The solvent is removed under reduced pressure to provide the desired product as a yellow oil (0.20 g).

Using the above procedure and appropriate starting materials the following compounds were prepared:
1-(3-Methoxy-phenyl)-ethylamine
1-(4-Fluoro-phenyl)-propylamine
1-Naphthalen-2-yl-ethylamine
4-(1-Amino-ethyl)-benzonitrile
1-(4-Trifluoromethyl-phenyl)-ethylamine
1-(4-Methoxy-phenyl)-ethylamine
1-Prop-2-ynyl-pyrrolidine
1-(2-Methoxy-phenyl)-ethylamine
1-m-Tolyl-ethylamine
1-(2-Bromo-phenyl)-ethylamine
1-o-Tolyl-ethylamine
C-(4-Fluoro-phenyl)-C-phenyl-methylamine
1-(4-Fluoro-phenyl)-pentylamine
1-(4-Fluoro-phenyl)-2-phenyl-ethylamine
1-(2-Trifluoromethyl-phenyl)-ethylamine
1-(3-Bromo-phenyl)-ethylamine
1-(3-Chloro-phenyl)-ethylamine
[4-(1-Amino-ethyl)-phenyl]-dimethyl-amine
1-(1-Methyl-1H-pyrrol-2-yl)-ethylamine
1-[3,5-bis(trifluoromethyl)phenyl]propylamine
1-[3,5-bis(trifluoromethyl)phenyl]-1-butanamine or 1-[3,5-bis(trifluoromethyl)phenyl]butylamine
1-[3,5-bis(trifluoromethyl)phenyl]-1-pentanamine
1-(4-methylphenyl)ethanamine
1-[4-(trifluoromethyl)phenyl]ethylamine
1-(3-methylphenyl)ethanamine
1-(3,4-dichlorophenyl)ethanamine
1-(2-Bromo-phenyl)-ethylamine
1-(2-Trifluoromethyl-phenyl)-ethylamine
1-(3-Bromo-phenyl)-ethylamine
1-(3-Chloro-4-methoxy-phenyl)-ethylamine
4-(1-Amino-ethyl)-N,N-dimethyl-benzenesulfonamide
1-[4-(Piperidine-1-sulfonyl)-phenyl]-ethylamine
1-Quinolin-6-yl-ethylamine
1-(3,5-Bis-trifluoromethyl-phenyl)-ethylamine
4-[(1S)-1-aminoethyl]benzonitrile
(S)-alpha-Methyl-3,5-bis(trifluoromethyl)-benzenemethanamine(S)-alpha-Methyl-3,5-bis(trifluoromethyl)-benzenemethanamine
1-Biphenyl-4-yl-ethylamine
1-(4-Fluoro-phenyl)-ethylamine
1-[4-fluoro-3-(trifluoromethyl)phenyl]ethanamine
1-[4-chloro-3-(trifluoromethyl)phenyl]ethanamine
N-{4-[(1R)-1-aminoethyl]pheny}-1,2,3-thiadiazole-4-carboxamide
N-{4-[(1S)-1-aminoethyl]phenyl}-1,2,3-thiadiazole-4-carboxamide
1-[3-fluoro-5-(trifluoromethyl)phenyl]ethylamine
1-[2-fluoro-4-(trifluoromethyl)phenyl]ethylamine
1-[2-fluoro-5-(trifluoromethyl)phenyl]ethylamine
1-(2,4-dichlorophenyl)ethylamine
1-(2,4-dimethylphenyl)ethylamine
1-[2,4-bis(trifluoromethyl)phenyl]ethylamine
1-(2-chloro-4-fluorophenyl)ethylamine
1-(3,4-difluorophenyl)ethylamine
1-(4-bromo-2-fluorophenyl)ethylamine
1-(3-fluorophenyl)ethylamine
1-(2,4-difluorophenyl)ethylamine
1-[3-fluoro-4-(trifluoromethyl)phenyl]ethylamine
1-[4-fluoro-2-(trifluoromethyl)phenyl]ethylamine
1-(3-chloro-4-fluorophenyl)ethylamine
1-(4-chloro-3-fluorophenyl)ethylamine
1-(3,4-dibromophenyl)ethylamine
1-(2-bromo-4-fluorophenyl)ethanamine 1-(2-bromo-4-fluorophenyl)ethylamine

EXAMPLE 73

(Method 49)

(2-Fluoro-5-trifluoromethyl-phenoxy)-acetonitrile

A solution of 2-fluoro-5-trifluoromethylphenol (25 g) in reagent grade acetone (0.55 L) is treated with solid potassium carbonate (7.7 g) followed by the rapid addition of neat bromoacetonitrile (10 mL). The heterogenous mixture is stirred vigorously for approximately 20 hours whereupon it is poured into water and extracted into diethyl ether. The combined ether extracts are washed with saturated sodium chloride and dried over anhydrous potassium carbonate. Filtration and concen-tration under reduced pressure gives a pale orange solid which is then chromatographed on silica gel, eluting with dichloromethane, to give the desired product as white solid (28.3 g).

Using the above procedure and appropriate starting materials the following compounds were prepared:
(3-Bromo-phenylsulfanyl)-acetonitrile
(3-Chloro-phenylsulfanyl)-acetonitrile
(4-Iodo-phenoxy)-acetonitrile
(3-Trifluoromethyl-phenylsulfanyl)-acetonitrile
(3,5-Dichloro-phenylsulfanyl)-acetonitrile
(3,4-Dichloro-phenylsulfanyl)-acetonitrile
(3,4-Dichloro-phenoxy)-acetonitrile
(2-Fluoro-phenoxy)-acetonitrile
(3-Fluoro-phenoxy)-acetonitrile
(2-Chloro-phenoxy)-acetonitrile
(3-Bromo-phenoxy)-acetonitrile
(2-Fluoro-5-trifluoromethyl-phenoxy)-acetonitrile
(3-Iodo-phenoxy)-acetonitrile
(4-Bromo-phenoxy)-acetonitrile

EXAMPLE 74

(Method 50)

3-Fluoro-5-trifluoromethylphenethylamine Tosylate

A solution of 2.5 g of 3-fluoro-5-trifluoromethylphenylacetonitrile and 2.34 g (12.3 mmol) of p-toluenesulfonic acid in 75 ml of ethylene glycol monomethyl ether is hydrogenated for 3 hours at room temperature at 40 psi, using 200 mg 10% palladium on carbon catalyst. The catalyst is filtered off and the solvent evaporated to half the volume. Upon standing, the p-toluenesulfonic acid salt of the desired 3-fluoro-5-trifluoromethylphenethylamine crystallizes. The white crystals, 4.26g (91%) are collected by filtration.

Using the above procedure and appropriate starting materials the following compounds were prepared:
2-(3,5-Difluoro-phenyl)-ethylamine
2-(4-Trifluoromethyl-phenyl)-ethylamine
2-(3,4-Difluoro-phenyl)-ethylamine
2- (2-Fluoro-phenyl)-ethylamine
2-(3-Fluoro-5-trifluoromethyl-phenyl)-ethylamine
2-(2-Fluoro-3-trifluoromethyl-phenyl)-ethylamine
2-(2,4-Bis-trifluoromethyl-phenyl)-ethylamine
2-(4-Fluoro-3-trifluoromethyl-phenyl)-ethylamine

EXAMPLE 75

(Method 51)

(4-Aminomethyl-2-trifluoromethyl-phenyl)-dimethyl-amine

A solution of 4-dimethylamino-3-trifluoromethylbenzonitrile (0.35 g) in tetrahydrofuran (2 mL) is slowly added to a suspension of lithium aluminum hydride (0.1 g) in tetrahydrofuran (2 mL) at 0° C. and stirred under an atmosphere of argon for 2 hours. While at 0° C. water (0.1 mL) is slowly added followed by 5% sodium hydroxide (0.1 mL) and water (0.3 mL). The resulting gray solid is filtered and washed with tetrahydrofuran. The filtrates are collected and concentrated under reduced pressure and the resulting oil is chromatographed over silica gel (15% methanol in methylene chloride is used as the eluant) to provide the desired product as a pale orange oil (0.164 g).

Using the above procedure and appropriate starting materials the following compounds were prepared:
4-Piperidin-1-yl-3-trifluoromethyl-benzylamine
(4-Aminomethyl-2-trifluoromethyl-phenyl)-dimethyl-amine
4-(4-Methyl-piperazin-1-yl)-3-trifluoromethyl-benzylamine
(3-Aminomethyl-5-trifluoromethyl-phenyl)-dimethyl-amine
[3-(2-Amino-ethyl)-5-trifluoromethyl-phenyl]-dimethyl-amine
[4-(2-Amino-ethyl)-2-methyl-phenyl]-dimethyl-amine

EXAMPLE 76

(Method 52)

3-Dimethylamino-5-trifluoromethyl-benzaldehyde

Diisobutylaluminum hydride (10 mL of a 1M solution in methylene chloride) is added dropwise to a solution of 3-dimethylamino-5-trifluoromethylbenzonitrile (1.06 g) in methylene chloride (25 mL) at 0° C. and the mixture stirred for 2 hours. While still at 0° C. a saturated aqueous solution of sodium potassium tartrate (8 mL) is slowly added and the solution is stirred for 1.5 hours. The reaction mixture is then extracted with ethyl acetate, dried over anhydrous magnesium sulfate and concentrated under reduced pressure to provide the desired product as a yellow solid (0.97 g).

Using the above procedure and appropriate starting materials the following compounds were prepared:
3-Dimethylamino-5-trifluoromethyl-benzaldehyde
4-Dimethylamino-3-methyl-benzaldehyde

EXAMPLE 77

(Method 53)

Dimethyl-[3-(2-nitro-vinyl)-5-trifluoromethyl-phenyl]-amine

Nitromethane (0.473 g) is added to a solution of 3-dimethylamino-5-trifluoromethyl-benzaldehyde (0.885 g) and ammonium acetate (0.339 g) in acetic acid (3.4 mL) and the solution is heated at 110° C. for 6 hours. The reaction mixture is cooled to 0° C. and a solid forms which is filtered and washed with 1:1 water-acetic acid. This solid is recrystallized from ethanol to provide the desired product as a red solid (0.39 g).

Using the above procedure and appropriate starting materials the following compounds were prepared:
Dimethyl-[3-(2-nitro-vinyl)-5-trifluoromethyl-phenyl]-amine
Dimethyl-[ 2-methyl-4-(2-nitro-vinyl)-phenyl]-amine

EXAMPLE 78

(Method 54)

3-(4-Bromo-phenyl)-propionitrile

Diethylazodicarboxylate (5.2 g) is added dropwise to a solution of 4-bromo-phenethylalcohol (2.01 g), and triphenylphosphine (7.9 g) in diethyl ether (16 mL) at 0° C. The reaction mixture is stirred for 10 minutes and a solution of acetone cyanohydrin (2.6 g) in diethyl ether (10 mL) is added. The clear orange solution is stirred for 5 minutes at 0° C. and then at 25° C. for 12 hours. The reaction mixture is then filtered, and washed with diethyl ether. The filtrate is concentrated under reduced pressure and chromatographed over silica gel (10% ethyl acetate-hexanes is 15 used as the eluant) to provide the desired product as a pale yellow oil (2.04 g).

EXAMPLE 79

(Method 55)

3-Dimethylamino-2-isocyano-acrylic acid ethyl ester

To a solution of ethyl isocyanoacetate (5.0 g) in ethanol (100 mL) is added N,N-dimethyl-formamide dimethyl acetal (6.5 g) dropwise with stirring over 10 minutes.

The reaction is stirred for 24 hours and the ethanol is evaporated. The resulting oil is passed through magnesium silicate using 50% ethyl acetate-hexanes as the eluant. The solvents are removed and the resulting oil is crystallized from ethyl acetate-hexanes to yield light yellow needles, 3.0 g.

EXAMPLE 80

(Method 56)

4-Carboethoxythiazole

A solution of 3-dimethylamino-2-isocyano-acrylic acid ethyl ester (1.0 g) and triethylamine (3.0 g) in tetrahydrofuran (30 mL) is treated with gaseous hydrogen sulfide until all starting material is consumed. The mixture is concentrated to an oil and purified by column chromatography using silica and 25% ethyl acetate-hexanes as the eluant. The purified material (0.61 g) is isolated as an oil.

EXAMPLE 81

(Method 34)

N-{4-[3-(5-Chloro-2,4-dimethoxy-phenyl)-ureido]-phenyl}-2-fluoro-benzamide

A suspension of N-(4-amino-phenyl)-2-fluoro-benzamide (0.43 g) in acetonitrile (4 mL) is treated with 5-chloro-2,4- dimethoxyphenylisocyanate (0.40 g). The mixture becomes a solution and is allowed to stand for 12 hours. A white solid forms and is collected by filtration (0.79 g). [M+H] 444.

Using the above procedure and appropriate starting materials the following compounds were prepared:

| EX NO. | M + H | COMPOUND NAME |
|---|---|---|
| 81 | 445 | N-{4-[3-(5-Chloro-2,4-dimethoxy-phenyl)-ureido]-phenyl}-2-fluoro-benzamide |
| 82 | 441 | N-{4-[3-(5-Chloro-2,4-dimethoxy-phenyl)-ureido]-phenyl}-2-methyl-benzamide |
| 83 | 435 | [1,2,3]Thiadiazole-4-carboxylic acid {4-[3-(5-chloro-2,4-dimethoxy-phenyl)-ureido]-phenyl}-amide |
| 84 | 443 | [1,2,3]Thiadiazole-4-carboxylic acid {4-[3-(4-chloro-3-trifluoromethyl-phenyl)-ureido]-phenyl}amide |
| 85 | 453 | N-{4[3-(4-Chloro-3-trifluoromethyl-phenyl)-ureido]-phenyl}-2-fluoro-benzamide |
| 86 | 409 | [1,2,3]Thiadiazole-4-carboxylic acid {4-[3-(3,5-dichloro-phenyl)-ureido]-phenyl}-amide |
| 87 | 486 | N-{4-[3-(3,5-Bis-trifluoromethyl-phenyl)-ureido]-phenyl}-2-fluoro-benzamide |
| 88 | 458 | Furan-2-carboxylic acid {4-[3-(3,5-bis-trifluoromethyl-phenyl)-ureido]-phenyl}-amide |
| 89 | 476 | [1,2,3]Thiadiazole-4-carboxylic acid {4-[3-(3,5-bis-trifluoromethyl-phenyl)-ureido]-phenyl}-amide |
| 90 | 423 | [1,2,3]Thiadiazole-4-carboxylic acid {4-[3-(3,4-dichloro-benzyl)-ureido]-phenyl}-amide |

EXAMPLE 91

(Method 31)

N-(5-{[({(1S)-1-[3,5-bis(trifluoromethyl)phenyl]ethyl}amino)carbothioyl]amino}-2-pyridinyl)-1,3-thiazole-4-carboxamide A mixture of N-(5-isothiocyanato-2-pyridinyl)-1,3-thiazole-4-carboxamide (0.36 g) and (S)-alpha-methyl-3,5-bis(trifluoromethyl)-benzenemethanamine (0.36 g) is heated with acetonitrile (10 mL) until all solids are dissolved. The solution is allowed to stand for 12 hours. A white solid forms and is collected by filtration (0.40 g). [M+H] 520.

Using the above procedure and appropriate starting materials the following compounds were prepared:

| EX. NO. | M + H | COMPOUND NAME |
|---|---|---|
| 92 | 506 | [3-Chloro-5-(3-{4-[([1,2,3]thiadiazole-4-carbonyl)-amino]-phenyl}-thioureido)-phenyl]-carbamic acid tert-butyl ester |
| 93 | 409 | 1-(5-Chloro-2,4-dimethoxy-phenyl)-3-(4-morpholin-4-yl-phenyl)-thiourea |
| 94 | 370 | 1-(5-Chloro-2,4-dimethoxy-phenyl)-3-(4-methylsulfanyl-phenyl)-thiourea |
| 95 | 338 | 1-(5-Chloro-2,4-dimethoxy-phenyl)-3-p-tolyl-thiourea |
| 96 | 414 | {4-[3-(5-Chloro-2,4-dimethoxy-phenyl)-thioureido]-phenylsulfanyl}-acetic acid |
| 97 | 384 | 1-(5-Chloro-2,4-dimethoxy-phenyl)-3-[4-(2-hydroxy-ethoxy)-phenyl]-thiourea |
| 98 | 340 | 1-(5-Chloro-2,4-dimethoxy-phenyl)-3-(4-hydroxy-phenyl)-thiourea |
| 99 | 395 | N-{4-[3-(5-Chloro-2,4-dimethoxy-phenyl)-thioureido]-phenyl}-N-methyl-acetamide |
| 100 | 381 | N-{(3-[3-(5-Chloro-2,4-dimethoxy-phenyl)-thioureido]-phenyl}-acetamide |
| 101 | 411 | {4-[3-(5-Chloro-2,4-dimethoxy-phenyl)-thioureido]-phenyl}-carbamic acid ethyl ester |
| 102 | 319 | 1-(2,4-Dimethoxy-phenyl)-3-(4-methoxy-phenyl)-thiourea |
| 103 | 346 | N-{4-[3-(2,4-Dimethoxy-phenyl)-thioureido]-pbenyl-acetamide |
| 104 | 316 | N-{4-[3-(4-Methoxy-phenyl)-thioureido]-phenyl}-acetamide |
| 105 | 316 | N-{4-[3-(2-Methoxy-phenyl)-thioureido]-phenyl}-acetamide |
| 106 | 351 | N-{4-[3-(3-Chloro-4-methoxy-phenyl)-thioureido]-phenyl}-acetamide |
| 107 | 351 | N-{4-[3-(5-Chloro-2-methoxy-phenyl)-thioureido]-phenyl}-acetamide |
| 108 | 371 | N-{4-[3-(3,5-Dichloro-4-hydroxy-phenyl)-thioureido]-phenyl}-acetamide |
| 109 | 385 | N-{4-[3-(3,5-Dichloro-4-methoxy-phenyl)-thioureido]-phenyl}-acetamide |
| 110 | 381 | N-{4-[3-(4-Chloro-2,5-dimethoxy-phenyl)-thioureido]-phenyl}-acetamide |
| 111 | 389 | N-{4-[3-(2-Chloro-5-trifluoromethyl-phenyl)-thioureido]-phenyl}-acetamide |
| 112 | 389 | N-{4-[3-(4-Chloro-3-trifluoromethyl-phenyl)-thioureido]-phenyl}-acetamide |
| 113 | 422 | Benzoic acid 4-[3-(4-acetylamino-phenyl)-thioureido]-3-hydroxy-phenylester |
| 114 | 457 | N-{4-[3-(5-Chloro-2,4-dimethoxy-pbenyl)-thioureido]-phenyl}-2-methyl-benzamide |
| 115 | 501 | Acetic acid 2-{4-[3-(5-chloro-2,4-dimethoxy-phenyl)-thioureido]-phenyl-carbamoyl}-phenyl ester |
| 116 | 461 | N-{4-[3-(5-Chloro-2,4-dimethoxy-phenyl)-thioureido]-phenyl}-4-fluoro-benzamide |
| 117 | 461 | N-{4-[3-(5-Chloro-2,4-dimethoxy-phenyl)-thioureido]-phenyl}-3-fluoro-benzamide |
| 118 | 461 | N-{4-[3-(5-Chloro-2,4-dimethoxy-phenyl)-thioureido]-phenyl}-2-fluoro-benzamide |
| 119 | 473 | N-{4-[3-(5-Chloro-2,4-dimethoxy-phenyl)-thioureido]-phenyl}-2-methoxy-benzamide |
| 120 | 473 | N-{4-[3-(5-Chloro-2,4-dimethoxy-phenyl)-thioureido]-phenyl}-3-methoxy-benzamide |
| 121 | 473 | N-{4-[3-(5-Chloro-2,4-dimethoxy-phenyl)-thioureido]-phenyl}-4-methoxy-benzamide |
| 122 | 443 | N-{4-[3-(5-Chloro-2,4-dimethoxy-phenyl)-thioureido]-phenyl}-benzamide |
| 123 | 417 | N-{4-[3-(5-Chloro-2,4-dimethoxy-phenyl)-thioureido]-phenyl}-mehtanesulfonamide |
| 124 | 331 | N-{4-[3-(3-Nitro-phenyl)-thioureido]-phenyl}-acetamide |
| 125 | 339 | 1-(3-Chloro-4-methoxy-phenyl)-3-(3-nitro-phenyl)-thiourea |

-continued

| EX. NO. | M + H | COMPOUND NAME |
|---|---|---|
| 126 | 337 | N-{4-[3-(5-Chloro-2-hydroxy-phenyl)-thioureido]-phenyl}-acetamide |
| 127 | 439 | {4-[3-(5-Chloro-2,4-dimethoxy-phenyl)-thioureido]-phenyl}-carbamic acid tert-butyl ester |
| 128 | 351 | N-{4-[3-(3-Chloro-4-hydroxy-5-methyl-phenyl)-thioureido]-phenyl}-acetamide |
| 129 | 385 | N-{4-[3-(3,5-Dichloro-4-hydroxy-2-methyl-phenyl)-thioureido]-phenyl}-acetamide |
| 130 | 318 | N-{4-[3-(2,4-Dihydroxy-phenyl)-thioureido]-phenyl}-acetamide |
| 131 | 414 | N-{4-[3-(2,4-Dimethoxy-5-trifluoromethyl-phenyl)-thioureido]-phenyl}-acetamide |
| 132 | 332 | N-{4-[3-(2-Hydroxy-4-methoxy-phenyl)-thioureido]-phenyl}-acetamide |
| 133 | 465 | N-{4-[3-(3,5-Dichloro-4-methoxy-phenyl)-thioureido]-phenyl}-4-fluoro-benzamide |
| 134 | 500 | 3-Acetylamino-N-{4-[3-(5-chloro-2,4-dimethoxy-phenyl)-thioureido]-phenyl}-benzamide |
| 135 | 488 | N-{4-[3-(5-Chloro-2,4-dimethoxy-phenyl)-thioureido]-phenyl}-3-nitro-benzamide |
| 136 | 486 | N-{4-[3-(5-Chloro-2,4-dimethoxy-phenyl)-thioureido]-phenyl}-3-dimethylamino-Benzamide |
| 137 | 536 | N-{4-[3-(5-Chloro-2,4-dimethoxy-phenyl)-thioureido]-phenyl}-3-methane-sulfony-amino-benzamide |
| 138 | 511 | N-{4-[3-(5-Chloro-2,4-dimethoxy-phenyl)-thioureido]-phenyl}-2-trifluoro-methyl-benzamide |
| 139 | 459 | N-{4-[3-(5-Chloro-2,4-dimethoxy-phenyl)-thioureido]-phenyl}-2-hydroxy-benzamide |
| 140 | 479 | N-{4-[3-(5-Chloro-2,4-dimethoxy-phenyl)-thioureido]-phenyl}-2,6-difluoro-benzamide |
| 141 | 477 | 2-Chloro-N-{4-[3-(5-chloro-2,4-dimethoxy-phenyl)-thioureido]-phenyl}-benzamide |
| 142 | 522 | 2-Bromo-N-{4-[3-(5-chloro-2,4-dimethoxy-phenyl)-thioureido]-phenyl}-benzamide |
| 143 | 488 | N-{4-[3-(5-Chloro-2,4-dimethoxy-phenyl)-thioureido]-phenyl}-2-nitro-benzamide |
| 144 | 445 | Pyrazine-2-carboxylic acid {4-[3-(5-chloro-2,4-dimethoxy-phenyl)-thioureido]-phenyl}-amide |
| 145 | 463 | 5-Methyl-thiophene-2-carboxylic acid {4-[3-(5-chloro-2,4-dimethoxy-phenyl)-thioureido]-phenyl}-amide |
| 146 | 494 | Quinoline-8-carboxlic acid {4-[3-(5-chloro-2,4-dimethoxy-phenyl)-thioureido]-phenyl}-amide |
| 147 | 446 | 1-Methyl-1H-pyrrole-2-carboxylic acid {4-[3-(5-chloro-2,4-dimethoxy-phenyl)-thioureido]-phenyl}-amide |
| 148 | 369 | 1-(5-Chloro-2,4-dimethoxy-phenyl)-3-(2-nitro-phenyl)-thiourea |
| 149 | 369 | 1-(5-Chloro-2,4-dimethoxy-phenyl)-3-(4-nitro-phenyl)-thiourea |
| 150 | 425 | N-{4-[3-(5-Bromo-2,4-dimethoxy-phenyl)-thioureido]-phenyl}-acetamide |
| 151 | 376 | N-{4-[3-(3,4,5-Trimethoxy-phenyl)-thioureido]-phenyl}-acetamide |
| 152 | 399 | N-{4-[3-(3,5-Dichloro-2-methoxy-4-methyl-phenyl)-thioureido]-phenyl}-acetamide |
| 153 | 499 | Benzo[b]thiophene-2-carboxylic acid {4-[3-(5-chloro-2,4-dimethoxy-phenyl)-thioureido]-phenyl}-amide |
| 154 | 483 | Benzofuran-2-carboxylic acid {4-[3-(5-chloro-2,4-dimethoxy-phenyl)-thioureido]-phenyl}-amide |
| 155 | 444 | N-{4-[3-(5-Chloro-2,4-dimethoxy-phenyl)-thioureido]-phenyl}-isonicotinamide |
| 156 | 493 | Naphthalene-2-carboxylic acid {4-[3-(5-chloro-2,4-dimethoxy-phenyl)-thioureido]-phenyl}-amide |
| 157 | 493 | Naphthalene-1-carboxylic acid {4-[3-(5-chloro-2,4-dimethoxy-phenyl)-thioureido]- phenyl}-amide |
| 158 | 494 | Isoquinoline-1-carboxylic acid {4-[3-(5-chloro-2,4-dimethoxy-phenyl)-thioureido]-phenyl}-amide |
| 159 | 494 | Quinoline-2-carboxylic acid {4-[3-(5-chloro-2,4-dimethoxy-phenyl)-thioureido]-phenyl}-amide |
| 160 | 444 | N-{4-[3-(5-Chloro-2,4-dimethoxy-phenyl)-thioureido]-phenyl}-nicotinamide |
| 161 | 478 | 5-Nitro-furan-2-carboxylic acid {4-[3-(5-chloro-2,4-dimethoxy-phenyl)-thioureido]-phenyl}-amidecarbamic acid phenyl ester |
| 162 | 459 | {4-[3-(5-Chloro-2,4-dimethoxy-phenyl)-thioureido]-phenyl}- |
| 163 | 467 | 5-Chloro-furan-2-carboxylic acid {4-[3-(5-chloro-2,4-dimethoxy-phenyl)-thioureido]-phenyl}-amide |
| 164 | 439 | {4-[3-(5-Chloro-2,4-dimethoxy-phenyl)-thioureido]-phenyl}-carbamic acid isobutyl ester |
| 165 | 397 | {4-[3-(5-Chloro-2,4-dimethoxy-phenyl)-thioureido]-phenyl}-carbamic acid methyl ester |
| 166 | 433 | Furan-3-carboxylic acid {4-[3-(5-chloro-2,4-dimethoxy-phenyl)-thioureido]-phenyl}-amide |
| 167 | 447 | 3-Methyl-furan-2-carboxylic acid {4-[3-(5-chloro-2,4-dimethoxy-phenyl)-thioureido]-phenyl}-amide |
| 168 | 512 | 5-Bromo-furan-2-carboxylic acid {4-[3-(5-chloro-2,4-dimethoxy-phenyl)-thioureido]-phenyl}-amide |
| 169 | 512 | 4-Bromo-furan-2-carboxylic acid {4-[3-(5-chloro-2,4-dimethoxy-phenyl)-thioureido]-phenyl}-amide |
| 170 | 433 | Furan-2-carboxylic acid {4-[3-(5-chloro-2,4-dimethoxy-phenyl)-thioureido]-phenyl}-amide |
| 171 | 467 | {4-[3-(5-Chloro-2,4-dimethoxy-phenyl)-thioureido]-phenyl}-carbamic acid hexyl ester |
| 172 | 494 | Isoquinoline-4-carhoxylic acid {4-[3-(5-chloro-2,4-dimethoxy-phenyl)-thioureido]-phenyl}-amide |
| 173 | 451 | [1,2,3]Thiadiazole-4-carboxylic acid {4-[3-(5-chloro-2,4-dimethoxy-phenyl)-thioureido]-phenyl}-amide |
| 174 | 434 | 1H-[1,2,3]Triazole-4-carboxylic acid {4-[3-(5-chloro-2,4-dimethoxy-phenyl)-thioureido]-phenyl}-amide |
| 175 | 528 | 3-Bromo-thiophene-2-carboxylic acid {4-[3-(5-chloro-2,4-dimethoxy-phenyl)-thioureido]-phenyl}-amide |
| 176 | 399 | N-{4-[3-(3,5-Dichloro-4-ethoxy-phenyl)-thioureido]-phenyl}-acetamide |
| 177 | 427 | N-{4-[3-(4-Butoxy-3,5-dichloro-phenyl)-thioureido]-phenyl}-acetamide |
| 178 | 461 | N-{4-[3-(4-Benzyloxy-3,5-dichloro-phenyl)-thioureido]-phenyl}-acetamide |
| 179 | 381 | N-{4-[3-(3-Chloro-2,4-dimethoxy-phenyl)-thioureido]-phenyl}-acetamide |
| 180 | 530 | (3-{4-[3-(5-Chloro-2,4-dimethoxy-phenyl)-thioureido]-phenylcarbamoyl}-phenyl)-carbamic acid ethyl ester |
| 181 | 458 | 2-Amino-N-{4-[3-(5-chloro-2,4-dimethoxy-phenyl)-thioureido]-phenyl}-benzamide |
| 182 | 519 | Biphenyl-2-carboxylic acid {4-[3-(5-chloro-2,4-dimethoxy-phenyl)-thioureido]-phenyl}-amide |
| 183 | 469 | 1-(5-Chloro-2,4-dimethoxy-phenyl)-3-[4-(1,3-dioxo-1,3-dihydro-isoindol-2-yl)-phenyl]-thiourea |
| 184 | 487 | N-{4-[3-(5-Chloro-2,4-dimethoxy-phenyl)-thioureido]-phenyl}-phthalamic acid |
| 185 | 473 | N-{4-[3-(5-Chloro-2,4-dimethoxy-phenyl)-thioureido]-phenyl}-2-hydroxy-methyl-benzamide |
| 186 | 479 | N-{4-[3-(5-Chloro-2,4-dimethoxy-phenyl)-thioureido]-phenyl}-2,3-difluoro-benzamide |
| 187 | 479 | N-{4-[3-(5-Chloro-2,4-dimethoxy-phenyl)-thioureido]-phenyl}-2,5-difluoro-benzamide |
| 188 | 479 | N-{4-[3-(5-Chloro-2,4-dimethoxy-phenyl)-thioureido]-phenyl}-2,4-difluoro-benzamide |
| 189 | 500 | 2-Acetylamino-N-{4-[3-(5-chloro-2,4-dimethoxy-phenyl)-thioureido]-phenyl}-benzamide |
| 190 | 441 | 1-(5-Chloro-2,4-dimethoxy-phenyl)-3-(6-oxo-5,6-dihydro-phenanthridin-2-yl)-thiourea |
| 191 | 536 | N-{4-[3-(5-Chloro-2,4-dimethoxy-phenyl)-thioureido]-phenyl}-2-methane-sulfonylamino-benzamide |
| 192 | 497 | N-{4-[3-(5-Chloro-2,4-dimethoxy-phenyl)-thioureido]-phenyl-2,3,4-trifluoro-benzamide |
| 193 | 533 | N-{4-[3-(5-Chloro-2,4-dimethoxy-phenyl)-thioureido]-phenyl}-2,3,4,5,6-pentafluoro-benzamide |
| 194 | 489 | N-{4-[3-(5-Chloro-2,4-dimethoxy-phenyl)-thioureido]-phenyl}-2-methyl-sulfanyl-benzamide |
| 195 | 431 | 5-Methyl-furan-2-carboxylic acid {4-[3-(5-chloro-2,4-dimethoxy-phenyl)-ureido]-phenyl}-amide |
| 196 | 467 | 5-Difluoromethyl-furan-2-carboxylic acid {4-[3-(5-chloro-2,4-dimethoxy-phenyl)-ureido]-phenyl}-amide |
| 197 | 472 | N-{4-[3-(5-Iodo-2,4-dimethoxy-phenyl)-thioureido]-phenyl}-acetamide |
| 198 | 364 | N-{4-[3-(5-Fluoro-2,4-dimethoxy-phenyl)-thioureido]-phenyl}-acetamide |
| 199 | 365 | N-{4-[3-(5-Chloro-2-methoxy-4-methyl-phenyl)-thioureido]-phenyl}-acetamide |
| 200 | 459 | [1,2,3]Thiadiazole-4-carboxylic acid {4-[3-(4-chloro-3-trifluoromethyl-phenyl)-thioureido]-phenyl}-amide |
| 201 | 455 | [1,2,3]Thiadiazole-4-carboxylic acid {4-[3-(3,5-dichloro-4-methoxy-phenyl)-thioureido]-phenyl}-amide |

-continued

| EX. NO. | M + H | COMPOUND NAME |
|---|---|---|
| 202 | 392 | N-{4-[3-(3-Chloro-4-diethylamino-phenyl)-thioureido]-phenyl}-acetamide |
| 203 | 432 | N-(4-{3-[3-Chloro-4-(cyclohexyl-methyl-amino)-phenyl]thioureido}-phenyl)-acetamide |
| 204 | 506 | 1-Hydroxy-naphthalene-2-carboxylic acid {4-[3-(4-acetylamino-phenyl)-thioureido]-2-chloro-phenyl}-amide |
| 205 | 406 | N-{4-[3-(3-Chloro-4-morpholin-4-yl-phenyl)-thioureido]-phenyl}-acetamide |
| 206 | 443 | 1-(5-Chloro-2,4-dimethoxy-phenyl)-3-(3-chloro-4-morpholin-4-yl-phenyl)-thiourea |
| 207 | 372 | 1-(5-Chloro-2,4-dimethoxy-phenyl)-3-(5-chloro-2-methyl-phenyl)-thiourea |
| 208 | 501 | N-{4-[3-(5-Chloro-2,4-dimethoxy-phenyl)-thioureido]-phenyl}-isophthalamic acid methyl ester |
| 209 | 487 | N-{4-[3-(5-Chloro-2,4-dimethoxy-phenyl)-thioureido]-phenyl}-isophthalamic acid |
| 210 | 549 | 3-Benzyloxy-N-{4-[3-(5-chloro-2,4-dimethoxy-phenyl)-thioureido]-phenyl}- benzamide |
| 211 | 434 | N-(4-{3-[5-Chloro-2-methoxy-4-(4-nitrilo-butoxy)-phenyl]-thioureido}-phenyl)-acetamide |
| 212 | 406 | N-(4-{3-[5-Chloro-2-methoxy-4-(2-nitrilo-ethoxy)-phenyl]-thioureido}-phenyl)-acetamide |
| 213 | 406 | N-(4-{3-[5-Chloro-4-methoxy-2-(2-nitrilo-ethoxy)-phenyl]-thioureido}-phenyl)-acetamide |
| 214 | 411 | N-(4-{3-[5-Chloro-2-(2-hydroxy-ethoxy)-4-methoxy-phenyl]-thioureido}-phenyl)-acetamide |
| 215 | 411 | N-(4-{3-[5-Chloro-4-(2-hydroxy-ethoxy)-2-methoxy-phenyl]-thioureido}-phenyl)-acetamide |
| 216 | 481 | {4-[3-(4-Acetylamino-phenyl)-thioureido]-2-chloro-5-methoxy-phenoxy}-acetic acid tert-butyl ester |
| 217 | 439 | {4-[3-(4-Acetylamino-phenyl)-thioureido]-2-chloro-5-methoxy-phenoxy}-acetic acid methyl ester |
| 218 | 481 | {2-[3-(4-Acetylamino-phenyl)-thioureido]-4-chloro-5-methoxy-phenoxy}-acetic acid tert-butyl ester |
| 219 | 515 | 3-Butoxy-N-{4-[3-(5-chloro-2,4-dimethoxy-phenyl)-thioureido]-phenyl}-benzamide |
| 220 | 505 | N-{4-[3-(5-Chloro-2,4-dimethoxy-phenyl)-thioureido]-phenyl}-2-methane-sulfinyl-benzamide |
| 221 | 545 | (3-{4-[3-(5-Chloro-2,4-dimethoxy-phenyl)-thioureido]-phenylcarbamoyl}-phenoxy)-acetic acid ethyl ester |
| 222 | 517 | (3-{4-[3-(5-Chloro-2,4-dimethoxy-phenyl)-thioureido]-phenylcarbamoyl}-phenoxy)-acetic acid |
| 223 | 367 | N-{4-[3-(5-Chloro-4-hydroxy-2-methoxy-phenyl)-thioureido]-phenyl}-acetamide |
| 224 | 444 | Pyridine-2-carboxylic acid {4-[3-(5-chloro-2,4-dimethoxy-phenyl)-thioureido]-phenyl}-amide |
| 225 | 494 | Quinoline-4-carboxylic acid {4-[3-(5-chloro-2,4-dimethoxy-phenyl)-thioureido]-phenyl}-amide |
| 226 | 436 | N-{4-[3-(5-Chloro-4-methoxy-2-morpholin-4-yl-phenyl)-thioureido]-phenyl}-acetamide |
| 227 | 394 | N-{4-[3-(5-Chloro-2-dimethylamino-4-methoxy-phenyl)-thioureido]-phenyl}-acetamide |
| 228 | 420 | N-{4-[3-(5-Chloro-4-methoxy-2-pyrrolidin-1-yl-phenyl)-thioureido]-phenyl}-acetamide |
| 229 | 434 | N-{4-[3-(5-Chloro-4-methoxy-2-piperidin-1-yl-phenyl)-thioureido]-phenyl}-acetamide |
| 230 | 405 | [1,2,3]Thiadiazole-4-carboxylic acid {4-[3-(3-chloro-4-methyl-phenyl)-thioureido]-phenyl}-amide |
| 231 | 415 | N-{4-[3-(3-Chloro-4-methyl-phenyl)-thioureido]-phenyl}-2-fluoro-benzamide |
| 232 | 427 | N-{4-[3-(3-Chloro-4-methyl-phenyl)-thioureido]-phenyl}-3-methoxy-benzamide |
| 233 | 387 | Furan-2-carboxylic acid {4-[3-(3-chloro-4-methyl-phenyl-thioureido]-phenyl}-amide |
| 234 | 411 | N-{4-[3-(3-Chloro-4-methyl-phenyl)-thioureido]-phenyl}-2-methyl-benzamide |
| 235 | 433 | N-{4-[3-(3-Chloro-4-methyl-phenyl)-thioureido]-phenyl}-2,6-difluoro-benzamide |
| 236 | 398 | Pyridine-2-carboxylic acid {4-[3-(3-chloro-4-methyl-phenyl)-thioureido]-phenyl}-amide |
| 237 | 502 | [1,2,3]Thiadiazole-4-carboxylic acid (4-{3-[3-chloro-4-(cyclohexyl-methyl-amino)-phenyl]-thioureido}-phenyl)-amide |
| 238 | 512 | N-(4-{3-[3-Chloro-4-(cyclohexyl-methyl-amino)-phenyl]-thioureido}-phenyl)-2-fluoro-benzamide |
| 239 | 404 | N-{4-[3-(3-Chloro-4-piperidin-1-yl-phenyl)-thioureido]-phenyl}-acetamide |
| 240 | 364 | N-{4-[3-(3-Chloro-4-dimethylamino-phenyl)-thioureido]-phenyl}-acetamide |
| 241 | 426 | N-{4-[3-(4-Benzylamino-3-chloro-phenyl)-thioureido]-phenyl}-acetamide |
| 242 | 390 | N-{4-[3-(3-Chloro-4-pyrrolidin-1-yl-phenyl)-thioureido]-phenyl}-acetamide |
| 243 | 419 | N-(4-{3-[3-Chloro-4-(4-methyl-piperazin-1-yl)-phenyl]-thioureido}-phenyl)-acetamide |
| 244 | 469 | N-{4-[3-(4-Chloro-3-trifluoromethyl-phenyl)-thioureido]-phenyl}-2-fluoro-benzamide |
| 245 | 422 | N-{4-[3-(2-Benzylamino-4-methoxy-phenyl)-thioureido]-phenyl}-acetamide |
| 246 | 484 | Furan-2-carboxylic acid (4-{3-[3-chloro-4-(cyclohexyl-methyl-amino)-phenyl]-thioureido}-phenyl)-amide |
| 247 | 508 | N-(4-{3-[3-Chloro-4-(cyclohexyl-methyl-amino)-phenyl]-thioureido}-phenyl)-2-methyl-benzamide |
| 248 | 530 | N-(4-{3-[3-Chloro-4-(cyclohexyl-methyl-amino)-phenyl]-thioureido}-phenyl)-2,6-difluoro-benzamide |
| 249 | 495 | Pyridine-2-carboxylic acid (4-{3-[3-chloro-4-(cyclohexyl-methyl-amino)-phenyl]-thioureido}-phenyl)-amide |
| 250 | 524 | N-(4-{3-[3-Chloro-4-(cyclohexyl-methyl-amino)-phenyl]-thioureido}-phenyl)-3-methoxy-benzamide |
| 251 | 376 | N-(4-{3-[3-Chloro-4-(2-nitrilo-ethoxy)-phenyl]-thioureido}-phenyl)-acetamide |
| 252 | 393 | N-{4-[3-(4-sec-Butoxy-3-chloro-phenyl)-thioureido]-phenyl}-acetamide |
| 253 | 501 | Acetic acid 3-{4-[3-(5-chloro-2,4-dimethoxy-phenyl)-thioureido]-phenyl-carbamoyl}-phenyl ester |
| 254 | 459 | N-{4-[3-(5-Chloro-2,4-dimethoxy-phenyl)-thioureido]-phenyl}-3-hydroxy-benzamide |
| 255 | 487 | Benzo[1,3]dioxole-4-carboxylic acid {4-[3-(5-chloro-2,4-dimethoxy-phenyl)-thioureido]-phenyl}-amide |
| 256 | 527 | N-{4-[3-(5-Chloro-2,4-dimethoxy-phenyl)-thioureido]-phenyl}-3-trifluoro-methoxy-benzamide |
| 257 | 530 | N-{4-[3-(5-Chloro-2,4-dimethoxy-phenyl)-thioureido]-phenyl}-3-(2-dimethylamino-ethoxy)-benzamide |
| 258 | 572 | N-{4-[3-(5-Chloro-2,4-dimethoxy-phenyl)-thioureido]-phenyl}-3-(2-morpholin-4-yl-ethoxy)-benzamide |
| 259 | 406 | N-{4-[3-(5-Chloro-2,4-dimethoxy-phenyl)-thioureido]-2-cyano-phenyl}-acetamide |
| 260 | 521 | N-{4-[3-(5-Chloro-2,4-dimethoxy-phenyl)-thioureido]-2,5-dimethoxy-phenyl}-2-fluoro-benzamide |
| 261 | 441 | N-{4-[3-(5-Chloro-2,4-dimethoxy-phenyl)-thioureido]-2,5-dimethoxy-phenyl}-acetamide |
| 262 | 527 | 2-{4-[3-(4-Acetylamino-phenyl)-thioureido]-2-chloro-phenoxy}-5-chloro-benzenesulfonic acid |
| 263 | 562 | 2-{4-[3-(4-Acetylamino-phenyl)-thioureido]-2-chloro-phenoxy}-4,5-dichloro-benzenesulfonic acid |
| 264 | 527 | 4-Phenyl-[1,2,3]thiadiazole-5-carboxylic acid{4-[3-(5-chloro-2,4-dimethoxy-phenyl)-thioureido]-phenyl}-amide |
| 265 | 381 | N-(4-{3-[3-Chloro-4-(2-hydroxy-ethoxy)-phenyl]-thioureido}-phenyl)-acetamide |
| 266 | 393 | N-{4-[3-(4-Butoxy-3-chloro-phenyl)-thioureido]-phenyl}-acetamide |
| 267 | 446 | N-(4-{3-[3-Chloro-4-(cyclohexyl-ethyl-amino)-phenyl]-thioureido}-phenyl)-acetamide |
| 268 | 365 | N-{4-[3-(3-Chloro-4-ethoxy-phenyl)-thioureido]-phenyl}-acetamide |
| 269 | 427 | N-{4-[3-(4-Benzyloxy-3-chloro-phenyl)-thioureido]-phenyl}-acetamide |
| 270 | 317 | {4-[(3-Methyl-furan-2-carbonyl)-amino]-phenyl}-carbamic acid tert-butyl ester |
| 271 | 456 | N-{4-[3-(2-Benzylamino-5-chloro-4-methoxy-phenyl)-thioureido]-phenyl}-acetamide |
| 272 | 420 | N-{4-[3-(3-Chloro-4-dipropylamino-phenyl)-thioreido]-phenyl}-acetamide |
| 273 | 458 | N-(4-{3-[4-(Allyl-cyclohexyl-amino)-3-chloro-phenyl]-thioureido}-phenyl)-acetamide |
| 274 | 411 | N-{4-[3-(5-Chloro-2,4-dimethoxy-phenyl)-thioureido]-2-methoxy-phenyl}-acetamide |
| 275 | 415 | N-{2-Chloro-4-[3-(5-chloro-2,4-dimethoxy-phenyl)-thioureido]-phenyl}-acetamide |
| 276 | 493 | Furan-2-carboxylic acid {4-[3-(5-chloro-2,4-dimethoxy-phenyl)-thioureido]-2,5-dimethoxy-phenyl}-amide |
| 277 | 486 | N-{4-[3-(5-Chloro-2,4-dimethoxy-phenyl)-thioureido]-2-cyano-phenyl}-2-fluoro-benzamide |

-continued

| EX. NO. | M + H | COMPOUND NAME |
|---|---|---|
| 278 | 495 | N-{2-Chloro-4-[3-(5-chloro-2,4-dimethoxy-phenyl)-thioureido]-phenyl}-2-fluoro-benzamide |
| 279 | 465 | 5-Methyl-[1,2,3]thiadiazole-4-carboxylic acid{4-[3-(5-chloro-2,4-dimethoxy-phenyl)-thioureido]-phenyl}-amide |
| 280 | 517 | 5-Furan-3-yl-[1,2,3]thiadiazole-4-carboxylic acid{4-[3-(5-chloro-2,4-dimethoxy-phenyl)-thioureido]-phenyl}amide |
| 281 | 527 | 5-Phenyl-[1,2,3]thiadiazole-4-carboxylic acid{4-[3-(5-chloro-2,4-dimethoxy-phenyl)-thioureido]-phenyl}-amide |
| 282 | 458 | N-(4-{3-[3-Chloro-4-(octahydro-quinolin-1-yl)-phenyl]-thioureido}-phenyl)-acetamide |
| 283 | 458 | N-[5-[[[(5-Chloro-2,4-dimethoxyphenyl)amino]thioxomethyl]amino]-2-pyridinyl]-2-methylbenzamide |
| 284 | 434 | Furan-2-carboxylic acid {5-[3-(5-chloro-2,4-dimethoxy-phenyl)-thioureido]-pyridin-2-yl}-amide |
| 285 | 425 | N-{4-[3-(5-Chloro-2,4-dimethoxy-phenyl)-thioureido]-2-methoxy-5-methyl-phenyl}-acetamide |
| 286 | 505 | N-{4-[3-(5-Chloro-2,4-dimethoxy-phenyl)-thioureido]-2-methoxy-5-methyl-phenyl}-2-fluoro-benzamide |
| 287 | 477 | Furan-2-carboxylic acid {4-[3-(5-chloro-2,4-dimethoxy-phenyl)-thioureido]-2-methoxy-5-methyl-phenyl}-amide |
| 288 | 517 | 4-Furan-3-yl-[1,2,3]thiadiazole-5-carboxylic acid{4-[3-(5-chloro-2,4-dimethoxy-phenyl)-thioureido]-phenyl}-amide |
| 289 | 462 | N-{5-[3-(5-Chloro-2,4-dimethoxy-phenyl)-thioureido]-pyridin-2-yl}-2-fluoro-benzamide |
| 290 | 384 | N-{4-[3-(4-Methoxy-3-trifluoromethyl-phenyl)-thioureido]-phenyl}-acetamide |
| 291 | 394 | N-[4-(3-{3-Chloro-4-[(2-hydroxy-ethyl)-methyl-amino]-phenyl}-thioureido)-phenyl]-acetamide |
| 292 | 485 | N-{2-Benzoyl-4-[3-(5-chloro-2,4-dimethoxy-phenyl)-thioureido]-phenyl}-acetamide |
| 293 | 565 | N-{2-Benzoyl-4-[3-(5-chloro-2,4-dimethoxy-phenyl)-thioureido]-phenyl}-2-fluoro-benzamide |
| 294 | 537 | Furan-2-carboxylic acid {2-benzoyl-4-[3-(5-chloro-2,4-dimethoxy-phenyl)-thioureido]-phenyl}-amide |
| 295 | 475 | N-{4-[3-(5-Chloro-2,4-dimethoxy-phenyl)-thioureido]-3-methyl-phenyl}-2-fluoro-benzamide |
| 296 | 447 | Furan-2-carboxylic acid {4-[3-(5-chloro-2,4-dimethoxy-phenyl)-thioureido]-3-methyl-phenyl}-amide |
| 297 | 395 | N-{4-[3-(5-Chloro-2,4-dimethoxy-phenyl)-thioureido]-3-methyl-phenyl}-acetamide |
| 298 | 435 | N-[4-(3-{3-Chloro-4-[(3-dimethylamino-propyl)-methyl-amino]-phenyl}-thioureido)-phenyl]-acetamide |
| 299 | 418 | N-{4-[3-(3-Chloro-4-cyclohexylamino-phenyl)-thioureido]-phenyl}-acetamide |
| 300 | 421 | N-[4-(3-{3-Chloro-4-[(2-dimethylamino-ethyl)-methyl-amino]-phenyl}-thioureido)-phenyl]-acetamide |
| 301 | 580 | 5-[[[(5-Chloro-2,4-dimethoxyphenyl)amino]thioxomethyl]amino]-2-[(2-fluorobenzoyl)amino]-N-phenyl-benzamide |
| 302 | 552 | Furan-2-carboxylic acid {4-[3-(5-chloro-2,4-dimethoxy-phenyl)-thioureido]-2-phenylcarbamoyl-phenyl}-amide |
| 303 | 491 | N-{4-[3-(5-Chloro-2,4-dimethoxy-phenyl)-thioureido]-2-methoxy-phenyl}-2-fluoro-benzamide |
| 304 | 463 | Furan-2-carboxylic acid {4-[3-(5-chloro-2,4-dimethoxy-phenyl)-thioureido]-2-methoxy-phenyl}-amide |
| 305 | 449 | N-{4-[3-(5-Chloro-2,4-dimethoxy-phenyl)-thioureido]-2-trifluoromethyl-phenyl}-acetamide |
| 306 | 458 | Furan-2-carboxylic acid{4-[3-(5-chloro-2,4-dimethoxy-phenyl)-thioureido]-2-cyano-phenyl}-amide |
| 307 | 467 | Furan-2-carboxylic acid {2-chloro-4-[3-(5-chloro-2,4-dimethoxy-phenyl)-thioureido]-phenyl}-amide |
| 308 | 501 | Furan-2-carboxylic acid {4-[3-(5-chloro-2,4-dimethoxy-phenyl)-thioureido]-2-trifluoromethyl-phenyl}-amide |
| 309 | 395 | N-{4-[3-(5-Chloro-2,4-dimethoxy-phenyl)-thioureido]-2-methyl-phenyl}-acetamide |
| 310 | 475 | N-{4-[3-(5-Chloro-2,4-dimethoxy-phenyl)-thioureido]-2-methyl-phenyl}-2-fluoro-benzamide |
| 311 | 447 | Furan-2-carboxylic acid {4-[3-(5-chloro-2,4-dimethoxy-phenyl)-thioureido]-2-methyl-phenyl}-amide |
| 312 | 378 | N-{4-[3-(4-Acetylamino-phenyl)-thioureido]-2-chloro-phenyl}-acetamide |
| 313 | 408 | {4-[3-(4-Acetylamino-phenyl)-thioureido]-2-chloro-phenyl}-carbamic acid ethyl ester |
| 314 | 382 | N-{5-[3-(5-Chloro-2,4-dimethoxy-phenyl)-thioureido]-pyridin-2-yl}-acetamide |
| 315 | 509 | N-(4-{3-[4-(1-Benzyl-piperidin-4-ylamino)-3-chloro-phenyl]-thioureido}-phenyl)-acetamide |
| 316 | 407 | N-(4-{3-[3-Chloro-4-(2-dimethylamino-ethylamino)-phenyl]-thioureido}-phenyl)-acetamide |
| 317 | 408 | N-[4-(3-{3-Chloro-4-[(2-methoxy-ethyl)-methyl-amino]-phenyl}-thioureido)-phenyl]-acetamide |
| 318 | 421 | N-(4-{3-[3-Chloro-4-(3-dimethylamino-propylamino)-phenyl]-thioureido}-phenyl)-acetamide |
| 319 | 495 | N-(4-{3-[4-(1-Benzyl-pyrrolidin-3-ylamino)-3-chloro-phenyl]-thioureido}-phenyl)-acetamide |
| 320 | 483 | Furan-2-carboxylic acid {5-chloro-4-[3-(5-chloro-2,4-dimethoxy-phenyl)-thioureido]-2-hydroxy-phenyl}-amide |
| 321 | 431 | N-{5-Chloro-4-[3-(5-chloro-2,4-dimethoxy-phenyl)-thioureido]-2-hydroxy-phenyl}-acetamide |
| 322 | 511 | (5H,11H-Benzo[e]pyrrolo[1,2-a][1,4]diazepin-10-yl)-(2-chloro-4-imidazol-1-yl-phenyl)-methanone |
| 323 | 451 | [1,2,3]Thiadiazole-5-carboxylic acid {4-[3-(5-chloro-2,4-dimethoxy-phenyl)-thioureido]-phenyl}-amide |
| 324 | 483 | Furan-2-carboxylic acid {4-[3-(5-chloro-2,4-dimethoxy-phenyl)-thioureido]-naphthalen-1-yl}-amide |
| 325 | 511 | N-{4-[3-(5-Chloro-2,4-dimethoxy-phenyl)-thioureido]-naphthalen-1-yl}-2-fluoro-benzamide |
| 326 | 429 | N-{5-Chloro-4-[3-(5-chloro-2,4-dimetboxy-phenyl)-thioureido]-2-methyl-phenyl}-acetamide |
| 327 | 509 | N-{5-Chloro-4-[3-(5-chloro-2,4-dimethoxy-phenyl)-thioureido]-2-methyl-phenyl}-2-fluoro-benzamide |
| 328 | 481 | Furan-2-carboxylic acid {5-chloro-4-[3-(5-chloro-2,4-dimethoxy-phenyl)-thioureido]-2-methyl-phenyl}-amide |
| 329 | 431 | N-{4-[3-(5-Chloro-2,4-dimethoxy-phenyl)-thioureido]-naphthalen-1-yl}-acetamide |
| 330 | 416 | Furan-2-carboxylic acid {4-[3-(3-chloro-4-dimethylamino-phenyl)-thioureido]-phenyl}-amide |
| 331 | 561 | Furan-2-carboxylic acid [4-(3-{4-[(1-benzyl-pyrrolidin-3-yl)-methyl-amino]-3-chloro-phenyl}-thioureido)-phenyl]-amide |
| 332 | 513 | N-[4-(3-{3-Chloro-4-[methyl-(1-methyl-pyrrolidin-3-yl)-amino]-phenyl}-thioureido)-phenyl)-2-fluoro-benzamide |
| 333 | 463 | N-{4-[3-(5-Chloro-2-methoxy-4-methyl-phenyl)-thioureido]-phenyl}-2,6-difluoro-benzamide |
| 334 | 420 | N-(4-{3-[3-Chloro-4-(1-methyl-pyrrolidin-3-yloxy)-phenyl]-thioureido}-phenyl)-acetamide |
| 335 | 434 | N-(4-{3-[3-Chloro-4-(1--methyl-piperidin-4-yloxy)-phenyl]-thioureido}-phenyl)-acetamide |
| 336 | 422 | N-(4-{3-[3-Chloro-4-(3-dimethylamino-propoxy)-phenyl]-thioureido}-phenyl)-acetamide |
| 337 | 425 | 2-Acetylamino-5-[3-(5-chloro-2,4-dimethoxy-phenyl)-thioureido]-benzoic acid |
| 338 | 505 | 5-[3-(5-Chloro-2,4-dimethoxy-phenyl)-thioureido]-2-(2-fluoro-benzoylamino)-benzoic acid |
| 339 | 477 | 5-[3-(5-Chloro-2,4-dimethoxy-phenyl)-thioureido]-2-[(furan-2-carbonyl)-amino]-benzoic acid |
| 340 | 545 | N-[4-(3-{3-Chloro-4-[methyl-(1-methyl-piperidin-4-yl)-amino]-phenyl}-thioureido)-phenyl]-2,6-difluoro-benzamide |
| 341 | 503 | [1,2,3]Thiadiazole-4-carboxylic acid[4-(3-{3-Chloro-4-[methyl-(1-methyl-pyrrolidin-3-yl)-amino]-phenyl}-thioureido)-phenyl]-amide |
| 342 | 443 | N-{4-[3-(3-Chloro-4-methylsulfanyl-phenyl)-thioureido]-phenyl}-2-methyl-benzamide |
| 343 | 408 | N-(4-(3-[3-Chloro-4-(2-dimethylamino-ethoxy)-phenyl]-thioureido}-phenyl)-acetamide |
| 344 | 499 | Furan-2-carboxylic acid [4-(3-{3-chloro-4-[methyl-(1-methyl-piperidin-4-yl)-amino]-phenyl}-thioureido)- phenyl]-amide |
| 345 | 419 | N-{4-[3-(3-Chloro-4-cyclohexyloxy-phenyl)-thioureido]-phenyl}-acetamide |
| 346 | 440 | N-{4-[3-(3-Chloro-4-dimethylamino-phenyl)-thioureido]-phenyl}-2-methyl-benzamide |
| 347 | 493 | N-{4-[3-(5-Chloro-2,4-dimethoxy-phenyl)-thioureido]-3-methyl-phenyl}-2,6-difluoro-benzamide |
| 348 | 462 | N-{4-[3-(3-Chloro-4-dimethylamino-phenyl)-thioureido]-phenyl}-2,6-difluoro-benzamide |
| 349 | 531 | N-[4-(3-{3-Chloro-4-[methyl-(1-methyl-pyrrolidin-3-yl)-amino]-phenyl}-thioureido)-phenyl]-2,6-difluoro-benzamide |
| 350 | 427 | Pyridine-2-carboxylic acid {4-[3-(3-chloro-dimethylamino-phenyl)-thioureido]-phenyl}-amide |
| 351 | 430 | Pyridine-2-carboxylic acid {4-[3-(3-chloro-4-methylsulfanyl-phenyl)-thioureido]-phenyl}-amide |
| 352 | 428 | Pyridine-2-carboxylic acid {4-[3-(5-chloro-2-methoxy-4-methyl-phenyl)-thioureido]-phenyl}-amide |
| 353 | 417 | Furan-2-carboxylic acid {4-[3-(5-chloro-2-methoxy-4-methyl-phenyl)-thioureido]-phenyl}-amide |

-continued

| EX. NO. | M + H | COMPOUND NAME |
|---|---|---|
| 354 | 496 | Pyridine-2-carboxylic acid [4-(3-{3-chloro-4-[methyl-(1-methyl-pyrrolidin-3-yl)-amino]-phenyl}-thioureido)-phenyl]-amide |
| 355 | 495 | N-{3-Chloro-4-[3-(5-chloro-2,4-dimethoxy-phenyl)-thioureido]-phenyl}-2-fluoro-benzamide |
| 356 | 467 | Furan-2-carboxylic acid {3-chloro-4-[3-(5-chloro-2,4-dimethoxy-phenyl)-thioureido]-phenyl}-amide |
| 357 | 515 | N-{4-[3-(3-Chloro-4-cyclohexylsulfanyl-phenyl)-thioureido]-phenyl}-2-fluoro-benzamide |
| 358 | 449 | N-{4-[3-(5-Chloro-2,4-dimethoxy-phenyl)-thioureido]-3-trifluoromethyl-phenyl}-acetamide |
| 359 | 529 | N-{4-[3-(5-Chloro-2,4-dimethoxy-phenyl)-thioureido]-3-trifluoromethyl-phenyl}-2-fluoro-benzamide |
| 360 | 421 | N-{4-[3-(4-Acetylamino-phenyl)-thioureido]-2-chloro-phenyl}-2-dimethyl-amino-acetamide |
| 361 | 473 | Furan-2-carboxylic acid (4-{3-[3-chloro-4-(2-dimethylamino-acetylamino)-phenyl]-thioureido}-phenyl)-amide |
| 362 | 501 | N-(4-{3-[3-Chloro-4-(2-dimethylamino-acetylamino)-phenyl]-thioureido}-phenyl)-2-fluoro-benzamide |
| 363 | 461 | N-{4-[3-(4-Acetylamino-phenyl)-thioureido]-2-chloro-phenyl)-2-piperidin-1-yl-acetamide |
| 364 | 541 | N-(4-{3-[3-Chloro-4-(2-piperidin-1-yl-acetylamino)-phenyl]-thioureido}-phenyl)-2-fluoro-benzamide |
| 365 | 513 | Furan-2-carboxylic acid (4-{3-[3-chloro-4-(2-piperidin-1-yl-acetylamino)-phenyl]-thioureido}-phenyl)-amide |
| 366 | 463 | N-{4-[3-(4-Acetylamino-phenyl)-thioureido]-2-chloro-phenyl}-2-morpholin-4-yl-acetamide |
| 367 | 543 | N-(4-{3-[3-Chloro-4-(2-morpholin-4-yl-acetylamino)-phenyl]-thioureido}-phenyl)-2-fluoro-benzamide |
| 368 | 515 | Furan-2-carboxylic acid (4-{3-[3-chloro-4-(2-morpholin-4-yl-acetylamino)-phenyl]-thioureido}-phenyl)-amide |
| 369 | 414 | N-{4-[3-(3-Chloro-4-methanesulfonylamino-phenyl)-thioureido]-phenyl}-acetamide |
| 370 | 494 | N-{4-[3-(3-Chloro-4-methanesulfonylamino-phenyl)-thioureido]-phenyl}-2-fluoro-benzamide |
| 371 | 466 | Furan-2-carboxylic acid {4-[3-(3-chloro-4-methanesulfonylamino-phenyl)-thioureido]-phenyl}-amide |
| 372 | 481 | N-{4-[3-(4-Acetylamino-phenyl)-thioureido]-2-chloro-phenyl}-2-(2-dimethy-lamino-ethylsulfanyl)-acetamide |
| 373 | 561 | N-(4-{3-{3-Chloro-4-[2-(2-dimethylamino-ethylsulfanyl)-acetylamino]-phenyl}-thioureido)-phenyl}-2-fluoro-benzamide |
| 374 | 585 | N-{4-(3-{4-[(1-Benzyl-pyrrolidin-3-yl)-methyl-amino]-3-chloro-phenyl}-thioureido)-phenyl}-2-methyl-benzamide |
| 375 | 523 | N-[4-(3-{3-Chloro-4-[methyl-(1-methyl-piperidin-4-yl)-amino]-phenyl})-thioureido)-phenyl}-2-methyl-benzamide |
| 376 | 510 | Pyridine-2-carboxylic acid [4-(3-{3-chloro-4-[methyl-(1-methyl-piperidin-4-yl)-amino]-phenyl}-thioureido)-phenyl]-amide |
| 377 | 347 | N-{4-[3-(3-Chloro-4-vinyl-phenyl)-thioureido]-phenyl}-acetamide |
| 378 | 441 | Furan-2-carboxylic acid {4-[3-(4-chloro-3-trifluoromethyl-phenyl)-thioureido]-phenyl}-amide |
| 379 | 452 | Pyridine-2-carboxylic acid {4-[3-(4-chloro-3-trifluoromethyl-phenyl)-thioureido]-phenyl}-amide |
| 380 | 487 | N-{4-[3-(4-Chloro-3-trifluoromethyl-phenyl)-thioureido]-phenyl}-2,6-difluoro-benzamide |
| 381 | 486 | N-{4-[3-(5-Chloro-2,4-dimethoxy-phenyl)-thioureido]-3-cyano-phenyl}-2-fluoro-benzamide |
| 382 | 458 | Furan-2-carboxylic acid {4-[3-(5-chloro-2,4-dimethoxy-phenyl)-thioureido]-cyano-phenyl}-amide |
| 383 | 406 | N-{4-[3-(5-Chloro-2,4-dimethoxy-phenyl)-thioureido]-3-cyano-phenyl}-acetamide |
| 384 | 395 | N-{4-[3-(5-Chloro-2,4-dimethoxy-phenyl)-2-methyl-isothioureido]-phenyl}-acetamide |
| 385 | 396 | N-{4-[3-(5-Chloro-2,4-dimethoxy-phenyl)-2-methyl-isothioureido]-phenyl}-acetamide |
| 386 | 461 | N-{4-[3-(3-Chloro-4-ethylsulfanyl-phenyl)-thioureido]-phenyl}-2-fluoro-benzamide |
| 387 | 489 | N-{4-[3-(4-Butylsulfanyl-3-chloro-phenyl)-thioureido]-phenyl}-2-fluoro-benzamide |
| 388 | 411 | N-{4-[3-(5-Chloro-2,4-dimethoxy-phenyl)-thioureido]-3-methoxy-phenyl}-acetamide |
| 389 | 491 | N-{4-[3-(5-Chloro-2,4-dimethoxy-phenyl)-thioureido]-3-methoxy-phenyl}-2-fluoro-benzamide |
| 390 | 463 | Furan-2-carboxylic acid {4-[3-(5-chloro-2,4-dimethoxy-phenyl)-thioureido]-3-methoxy-phenyl}-amide |
| 391 | 531 | [1,2,3]Thiadiazole-4-carboxylic acid (4-{3-[3-chloro-4-(2-piperidin-1-yl-acetyl-amino)-phenyl]-thioureido}-phenyl)-amide |
| 392 | 481 | N-{4-[3-(3-Chloro-4-methanesulfinyl-phenyl)-thioureido]-phenyl}-2,6-difluoro-benzamide |
| 393 | 497 | N-{4-[3-(3-Chloro-4-methanesulfonyl-phenyl)-thioureido]-phenyl}-2,6-difluoro-benzamide |
| 394 | 459 | N-{4-[3-(5-Chloro-2-methoxy-4-methyl-phenyl)-thioureido]-2-methyl-phenyl}-2-fluoro-benzamide |
| 395 | 429 | N-{4-[3-(3-Chloro-4-methyl-phenyl)-thioureido]-2-methyl-phenyl}-2-fluoro-benzamide |
| 396 | 533 | Furan-2-carboxylic acid [4-(3-{3-chloro-4-[2-(2-dimethylamino-ethylsulfanyl)-acetylamino]-phenyl}-thioureido)-phenyl]-amide |
| 397 | 458 | N-{4-[3-(4-Acetylamino-3-chloro-phenyl)-thioureido]-phenyl}-2-fluoro-benzamide |
| 398 | 460 | [2-Chloro-4-(3-{4-[(furan-2-carbonyl)-amino]-phenyl}-thioureido)-phenyl]-carbamic acid ethyl ester |
| 399 | 488 | (2-Chloro-4-{3-[4-(2-fluoro-benzoylamino)-phenyl]-thioureido}-phenyl)-carbamic acid ethyl ester |
| 400 | 440 | N-{4-[3-(4-Acetylamino-phenyl)-thioureido]-2-chloro-phenyl}-benzamide |
| 401 | 520 | N-{4-[({[4-(Benzoylamino)-3-chloro-phenyl]-amino}-thioxomethyl)-amino]-phenyl}-2-fluoro-benzamide |
| 402 | 529 | N-{4-[3-(5-Chloro-2,4-dimethoxy-phenyl)-thioureido]-2-trifluoromethyl-phenyl}-2-fluoro-benzamide |
| 403 | 492 | Furan-2-carboxylic acid {4-[3-(4-benzoylamino-3-chloro-phenyl)-thioureido]-phenyl}-amide |
| 404 | 416 | N-{4-[3-(4-Amino-3-chloro-phenyl)-thioureido]-phenyl}-2-fluoro-benzamide |
| 405 | 479 | N-{4-[3-(4-Acetylamino-phenyl)-thioureido]-2-chloro-phenyl}-2-thiomorphin-4-yl-acetamide |
| 406 | 531 | Furan-2-carboxylic acid (4-{3-[3-chloro-4-(2-thiomorpholin-4-yl-acetylamino)-phenyl]-thioureido}-phenyl)-amide |
| 407 | 559 | N-(4-{3-[3-Chloro-4-(2-thiomorpholin-4-yl-acetylamino)-phenyl]-thioureido}-phenyl)-2-fluoro-benzamide |
| 408 | 461 | N-{4-[3-(3-Chloro-4-methylsulfanyl-phenyl)-thioureido]-2-methyl-phenyl}-2-fluoro-benzamide |
| 409 | 430 | Furan-2-carboxylic acid {4-[3-(4-acetylamino-3-chloro-phenyl)-thioureido]-phenyl}-amide |
| 410 | 477 | N-{4-[3-(4-Acetylamino-phenyl)-thioureido]-2-chloro-phenyl}-2-dipropylamino-acetamide |
| 411 | 529 | Furan-2-carboxylic acid (4-{3-[3-chloro-4-(2-dipropylamino-acetylamino)-phenyl]-thioureido}-phenyl)-amide |
| 412 | 449 | N-{4-[3-(4-Acetylamino-phenyl)-thioureido]-2-chloro-phenyl}-2-diethyl-amino-acetamide |
| 413 | 501 | Furan-2-carboxylic acid (4-{3-[3-chloro-4-(2-diethylamino-acetylamino)-phenyl]-thioureido}-phenyl)-amide |
| 414 | 529 | N-(4-{3-[3-Chloro-4-(2-diethylamino-acetylamino)-phenyl]-thioureido}-phenyl)-2-fluoro-benzamide |
| 415 | 447 | N-{4-[3-(4-Acetylamino-phenyl)-thioureido]-2-chloro-phenyl}-2-pyrrolidin-1-yl-acetamide |
| 416 | 499 | Furan-2-carboxylic acid (4-{3-[3-chloro-4-(2-pyrrolidin-1-yl-acetylamino)-phenyl]-thioureido}-phenyl)-amide |
| 417 | 527 | N-(4-{3-(3-[3-Chloro-4-(2-pyrrolidin-1-yl-acetylamino)-phenyl]-thioureido}-phenyl)-2-fluoro-benzamide |
| 418 | 475 | N-{4-[3-(5-Chloro-2-methoxy-4-methyl-phenyl)-thioureido]-3-methoxy-phenyl}-2-fluoro-benzamide |
| 419 | 445 | N-{4-[3-(3-Chloro-4-methyl-phenyl)-thioureido]-3-methoxy-phenyl}-2-fluoro-benzamide |
| 420 | 477 | N-{4-[3-(3-Chloro-4-methylsulfanyl-phenyl)-thioureido]-3-methoxy-phenyl}-2-fluoro-benzamide |
| 421 | 388 | Furan-2-carboxylic acid {4-[3-(4-amino-3-chloro-phenyl)-thioureido]-phenyl}-amide |
| 422 | 527 | Furan-2-carboxylic acid (4-{3-[4-(2-azepan-1-yl-acetylamino)-3-chloro-phenyl]-thioureido}-phenyl)-amide |
| 423 | 555 | N-(4-{3-[4-(2-Azepan-1-yl-acetylamino)-3-chloro-phenyl]-thioureido}-phenyl)-2-fluoro-benzamide |
| 424 | 527 | Furan-2-carboxylic acid [4-(3-{3-chloro-4-[2-(2-methyl-piperidin-1-yl)-acetyl-amino]-phenyl}-thioureido)-phenyl]-amide |
| 425 | 555 | N-[4-(3-{3-Chloro-4-[2-(2-methyl-piperidin-1-yl)-acetylamino]-phenyl}-thioureido)-phenyl]-2-fluoro-benzamide |
| 426 | 339 | Furan-2-carboxylic acid [4-(3-pyridin-2-yl-thioureido)-phenyl]-amide |
| 427 | 339 | Furan-2-carboxylic acid [4-(3-pyridin-4-yl-thioureido)-phenyl]-amide |
| 428 | 367 | 2-Fluoro-N-[4-(3-pyridin-3-yl-thioureido)-phenyl]-benzamide |
| 429 | 339 | Furan-2-carboxylic acid [4-(3-pyridin-3-yl-thioureido)-phenyl]-amide |

-continued

| EX. NO. | M + H | COMPOUND NAME |
|---|---|---|
| 430 | 353 | Furan-2-carboxylic acid {4-[3-(3-amino-phenyl)-thioureido]-phenyl}-amide |
| 431 | 406 | Furan-2-carboxylic acid {4-[3-(3-trifluoromethyl-phenyl)-thioureido]-phenyl}-amide |
| 432 | 380 | 2-Fluoro-N-[4-(3-m-tolyl-thioureido)-phenyl]-benzamide |
| 433 | 434 | 2-Fluoro-N-{4-[3-(3-trifluoromethyl-phenyl)-thioureido]-phenyl}-benzamide |
| 434 | 381 | N-{4-[3-(3-Amino-phenyl)-thioureido]-phenyl}-2-fluoro-benzamide |
| 435 | 388 | Furan-2-carboxylic acid {4-[3-(3-amino-5-chloro-phenyl)-thioureido]-phenyl}-amide |
| 436 | 352 | Furan-2-carboxylic acid [4-(3-m-tolyl-thioureido)-phenyl]-amide |
| 437 | 416 | N-{4-[3-(2-Amino-5-chloro-phenyl)-thioureido]-phenyl}-2-fluoro-benzamide |
| 438 | 571 | (2-Chloro-4-{3-[4-(2-fluoro-benzoylamino)-phenyl]-thioureido}-phenyl)-carbamic acid 2-piperidin-1-yl-ethyl ester |
| 439 | 543 | [2-Chloro-4-(3-{4-[(furan-2-carbonyl)-amino]-phenyl}-thioureido)-phenyl]-carbamic acid 2-piperidin-1-yl-ethyl ester |
| 440 | 388 | Furan-2-carboxylic acid {4-[3-(2-amino-5-chloro-phenyl)-thioureido]-phenyl}-amide |
| 441 | 363 | Furan-2-carboxylic acid {4-[3-(3-cyano-phenyl)-thioureido]-phenyl}-amide |
| 442 | 416 | N-{4-[3-(3-Amino-5-chloro-phenyl)-thioureido]-phenyl}-2-fluoro-benzamide |
| 443 | 367 | 2-Fluoro-N-[4-(3-pyridin-2-yl-thioureido)-phenyl]-benzamide |
| 444 | 367 | 2-Fluoro-N-[4-(3-pyridin-4-yl-thioureido)-phenyl]-benzamide |
| 445 | 374 | Furan-2-carboxylic acid {4-[3-(6-chloro-pyridin-3-yl)-thioureido]-phenyl}-amide |
| 446 | 388 | Furan-2-carboxylic acid {4-[3-(2-amino-3-chloro-phenyl)-thioureido]-phenyl}-amide |
| 447 | 396 | Furan-2-carboxylic acid {4-[3-(3-hydrazinocarbonyl-phenyl)-thioureido]-phenyl}-amide |
| 448 | 410 | 2-Fluoro-N-(4-{3-[3-(1-hydroxy-ethyl)-phenyl]-thioureido}-phenyl)-benzamide |
| 449 | 414 | [1,2,3]Thiadiazole-4-carboxylic acid {4-[3-(3-hydrazinocarbonyl-phenyl)-thioureido]-phenyl}-amide |
| 450 | 399 | [1,2,3]Thiadiazole-4-carboxylic acid {4-[3-(3-isopropyl-phenyl)-thioureido]-phenyl}-amide |
| 451 | 380 | Furan-2-carboxylic acid {4-[3-(3-isopropyl-phenyl)-thioureido]-phenyl}-amide |
| 452 | 409 | 2-Fluoro-N-{4-[3-(3-isopropyl-phenyl)-thioureido]-phenyl}-benzamide |
| 453 | 381 | [1,2,3]Thiadiazole-4-carboxylic acid {4-[3-(3-cyano-phenyl)-thioureido]-phenyl}-amide |
| 454 | 410 | N-{4-[3-(3-Dimethylamino-phenyl)-thioureido]-phenyl}-2-fluoro-benzamide |
| 455 | 381 | Furan-2-carboxylic acid {4-[3-(3-dimethylamino-phenyl)-thioureido]-phenyl}-amide |
| 456 | 370 | [1,2,3]Thiadiazole-4-carboxylic acid [4-(3-m-tolyl-thioureido)-phenyl]-amide |
| 457 | 424 | [1,2,3]Thiadiazole-4-carboxylic acid {4-[3-(3-trifluoromethyl-phenyl)-thioureido]-phenyl}-amide |
| 458 | 479 | N-{3-Chloro-4-[3-(5-chloro-2-methoxy-4-methyl-phenyl)-thioureido]-phenyl}-2-fluoro-benzamide |
| 459 | 449 | N-{3-Chloro-4-[3-(3-chloro-4-methyl-phenyl)-thioreido]-phenyl}-2-fluoro-benzamide |
| 460 | 481 | N-{3-Chloro-4-[3-(3-chloro-4-methylsulfanyl-phenyl)-thioureido]-phenyl}-2-fluoro-benzamide |
| 461 | 391 | N-{4-[3-(3-Cyano-phenyl)-thioureido]-phenyl}-2-fluoro-benzamide |
| 462 | 395 | Furan-2-carboxylic acid {4-[3-(3-acetylamino-phenyl)-thioureido]-phenyl}-amide |
| 463 | 424 | 2-Fluoro-N-{4-[3-(3-hydrazinocarbonyl-phenyl)-thioureido]-phenyl}-benzamide |
| 464 | 400 | [1,2,3]Thiadiazole-4-carboxylic acid (4-{3-[3-(1-hydroxy-ethyl)-phenyl]-thioureido}-phenyl)-amide |
| 465 | 434 | N-{4-[3-(2-Amino-3-chloro-phenyl)-thioureido]-phenyl}-2,6-difluoro-benzamide |
| 466 | 406 | [1,2,3]Thiadiazole-4-carboxylic acid {4-[3-(3-amino-5-chloro-phenyl)-thioureido]-phenyl}-amide |
| 467 | 398 | Furan-2-carboxylic acid {4-[3-(3,5-dimethoxy-phenyl)-thioureido]-phenyl}-amide |
| 468 | 416 | [1,2,3]Thiadiazole-4-carboxylic acid {4-[3-(3,5-dimethoxy-phenyl)-thioureido]-phenyl}-amide |
| 469 | 454 | 5-(3-{4-[(Furan-2-carbonyl)-amino]-phenyl}-thioureido)-isophthalic acid dimethyl ester |
| 470 | 434 | Isoxazole-5-carboxylic acid {4-[3-(5-chloro-2,4-dimethoxy-phenyl)-thioureido]-phenyl}-amide |
| 471 | 392 | [1,2,3]Thiadiazole-4-carboxylic acid {4-[3-(6-chloro-pyridin-3-yl)-thioureido]-phenyl}-amide |
| 472 | 382 | Furan-2-carboxylic acid (4-{3-[3-(1-hydroxy-ethyl)-phenyl]-thioureido}-phenyl)-amide |
| 473 | 368 | Furan-2-carboxylic acid {4-[3-(3-methoxy-phenyl)-thioureido]-phenyl}-amide |
| 474 | 354 | Furan-2-carboxylic acid {4-[3-(3-hydroxy-phenyl)-thioureido]-phenyl}-amide |
| 475 | 382 | 2-Fluoro-N-{4-[3-(3-hydroxy-phenyl)-thioureido]-phenyl}-benzamide |
| 476 | 396 | 2-Fluoro-N-{4-[3-(3-hydroxymethyl-phenyl)-thioureido]-phenyl}-benzamide |
| 477 | 423 | N-{4-[3-(3-Acetylamino-phenyl)-thioureido]-phenyl}-2-fluoro-benzamide |
| 478 | 413 | [1,2,3]Thiadiazole-4-carboxylic acid {4-[3-(3-acetylamino-phenyl)-thioureido]-phenyl}-amide |
| 479 | 400 | [1,2,3]Thiadiazole-4-carboxylic acid {4-[3-(3-dimethylamino-phenyl)-thioureido]-phenyl}-amide |
| 480 | 340 | Furan-2-carboxylic acid [4-(3-pyrimidin-4-yl-thioureido)-phenyl]-amide |
| 481 | 378 | Furan-2-carboxylic acid {4-[3-(1H-indazol-5-yl)-thioureido]-phenyl}-amide |
| 482 | 395 | Furan-2-carboxylic acid [4-(3-benzothiazol-5-yl-thioureido)-phenyl]-amide |
| 483 | 406 | 2-Fluoro-N-{4-[3-(1H-indazol-5-yl)-thioureido]-phenyl}-benzamide |
| 484 | 424 | N-[4-(3-Benzothiazol-5-yl-thioureido)-phenyl]-2-fluoro-benzamide |
| 485 | 473 | 5-(3-{4-[([1,2,3]Thiadiazole-4-carbonyl)-amino]-phenyl}-thioureido)-isophthalic acid dimethyl ester |
| 486 | 442 | Furan-2-carboxylic acid (4-{3-[4-(1-azido-ethyl)-3-chloro-phenyl]-thioureido}-phenyl)-amide |
| 487 | 396 | 2-Fluoro-N-{4-[3-(3-methoxy-phenyl)-thioureido]-phenyl}-benzamide |
| 488 | 368 | Furan-2-carboxylic acid {4-[3-(3-hydroxymethyl-phenyl)-thioureido]-phenyl}-amide |
| 489 | 416 | Furan-2-carboxylic acid {4-[3-(5-chloro-2-dimethylamino-phenyl)-thioureido]-phenyl}-amide |
| 490 | 444 | N-{4-[3-(5-Chloro-2-dimethylamino-phenyl)-thioureido]-phenyl}-2-fluoro-benzamide |
| 491 | 506 | [3-Chloro-5-(3-{4-[([1,2,3]thiadiazole-4-carbonyl)-amino]-phenyl}-thioureido)-phenyl]-carbamic acid tert-butyl ester |
| 492 | 470 | N-(4-{3-[4-(1-Azido-ethyl)-3-chloro-phenyl]-thioureido}-phenyl)-2-fluoro-benzamide |
| 493 | 337 | Furan-2-carboxylic acid [4-(1H-thiazolo[5,4-b]pyridin-2-ylideneamino)-phenyl]-amide |
| 494 | 378 | Furan-2-carboxylic acid {4-[3-(1H-benzoimidazol-5-yl)-thioureido]-phenyl}-amide |
| 495 | 392 | Furan-2-carboxylic acid {4-[3-(2-methyl-1H-benzoimidazol-5-yl)-thioureido]-phenyl}-amide |
| 496 | 406 | N-{4-[3-(1H-Benzoimidazol-5-yl)-thioureido]-phenyl}-2-fluoro-benzamide |
| 497 | 420 | 2-Fluoro-N-{4-[3-(2-methyl-1H-benzoimidazol-5-yl)-thioureido]-phenyl}-benzamide |
| 498 | 452 | [1,2,3]Thiadiazole-4-carboxylic acid {5-[3-(5-chloro-2,4-dimethoxy-phenyl)-thioureido]-pyridin-2-yl}-amide |
| 499 | 445 | Pyridine-2-carboxylic acid {5-[3-(5-chloro-2,4-dimethoxy-phenyl)-thioureido]-pyridin-2-yl}-amide |
| 500 | 434 | [1,2,3]Thiadiazole-4-carboxylic acid {4-[3-(5-chloro-2-dimethylamino-phenyl)-thioureido]-phenyl}-amide |
| 501 | 484 | [1,2,3]Thiadiazole-4-carboxylic acid (4-{3-[4-(2-amino-pyrimidin-4-yl)-3-chloro-phenyl]-thioureido}-phenyl)-amide |
| 502 | 494 | N-(4-{3-[4-(2-Amino-pyrimidin-4-yl)-3-chloro-phenyl]-thioureido}-phenyl)-2-fluoro-benzamide |
| 503 | 434 | [1,2,3]Thiadiazole-4-carboxylic acid {4-[3-(3-chloro-2-dimethylamino-phenyl)-thioureido]-phenyl}-amide |
| 504 | 462 | N-{4-[3-(3-Chloro-2-dimethylamino-phenyl)-thioureido]-phenyl}-2,6-difluoro-benzamide |
| 505 | 416 | Furan-2-carboxylic acid {4-[3-(3-chloro-2-dimethylamino-phenyl)-thioureido]-phenyl}-amide |

-continued

| EX. NO. | M + H | COMPOUND NAME |
|---|---|---|
| 506 | 445 | Pyridine-2-carboxylic acid {6-[3-(5-chloro-2,4-dimethoxy-phenyl)-thioureido]-pyridin-3-yl}-amide |
| 507 | 462 | N-{6-[3-(5-Chloro-2,4-dimethoxy-phenyl)-thioureido]-pyridin-3-yl}-2-fluoro-benzamide |
| 508 | 482 | [1,2,3]Thiadiazole-4-carboxylic acid {4-[3-(3-iodo-phenyl)-thioureido]-phenyl}-amide |
| 509 | 413 | [1,2,3]Thiadiazole-4-carboxylic acid {4-[3-(3-tert-butyl-phenyl)-thioureido]-phenyl}-amide |
| 510 | 387 | Furan-2-carboxylic acid {4-[3-(3-chloro-benzyl)-thioureido]-phenyl}-amide |
| 511 | 415 | N-{4-[3-(3-Chloro-benzyl)-thioureido]-phenyl}-2-fluoro-benzamide |
| 512 | 434 | Furan-2-carboxylic acid {6-[3-(5-chloro-2,4-dimethoxy-phenyl)-thioureido]-pyridin-3-yl}-amide |
| 513 | 435 | [1,2,3]Thiadiazole-4-carboxylic acid {4-[3-(3-bromo-phenyl)-thioureido]-phenyl}-amide |
| 514 | 452 | [1,2,3]Thiadiazole-4-carboxylic acid {6-[3-(5-chloro-2,4-dimethoxy-phenyl)-thioureido]-pyridin-3-yl}-amide |
| 515 | 426 | [1,2,3]Thiadiazole-4-carboxylic acid {5-[3-(3,5-dichloro-phenyl)-thioureido]-pyridin-2-yl}-amide |
| 516 | 474 | Furan-2-carboxylic acid {4-[3-(3,5-bis-trifluoromethyl-phenyl)-thioureido]-phenyl}-amide |
| 517 | 502 | N-{4-[3-(3,5-Bis-trifluoromethyl-phenyl)-thioureido]-phenyl}-2-fluoro-benzamide |
| 518 | 450 | N-{4-[3-(4-Amino-3,5-dichloro-phenyl)-thioureido]-phenyl}-2-fluoro-benzamide |
| 519 | 539 | N-{4-[3-(4-Amino-3,5-dibromo-phenyl)-thioureido]-phenyl}-2-fluoro-benzamide |
| 520 | 392 | [1,2,3]Thiadiazole-4-carboxylic acid {4-[3-(5-chloro-pyridin-3-yl)-thioureido]-phenyl}-amide |
| 521 | 529 | [1,2,3]Thiadiazole-4-carboxylic acid {4-[3-(4-amino-3,5-dibromo-phenyl)-thioureido]-phenyl}-amide |
| 522 | 434 | [1,2,3]Thiadiazole-4-carboxylic acid {4-[3-(3-chloro-5-dimethylamino-phenyl)-thioureido]-phenyl}-amide |
| 523 | 444 | N-{4-[3-(3-Chloro-5-dimethylamino-phenyl)-thioureido]-phenyl}-2-fluoro-benzamide |
| 524 | 416 | Furan-2-carboxylic acid {4-[3-(3-chloro-5-dimethylamino-phenyl)-thioureido]-phenyl}-amide |
| 525 | 436 | [1,2,3]Thiadiazole-4-carboxylic acid {4-[3-(5-bromo-pyridin-3-yl)-thioureido]-phenyl}-amide |
| 526 | 379 | Furan-2-carboxylic acid {4-[3-(1H-benzotriazol-5-yl)-thioureido]-phenyl}-amide |
| 527 | 425 | N-{4-[3-(1H-Benzotriazol-5-yl)-thioureido]-phenyl}-2,6-difluoro-benzamide |
| 528 | 388 | N-[4-({[2-(3-Chloro-phenyl)-hydrazino]-thioxomethyl}-amino)-phenyl]-furan-2-carboxamide |
| 529 | 416 | N-[4-({[2-(3-Chloro-phenyl)-hydrazino]-thioxomethyl}-amino)-phenyl]-2-fluoro-benzamide |
| 530 | 456 | Furan-2-carboxylic acid {4-[3-(2-amino-3-chloro-5-trifluoromethyl-phenyl)-thioureido]-phenyl}-amide |
| 531 | 513 | N-{4-[3-(3-Bromo-5-trifluoromethyl-phenyl)-thioureido]-phenyl}-2-fluoro-benzamide |
| 532 | 503 | [1,2,3]Thiadiazole-4-carboxylic acid {4-[3-(3-bromo-5-trifluoromethyl-phenyl)-thioureido]-phenyl}-amide |
| 533 | 374 | {4-[(Furan-2-carbonyl)-amino]-phenyl}-thiocarbamic acid O-(3-chloro-phenyl)ester |
| 534 | 474 | [1,2,3]Thiadiazole-4-carboxylic acid {4-[3-(2-amino-3-chloro-5-trifluoro-methyl-phenyl)-thioureido]-phenyl}-amide |
| 535 | 508 | [1,2,3]Thiadiazole-4-carboxylic acid {4-[3-(3-piperidin-1-yl-5-trifluoromethyl-phenyl)-thioureido]-phenyl}-amide |
| 536 | 380 | N-[4-(3-Benzyl-thioureido)-phenyl]-2-fluoro-benzamide |
| 537 | 439 | [1,2,3]Thiadiazole-4-carboxylic acid {4-[3-(3,4-dichloro-benzyl)-thioureido]-phenyl}-amide |
| 538 | 449 | N-{4-[3-(3,4-Dichloro-benzyl)-thioureido]-phenyl}-2-fluoro-benzamide |
| 539 | 370 | [1,2,3]Thiadiazole-4-carboxylic acid [4-(3-benzyl-thioureido)-phenyl]-amide |
| 540 | 424 | N-[4-(3-Benzo[1,3]dioxol-5-ylmethyl-thioureido)-phenyl]-2-fluoro-benzamide |
| 541 | 414 | [1,2,3]Thiadiazole-4-carboxylic acid [4-(3-benzo[1,3]dioxol-5-ylmethyl-thioureido)-phenyl]-amide |
| 542 | 506 | [1,2,3]Thiadiazole-4-carboxylic acid {4-[3-(3,5-bis-trifluoromethyl-benzyl)-thioureido]-phenyl}-amide |
| 543 | 516 | N-{4-[3-(3,5-Bis-trifluoromethyl-benzyl)-thioureido]-phenyl}-2-fluoro-benzamide |
| 544 | 352 | Furan-2-carboxylic acid [4-(3-benzyl-thioureido)-phenyl]-amide |
| 545 | 421 | Furan-2-carboxylic acid {4-[3-(3,4-dichloro-benzyl)-thioureido]-phenyl}-amide |
| 546 | 396 | Furan-2-carboxylic acid [4-(3-benzo[1,3]dioxol-5-ylmethyl-thioureido)-phenyl]-amide |
| 547 | 488 | Furan-2-carboxylic acid {4-[3-(3,5-bis-trifluoromethyl-benzyl)-thioureido]-phenyl}-amide |
| 548 | 503 | [1,2,3]Thiadiazole-4-carboxylic acid {4-[3-(4-bromo-3-trifluoromethyl-phenyl)-thioureido]-phenyl}-amide |
| 549 | 529 | N-{4-[3-(3-Bromo-4-trifluoromethoxy-phenyl)-thioureido]-phenyl}-2-fluoro-benzamide |
| 550 | 519 | [1,2,3]Thiadiazole-4-carboxylic acid {4-[3-(3-bromo-4-trifluoromethoxy-phenyl)-thioureido]-phenyl}-amide |
| 551 | 473 | Furan-2-carboxylic acid {4-[3-(3-chloro-4-trifluoromethylsulfanyl-phenyl)-thioureido]-phenyl}-amide |
| 552 | 412 | 2-Fluoro-N-(4-{3-[2-(3-fluoro-phenyl)-ethyl]-thioureido}-phenyl)-benzamide |
| 553 | 412 | 2-Fluoro-N-(4-{3-[2-(4-fluoro-phenyl)-ethyl]-thioureido}-phenyl)-benzamide |
| 554 | 402 | [1,2,3]Thiadiazole-4-carboxylic acid (4-{3-[2-(3-fluoro-phenyl)-ethyl]-thioureido}-phenyl)-amide |
| 555 | 402 | [1,2,3]Thiadiazole-4-carboxylic acid (4-{3-[2-(4-fluoro-phenyl)-ethyl]-thioureido}-phenyl)-amide |
| 556 | 495 | [1,2,3]Thiadiazole-4-carboxylic acid (4-{3-[3-(2-methyl-butyl)-5-trifluoro-methyl-phenyl]-thioureido}-phenyl)-amide |
| 557 | 481 | [1,2,3]Thiadiazole-4-carboxylic acid {4-[3-(3-isobutyl-5-trifluoromethyl-phenyl)-thioureido]-phenyl}-amide |
| 558 | 523 | [1,2,3]Thiadiazole-4-carboxylic acid (4-{3-[3-(4-methyl-piperazin-1-yl)-5-trifluoro-methyl-phenyl]-thioureido}-phenyl)-amide |
| 559 | 510 | [1,2,3]Thiadiazole-4-carboxylic acid {4-[3-(3-morpholin-4-yl-5-trifluoromethyl-phenyl)-thioureido]-phenyl}-amide |
| 560 | 494 | [1,2,3]Thiadiazole-4-carboxylic acid {4-[3-(3-pyrrolidin-1-yl-5-trifluoromethyl-phenyl)-thioureido]-phenyl}-amide |
| 561 | 384 | Furan-2-carboxylic acid (4-{3-[2-(4-fluoro-phenyl)-ethyl]-thioureido}-phenyl)-amide |
| 562 | 419 | [1,2,3]Thiadiazole-4-carboxylic acid (4-{3-[2-(3-chloro-phenyl)-ethyl]-thioureido}-phenyl)-amide |
| 563 | 429 | N-(4-{3-[2-(3-Chloro-phenyl)-ethyl]-thioureido}-phenyl)-2-fluoro-benzamide |
| 564 | 401 | Furan-2-carboxylic acid (4-{3-[2-(3-chloro-phenyl)-ethyl]-thioureido}-phenyl)-amide |
| 565 | 402 | [1,2,3]Thiadiazole-4-carboxylic acid (4-{3-[1-(4-fluoro-phenyl)-ethyl]-thioureido}-phenyl)-amide |
| 566 | 504 | 2-Fluoro-N-(4-[3-(3-pyrrolidin-1-yl-5-trifluoromethyl-phenyl)-thioureido]-phenyl)-benzamide |
| 567 | 477 | N-{4-[3-(3-Dimethylamino-5-trifluoromethyl-phenyl)-thioureido]-phenyl}-2-fluoro-benzamide |
| 568 | 520 | 2-Fluoro-N-{4-[3-(3-morpholin-4-yl-5-trifluoromethyl-phenyl)-thioureido]-phenyl}-benzamide |
| 569 | 533 | 2-Fluoro-N-(4-{3-[3-(4-methyl-piperazin-1-yl)-5-trifluoromethyl-phenyl]-thioureido}-phenyl)-benzamide |
| 570 | 518 | 2-Fluoro-N-{4-[3-(3-piperidin-1-yl-5-trifluoromethyl-phenyl)-thioureido]-phenyl}-benzamide |
| 571 | 468 | [1,2,3]Thiadiazole-4-carboxylic acid {4-[3-(3-dimethylamino-5-trifluoromethyl-phenyl)-thioureido]-phenyl}-amide |
| 572 | 405 | [1,2,3]Thadiazole-4-carboxylic acid {4-[3-(3-chloro-benzyl)-thioureido]-phenyl}-amide |
| 573 | 384 | Furan-2-carboxylic acid (4-{3-[2-(3-fluoro-phenyl)-ethyl]-thioureido}-phenyl)-amide |
| 574 | 366 | Furan-2-carboxylic acid [4-(3-phenethyl-thioureido)-phenyl]-amide |
| 575 | 384 | [1,2,3]Thiadiazole-4-carboxylic acid [4-(3-phenethyl-thioureido)-phenyl]-amide |
| 576 | 394 | 2-Fluoro-N-[4-(3-phenethyl-thioureido)-phenyl]-benzamide |
| 577 | 505 | 2-Fluoro-N-(4-{3-[3-(2-methyl-butyl)-5-trifluoromethyl-phenyl]-thioureido}-phenyl)-benzamide |
| 578 | 491 | 2-Fluoro-N-{4-[3-(3-isobutyl-5-trifluoromethyl-phenyl)-thioureido]-phenyl}-benzamide |
| 579 | 388 | Furan-2-carboxylic acid {4-[3-(3,5-difluoro-benzyl)-thioureido]-phenyl}-amide |
| 580 | 416 | N-{4-[3-(3,5-Difluoro-benzyl)-thioureido]-phenyl}-2-fluoro-benzamide |
| 581 | 406 | [1,2,3]Thiadiazole-4-carboxylic acid {4-[3-(3,5-difluoro-benzyl)-thioureido]-phenyl}-amide |

-continued

| EX. NO. | M + H | COMPOUND NAME |
|---|---|---|
| 582 | 421 | Furan-2-carboxylic acid {4-[3-(3,5-dichloro-benzyl)-thioureido]-phenyl}-amide |
| 583 | 449 | N-{4-[3-(3,5-Dichloro-benzyl)-thioureido]-phenyl}-2-fluoro-benzamide |
| 584 | 439 | [1,2,3]Thiadiazole-4-carboxylic acid {4-[3-(3,5-dichloro-benzyl)-thioureido]-phenyl}-amide |
| 585 | 438 | Furan-2-carboxylic acid {4-[3-(3-fluoro-5-trifluoromethyl-benzyl)-thioureido]-phenyl}-amide |
| 586 | 466 | 2-Fluoro-N-{4-[3-(3-fluoro-5-trifluoromethyl-benzyl)-thioureido]-phenyl}-benzamide |
| 587 | 456 | [1,2,3]Thiadiazole-4-carboxylic acid {4-[3-(3-fluoro-5-trifluoromethyl-benzyl)-thioureido]-phenyl}-amide |
| 588 | 384 | [1,2,3]Thiadiazole-4-carboxylic acid {4-[3-(1-phenyl-ethyl)-thioureido]-phenyl}-amide |
| 589 | 394 | 2-Fluoro-N-{4-[3-(1-phenyl-ethyl)-thioureido]-phenyl}-benzamide |
| 590 | 366 | Furan-2-carboxylic acid {4-[3-(1-phenyl-ethyl)-thioureido]-phenyl}-amide |
| 591 | 412 | 2-Fluoro-N-(4-{3-[1-(4-fluoro-phenyl)-ethyl]-thioureido}-phenyl)-benzamide |
| 592 | 384 | Furan-2-carboxylic acid (4-{3-[1-(4-fluoro-phenyl)-ethyl]-thioureido}-phenyl)-amide |
| 593 | 413 | N-{4-[3-(1-tert-Butyl-1H-imidazole-2-yl)-thioureido]-phenyl}-2-fluoro-benzamide |
| 594 | 510 | [1,2,3]Thiadiazole-4-carboxylic acid (4-{3-[3-(isobutyl-methyl-amino)-5-trifluorometbyl-phenyl]-thioureido}-phenyl)-amide |
| 595 | 510 | [1,2,3]Thiadiazole-4-carboxylic acid (4-{3-[3-(3-hydroxy-pyrrolidin-1-yl)-5-trifluoromethyl-phenyl]-thioureido}-phenyl)-amide |
| 596 | 520 | 2-Fluoro-N-(4-{3-[3-(isobutyl-methyl-amino)-5-trifluoromethyl-phenyl]-thioureido}-phenyl)-benzamide |
| 597 | 510 | [1,2,3]Thiadiazole-4-carboxylic acid (4-{3-[3-(butyl-methyl-amino)-5-trifluoromethyl-phenyl]-thioureido}-phenyl)-amide |
| 598 | 520 | N-(4-{3-[3-(Butyl-methyl-amino)-5-trifluoromethyl-phenyl]-thioureido}-phenyl)-2-fluoro-benzamide |
| 599 | 520 | [1,2,3]Thiadiazole-4-carboxylic acid (4-{3-[2-(3,5-bis-trifluoromethyl-phenyl)-ethyl]-thioureido}-phenyl)-amide |
| 600 | 442 | [1,2,3]Thiadiazole-4-carboxyiic acid {4-[3-(4-fluoro-3-trifluoromethyl-phenyl)-thioureido]-phenyl}-amide |
| 601 | 522 | [1,2,3]Thiadiazole-4-carboxylic acid {4-[3-(4-piperidin-1-yl-3-trifluoromethyl-benzyl)-thioureido]-phenyl-amide |
| 602 | 482 | [1,2,3]Thiadiazole-4-carboxylic acid {4-[3-(4-dimethylamino-3-trifluoromethyl-benzyl)-thioureido]-phenyl}-amide |
| 603 | 381 | Furan-2-carboxylic acid (4-{3-[2-(4-amino-phenyl)-ethyl]-thioureido}-phenyl)-amide |
| 604 | 445 | Furan-2-carboxylic acid (4-{3-[2-(4-bromo-phenyl)-ethyl]-thioureido}-phenyl)-amide |
| 605 | 380 | Furan-2-carboxylic acid {4-[3-(2-p-tolyl-ethyl)-thioureido]-phenyl}-amide |
| 606 | 463 | [1,2,3]Thiadiazole-4-carboxylic acid (4-{3-[2-(4-bromo-phenyl)-ethyl]-thioureido}-phenyl)-amide |
| 607 | 396 | Furan-2-carboxylic acid (4-{3-[2-(3-methoxy-phenyl)-ethyl]-thioureido}-phenyl)-amide |
| 608 | 403 | [1,2,3]Thiadiazole-4-carboxylic acid {4-[3-(1-tert-butyl-1H-imidazol-2-yl)-thioureido]-phenyl}-amide |
| 609 | 384 | Furan-2-carboxylic acid {4-[3-(1-tert-butyl-1H-imidazol-2-yl)-thioureido]-phenyl}-amide |
| 610 | 492 | N-{4-[3-(4-Dimethylamino-3-trifluoromethyl-benzyl)-thioureido]-phenyl}-2-fluoro-benzamide |
| 611 | 427 | Furan-2-carboxylic acid (4-{3-[2-(3,4-dimethoxy-phenyl)-ethyl]-thioureido}-phenyl)-amide |
| 612 | 380 | Furan-2-carboxyiic acid {4-[3-(3-phenyl-propyl)-thioureido]-phenyl}-amide |
| 613 | 399 | [1,2,3]Thiadiazole-4-carboxylic acid {4-[3-(3-phenyl-propyl)-thioureido]-phenyl}-amide |
| 614 | 502 | Furan-2-carboxylic acid (4-{3-[2-(3,5-bis-trifluoromethyl-phenyl)-ethy1]-thioureido}-phenyl)-amide |
| 615 | 550 | [1,2,3]Thiadiazole-4-carboxylic acid {4-[3-(4-iodo-3-trifluoromethyl-phenyl)-thioureido]-phenyl}-amide |
| 616 | 532 | 2-Fluoro-N-{4-[3-(4-piperidin-1-yl-3-trifluoromethyl-benzyl)-thioureido]-phenyl}-benzamide |
| 617 | 537 | [1,2,3]Thiadiazole-4-carboxylic acid (4-{3-[4-(4-methyl-piperazin-1-yl)-3-trifluoromethyl-benzyl]-thioureido}-phenyl)-amide |
| 618 | 482 | [1,2,3]Thiadiazole-4-carboxylic acid {4-[3-(3-dimethylamino-5-trifluoromethyl-benzyl)-thioureido]-phenyl}amide |
| 619 | 488 | Furan-2-carboxylic acid {4-[3-(3,5-bis-trifluoromethyl-phenyl)-thioureido-methyl]-phenyl}-amide |
| 620 | 421 | Furan-2-carboxylic acid {4-[3-(3,5-dichloro-phenyl)-thioureidomethyl]-phenyl}-amide |
| 621 | 421 | Furan-2-carboxylic acid {4-[3-(3,4-dichloro-phenyl)-thioureidomethyl]-phenyl}-amide |
| 622 | 455 | Furan-2-carboxylic acid {4-[3-(4-chloro-3-trifluoromethyl-phenyl)-thioureido-methyl]-phenyl}-amide |
| 623 | 466 | 2-Fluoro-N-{4-[3-(4-fluoro-3-trifluoromethyl-benzyl)-thioureido]-phenyl}-benzamide |
| 624 | 456 | [1,2,3]Thiadiazole-4-carboxylic acid {4-[3-(4-fluoro-3-trifluoromethyl-benzyl)-thioureido]-phenyl}-amide |
| 625 | 410 | 2-Fluoro-N-{4-[3-(2-phenoxy-ethyl)-thioureido]-phenyl}-benzamide |
| 626 | 382 | Furan-2-carboxylic acid {4-[3-(2-phenoxy-ethyl)-thioureido]-phenyl}-amide |
| 627 | 400 | [1,2,3]Thiadiazole-4-carboxylic acid {4-[3-(2-phenoxy-ethyl)-thioureido]-phenyl}-amide |
| 628 | 409 | 2-Fluoro-N-{4-[3-(3-phenyl-propyl)-thioureido]-phenyl}-benzamide |
| 629 | 425 | [1,2,3]Thiadiazole-4-carboxylic acid {4-[3-(5-trifluoromethyl-pyridin-3-yl)-thioureido]-phenyl}-amide |
| 630 | 439 | [1,2,3]Thiadiazole-4-carboxylic acid {4-[3-(3,4-dichloro-phenyl)-thioureido-methyl]-phenyl}-amide |
| 631 | 473 | [1,2,3]Thiadiazole-4-carboxylic acid {4-[3-(4-chloro-3-trifluoromethyl-phenyl)-thioureidomethyl]-phenyl}-amide |
| 632 | 381 | 2-Fluoro-N-[4-(3-pyridin-3-ylmethyl-thioureido)-phenyl]-benzamide |
| 633 | 353 | Furan-2-carboxylic acid [4-(3-pyridin-3-ylmethyl-thioureido)-phenyl]-amide |
| 634 | 371 | [1,2,3]Thiadiazole-4-carboxylic acid [4-(3-pyridin-3-ylmethyl-thioureido)-phenyl]-amide |
| 635 | 439 | [1,2,3]Thiadiazole-4-carboxylic acid {4-[3-(3,5-dichloro-phenyl)-thioureido-methyl]-phenyl}-amide |
| 636 | 492 | N-{4-[3-(3-Dimethylamino-5-trifluoromethyl-benzyl)-thioureido]-phenyl}-2-fluoro-benzamide |
| 637 | 415 | [1,2,3]Thiadiazole-4-carboxylic acid (4-{3-[2-(3-methoxy-phenyl)-ethyl]-thioureido}-phenyl)-amide |
| 638 | 399 | [1,2,3]Thiadiazole-4-carboxylic acid {4-[3-(2-p-tolyl-ethyl)-thioureido]-phenyl}-amide |
| 639 | 445 | [1,2,3]Thiadiazole-4-carboxylic acid (4-{3-[2-(3,4-dimethoxy-phenyl)-ethyl]-thioureido}-phenyl)-amide |
| 640 | 506 | [1,2,3]Thiadiazole-4-carboxylic acid {4-[3-(3,5-bis-trifluoromethyl-phenyl)-thioureidomethyl]-phenyl}-amide |
| 641 | 516 | N-{4-[3-(3,5-Bis-trifluoromethyl-phenyl)-thioureidomethyl]-phenyl}-2-fluoro-benzamide |
| 642 | 449 | N-{4-[3-(3,5-Dichloro-phenyl)-thioureidomethyl]-phenyl}-2-fluoro-benzamide |
| 643 | 449 | N-{4-[3-(3,5-Dichloro-phenyl)-thioureidomethyl]-phenyl}-2-fluoro-benzamide |
| 644 | 448 | [1,2,3]Thiadiazole-4-carboxylic acid {4-[3-(3-acetylamino-5-chloro-phenyl)-thioureido]-phenyl}-amide |
| 645 | 453 | [1,2,3]Thiadiazole-4-carboxylic acid (4-{3-[2-(3,4-dichloro-phenyl)-ethyl]-thioureido}-phenyl)-amide |
| 646 | 413 | [1,2,3]Thiadiazole-4-carboxylic acid {4-[3-(1-methyl-3-phenyl-propyl)-thioureido]-phenyl}-amide |
| 647 | 463 | [1,2,3]Thiadiazole-4-carboxylic acid (4-{3-[1-(4-bromo-phenyl)-ethyl]-thioureido}-phenyl)-amide |
| 648 | 413 | [1,2,3]Thiadiazole-4-carboxylic acid {4-[3-(4-phenyl-butyl)-thioureido]-phenyl}-amide |
| 649 | 397 | [1,2,3]Thiadiazole-4-carboxylic acid [4-(3-indan-1-yl-thioureido)-phenyl]-amide |
| 650 | 400 | [1,2,3]Thiadiazole-4-carboxylic acid {4-[3-(2-methoxy-benzyl)-thioureido]-phenyl}-amide |
| 651 | 415 | [1,2,3]Thiadiazole-4-carboxylic acid (4-{3-[2-(2-methoxy-phenyl)-ethyl]-thioureido}-phenyl)-amide |
| 652 | 415 | [1,2,3]Thiadiazole-4-carboxylic acid (4-{3-[2-(4-methoxy-phenyl)-ethyl]-thioureido}-phenyl)-amide |
| 653 | 506 | N-(4-{3-[2-(3-Dimethylamino-5-trifluoromethyl-phenyl)-ethyl]-thioureido}-phenyl)-2-fluoro-benzamide |
| 654 | 510 | [1,2,3]Thiadiazole-4-carboxylic acid (4-{3-[3-(3-dimethylamino-propyl)-5-trifluoromethyl-phenyl]-thioureido}-phenyl)-amide |
| 655 | 417 | [1,2,3]Thiadiazole-4-carboxylic acid {4-[3-(2-phenylsulfanyl-ethyl)-thioureido]-phenyl}-amide |
| 656 | 427 | 2-Fluoro-N-{4-[3-(2-phenylsulfanyl-ethyl)-thioureido]-phenyl}-benzamide |
| 657 | 399 | Furan-2-carboxylic acid {4-[3-(2-phenylsulfanyl-ethyl)-thioureido]-phenyl}-amide |

-continued

| EX. NO. | M + H | COMPOUND NAME |
|---|---|---|
| 658 | 381 | 2-Fluoro-N-[4-(3-pyridin-4-ylmethyl-thioureido)-phenyl]-benzamide |
| 659 | 353 | Furan-2-carboxylic acid [4-(3-pyridin-4-ylmethyl-thioureido)-phenyl]-amide |
| 660 | 371 | [1,2,3]Thiadiazole-4-carboxylic acid [4-(3-pyridin-4-ylmethyl-thioureido)-phenyl]-amide |
| 661 | 506 | 2-Fluoro-N-{4-[3-(3-iodo-benzyl)-thioureido]}-benzamide |
| 662 | 478 | Furan-2-carboxylic acid {4-[3-(3-iodo-benzyl)-thioureido]-phenyl}-amide |
| 663 | 496 | [1,2,3]Thiadiazole-4-carboxylic acid {4-[3-(3-iodo-benzyl)-thioureido]-phenyl}-amide |
| 664 | 479 | N-(4-}3-[2-(3,5-Dichloro-phenoxy)-ethyl]-thioureido}-phenyl)-2-fluoro-benzamide |
| 665 | 451 | Furan-2-carboxylic acid (4-{3-[2-(3,5-dichloro-phenoxy)-ethyl]-thioureido}-phenyl)-amide |
| 666 | 445 | N-(4-{3-[2-(3-Chloro-phenoxy)-ethyl]-thioureido}-phenyl)-2-fluoro-benzamide |
| 667 | 417 | Furan-2-carboxylic acid (4-{3-[2-(3-chloro-phenoxy)-ethyl]-thioureido}-phenyl)-amide |
| 668 | 435 | [1,2,3]Thiadiazole-4-carboxylic acid (4-{3-[2-(3-chloro-phenoxy)-ethyl]-thioureido}-phenyl)-amide |
| 669 | 466 | 2-Fluoro-N-{4-[3-(2-fluoro-5-trifluoromethyl-benzyl)-thioureido]-phenyl}-benzamide |
| 670 | 438 | Furan-2-carboxylic acid {4-[3-(2-fluoro-5-trifluoromethyl-benzyl)-thioureido]-phenyl}-amide |
| 671 | 456 | [1,2,3]Thiadiazole-4-carboxylic acid {4-[3-(2-fluoro-5-trifluoromethyl-benzyl)-thioureido]-phenyl}-amide |
| 672 | 416 | N-{4-[3-(3,4-Difluoro-benzyl)-thioureido]-phenyl}-2-fluoro-benzamide |
| 673 | 452 | N-(4-{3-[2-(4-Dimethylamino-3-methyl-phenyl)-ethyl]-thioureido}-phenyl)-2-fluoro-benzamide |
| 674 | 496 | [1,2,3]Thiadiazole-4-carboxylic acid (4-{3-[2-(3-dimethylamino-5-trifluoro-methyl-phenyl)-ethyl]-thioureido}-phenyl)-amide |
| 675 | 388 | Furan-2-carboxylic acid {4-[3-(3,4-difluoro-benzyl)-thioureido]-phenyl}-amide |
| 676 | 406 | [1,2,3]Thiadiazole-4-carboxylic acid {4-[3-(3,4-difluoro-benzyl)-thioureido]-phenyl}-amide |
| 677 | 433 | N-{4-[3-(3-Chloro-4-fluoro-benzyl)-thioureido]-phenyl}-2-fluoro-benzamide |
| 678 | 495 | [1,2,3]Thiadiazole-4-carboxylic acid (4-{3-[2-(3-bromo-phenylsulfanyl)-ethyl]-thioureido}-phenyl)-amide |
| 679 | 477 | Furan-2-carboxylic acid (4-{3-[2-(3-bromo-phenylsulfanyl)-ethyl]-thioureido}-phenyl)-amide |
| 680 | 505 | N-(4-{3-[2-(3-Bromo-phenylsulfanyl)-ethyl]-thioureido}-phenyl)-2-fluoro-benzamide |
| 681 | 493 | [1,2,3]Thiadiazole-4-carboxylic acid (4-{3-[2-(3-bromo-4-methoxy-phenyl)-ethyl]-thioureido}-phenyl)-amide |
| 682 | 493 | [1,2,3]Thiadiazole-4-carboxylic acid (4-{3-[2-(5-bromo-2-methoxy-phenyl)-ethyl]-thioureido}-phenyl)-amide |
| 683 | 419 | [1,2,3]Thiadiazole-4-carboxylic acid (4-{3-[2-(2-chloro-phenyl)-ethyl]-thioureido}-phenyl)-amide |
| 684 | 402 | [1,2,3]Thiadiazole-4-carboxylic acid (4-{3-[2-(2-fluoro-phenyl)-ethyl]-thioureido}-phenyl)-amide |
| 685 | 419 | [1,2,3]Thiadiazole-4-carboxylic acid (4-{3-[2-(4-chloro-phenyl)-ethyl]-thioureido}-phenyl)-amide |
| 686 | 475 | [1,2,3]Thiadiazole-4-carboxylic acid {4-[3-(3,3-diphenyl-propyl)-thioureido]-phenyl}-amide |
| 687 | 547 | 2-Fluoro-N-(4-{3-[4-(4-methyl-piperazin-1-yl)-3-trifluoromethyl-benzyl]-thioureido}-phenyl)-benzamide |
| 688 | 469 | [1,2,3]Thiadiazole-4-carboxylic acid (4-{3-[2-(3,5-dichloro-phenoxy)-ethyl]-thioureido}-phenyl)-amide |
| 689 | 423 | [1,2,3]Thiadiazole-4-carboxylic acid {4-[3-(3-chloro-4-fluoro-benzyl)-thioureido]-phenyl}-amide |
| 690 | 427 | [1,2,3]Thiadiazole-4-carboxylic acid {4-[3-(4-tert-butyl-benzyl)-thioreido]-phenyl}-amide |
| 691 | 399 | [1,2,3]Thiadiazole-4-carboxylic acid {4-[3-(3,5-dimethyl-benzyl)-thioureido]-phenyl}-amide |
| 692 | 442 | [1,2,3]Thiadiazole-4-carboxylic acid (4-{3-[2-(4-dimethylamino-3-methyl-phenyl)-ethy1]-thioureido}-phenyl)-amide |
| 693 | 479 | [1,2,3]Thiadiazole-4-carboxylic acid (4-{3-[2-(4-bromo-phenoxy)-ethyl]-thioureido}-phenyl)-amide |
| 694 | 526 | [1,2,3]Thiadiazole-4-carboxylic acid (4-{3-[2-(4-iodo-phenoxy)-ethyl]-thioureido}-phenyl)-amide |
| 695 | 489 | N-(4-{3-[2-(4-Bromo-phenoxy)-ethyl]-thioureido}-phenyl)-2-fluoro-benzamide |
| 696 | 536 | 2-Fluoro-N-(4-{3-[2-(4-iodo-phenoxy)-ethyl]-thioureido}-phenyl)-benzamide |
| 697 | 461 | Furan-2-carboxylic acid (4-{3-[2-(4-bromo-phenoxy)-ethyl]-thioureido}-phenyl)-amide |
| 698 | 508 | Furan-2-carboxylic acid (4-{3-[2-(4-iodo-phenoxy)-ethyl]-thioureido}-phenyl)-amide |
| 699 | 408 | Oxazole-4-carboxylic acid {4-[3-(3,4-dichloro-phenyl)-thioureido]-phenyl}-amide |
| 700 | 424 | Thiazole-4-carboxylic acid {4-[3-(3,5-dichloro-phenyl)-thioureido]-phenyl}-amide |
| 701 | 491 | Thiazole-4-carboxylic acid {4-[3-(3,5-bis-trifluoromethyl-phenyl)-thioureido]-phenyl}-amide |
| 702 | 408 | Oxazole-4-carboxylic acid {4-[3-(3,5-dichloro-phenyl)-thioureido]-phenyl}-amide |
| 703 | 469 | [1,2,3]Thiadiazole-4-carboxylic acid (4-{3-[2-(3,4-dichloro-phenoxy)-ethyl]-thioureido}-phenyl)-amide |
| 704 | 424 | Thiazole-4-carboxylic acid {4-[3-(3,4-dichloro-phenyl)-thioureido]-phenyl}-amide |
| 705 | 458 | Thiazole-4-carboxylic acid {4-[3-(4-chloro-3-trifluoromethyl-phenyl)-thioureido]-phenyl}-amide |
| 706 | 400 | [1,2,3]Thiadiazole-4-carboxylic acid {4-[3-(2-phenylamino-ethyl)-thioureido]-phenyl}-amide |
| 707 | 453 | [1,2,3]Thiadiazole-4-carboxylic acid (4-{3-[2-(2,4-dichloro-phenyl)-ethyl]-thioureido}-phenyl)-amide |
| 708 | 452 | [1,2,3]Thiadiazole-4-carboxylic acid (4-{3-[2-(3-trifluoromethyl-phenyl)-ethyl]-thioureido}-phenyl)-amide |
| 709 | 453 | [1,2,3]Thiadiazole-4-carboxylic acid (4-{3-[2-(2,6-dichloro-phenyl)-ethyl]-thioureido}-phenyl)-amide |
| 710 | 485 | [1,2,3]Thiadiazole-4-carboxylic acid (4-{3-[2-(3,4-dichloro-phenylsulfanyl)-ethyl]-thioureido}-phenyl)-amide |
| 711 | 503 | [1,2,3]Thiadiazole-4-carboxylic acid (4-{3-[2-(2-fluoro-5-trifluoromethylphenylsulfanyl)-ethyl]-thioureido}-phenyl)-amide |
| 712 | 668 | N-(4-{3-[3-Chloro-5-(3-{4-[([1,2,3]thiadiazole-4-carbonyl)-amino]-phenyl}-thioureido)-phenyl]-thioureido}-phenyl)-[1,2,3]thiadiazole-4-carboxamide |
| 713 | 413 | [1,2,3]Thiadiazole-4-carboxylic acid (4-{3-[2-(4-ethyl-phenyl)-ethyl]-thioureido}-phenyl)-amide |
| 714 | 442 | Oxazole-4-carboxylic acid {4-[3-(4-chloro-3-trifluoromethyl-phenyl)-thioureido]-phenyl}-amide |
| 715 | 475 | Oxazole-4-carboxylic acid {4-[3-(3,5-bis-trifluoromethyl-phenyl)-thioureido]-phenyl}-amide |
| 716 | 420 | [1,2,3]Thiadiazole-4-carboxylic acid (4-{3-[2-(3,4-difluoro-phenyl)-ethyl]-thioureido}-phenyl)-amide |
| 717 | 452 | [1,2,3]Thiadiazole-4-carboxylic acid (4-{3-[2-(4-trifluoromethyl-phenyl)-ethyl]-thioureido}-phenyl)-amide |
| 718 | 435 | Furan-2-carboxylic acid (4-{3-[2-(3,4-dichloro-phenyl)-ethyl]-thioureido}-phenyl)-amide |
| 719 | 463 | N-(4-{3-[2-(3,4-Dichloro-phenyl)-ethyl]-thioureido}-phenyl)-2-fluoro-benzamide |
| 720 | 420 | [1,2,3]Thiadiazole-4-carboxylic acid (4-{3-[2-(3,5-difluoro-phenyl)-ethyl]-thioureido}-phenyl)-amide |
| 721 | 412 | 2-Fluoro-N-(4-{3-[2-(2-fluoro-phenyl)-ethyl]-thioureido}-phenyl)-benzamide |
| 722 | 429 | [1,2,3]Thiadiazole-4-carboxylic acid (4-{3-[2-(4-nitro-phenyl)-ethyl]-thioureido}-phenyl)-amide |
| 723 | 399 | [1,2,3]Thiadiazole-4-carboxylic acid {4-[3-(1-methyl-2-phenyl-ethyl)-thioureido]-phenyl}-amide |
| 724 | 437 | N-{4-[3-(4-tert-Butyl-benzyl)-thioureido]-phenyl}-2-fluoro-benzamide |
| 725 | 409 | N-{4-[3-(3,5-Dimethyl-benzyl)-thioureido]-phenyl}-2-fluoro-benzamide |
| 726 | 400 | [1,2,3]Thiadiazole-4-carboxylic acid {4-[3-(2-hydroxy-1-methyl-ethyl)-thioureido]-phenyl}-amide |
| 727 | 409 | 2-Fluoro-N-{4-[3-(1-methyl-1-phenyl-ethyl)-thioureido]-phenyl}-benzamide |
| 728 | 399 | [1,2,3]Thiadiazole-4-carboxylic acid {4-[3-(1-methyl-1-phenyl-ethyl)-thioureido]-phenyl}-amide |
| 729 | 405 | [1,2,3]Thiadiazole-4-carboxylic acid {4-[3-(2-chloro-benzyl)-thioureido]-phenyl}-amide |
| 730 | 388 | [1,2,3]Thiadiazole-4-carboxylic acid {4-[3-(2-fluoro-benzyl)-thioureido]-phenyl}-amide |
| 731 | 438 | [1,2,3]Thiadiazole-4-carboxylic acid {4-[3-(3-trifluoromethyl-benzyl)-thioureido]-phenyl}-amide |
| 732 | 388 | [1,2,3]Thiadiazole-4-carboxylic acid {4-[3-(3-fluoro-benzyl)-thioureido]-phenyl}-amide |

-continued

| EX. NO. | M + H | COMPOUND NAME |
|---|---|---|
| 733 | 435 | [1,2,3]Thiadiazole-4-carboxylic acid (4-{3-[2-(2-chloro-phenoxy)-ethyl]-thioureido}-phenyl)-amide |
| 734 | 479 | [1,2,3]Thiadiazole-4-carboxylic acid (4-{3-[2-(3-bromo-phenoxy)-ethyl]-thioureido}-phenyl)-amide |
| 735 | 418 | [1,2,3]Thiadiazole-4-carboxylic acid (4-{3-[2-(2-fluoro-phenoxy)-ethyl]-thioureido}-phenyl)-amide |
| 736 | 418 | [1,2,3]Thiadiazole-4-carboxylic acid (4-{3-[2-(3-fluoro-phenoxy)-ethyl]-thioureido}-phenyl)-amide |
| 737 | 486 | [1,2,3]Thiadiazole-4-carboxylic acid (4-{3-[2-(2-fluoro-5-trifluoromethyl-phenoxy)-ethyl]-thioureido}-phenyl)-amide |
| 738 | 384 | Furan-2-carboxylic acid (4-{3-[2-(2-fluoro-phenyl)-ethyl]-thioureido}-phenyl)-amide |
| 739 | 435 | [1,2,,3]Thiadiazole-4-carboxylic acid {4-[3-(4-bromo-phenyl)-thioureido]-phenyl}-amide |
| 740 | 374 | [1,2,3]Thiadiazole-4-carboxylic acid {4-[3-(4-fluoro-phenyl)-thioureido]-phenyl}-amide |
| 741 | 388 | [1,2,3)Thiadiazole-4-carboxylic acid {4-[3-(4-fluoro-benzyl)-thioureido]-phenyl}-amide |
| 742 | 405 | [1,2,3]Thiadiazole-4-carboxylic acid {4-[3-(4-chloro-benzyl)-thioureido]-phenyl}-amide |
| 743 | 449 | [1,2,3]Thiadiazole-4-carboxylic acid {4-[3-(4-bromo-benzyl)-thioureido]-phenyl}-amide |
| 744 | 332 | N-(4-{3-[1-(4-Fluoro-phenyl)-ethyl]-thioureido}-phenyl)-acetamide |
| 745 | 438 | Thiazole-4-carboxylic acid {4-[3-(3,4-dichloro-benzyl)-thioureido]-phenyl}-amide |
| 746 | 455 | Thiazole-4-carboxylic acid {4-[3-(2-fluoro-5-trifluoromethyl-benzyl)-thioureido]-phenyl}-amide |
| 747 | 426 | Thiazole-4-carboxylic acid {4-[3-(4-tert-butyl-benzyl)-thioureido]-phenyl}-amide |
| 748 | 374 | [1,2,3]Thiadiazole-4-carboxylic acid {4-[3-(2-fluoro-phenyl)-thioureido]-phenyl}-amide |
| 749 | 374 | [1,2,3]Thiadiazole-4-carboxylic acid {4-[3-(3-fluoro-phenyl)-thioureido]-phenyl}-amide |
| 750 | 526 | [1,2,3]Thiadiazole-4-carboxylic acid (4-{3-[2-(3-iodo-phenoxy)-ethyl]-thioureido}-phenyl)-amide |
| 751 | 409 | N-(4-{3-[1-(4-fluoro-phenyl)-ethyl]-thioureido}-phenyl)-2-phenyl-acetamide |
| 752 | 425 | N-(4-{3-[1-(4-Fluoro-phenyl)-ethyl]-thioureido}-phenyl)-2-methoxy-benzamide |
| 753 | 425 | N-(4-{3-[1-(4-Fluoro-phenyl)-ethyl]-thioureido}-phenyl)-3-methoxy-benzamide |
| 754 | 425 | N-(4-{3-[1-(4-Fluoro-phenyl)-ethyl]-thioureido}-phenyl)-4-methoxy-benzamide |
| 755 | 429 | 2-Chloro-N-(4-{3-[1-(4-fluoro-phenyl)-ethyl]-thioureido}-phenyl)-benzamide |
| 756 | 429 | 4-Chloro-N-(4-{3-[1-(4-fluoro-phenyl)-ethyl]-thioureido}-phenyl)-benzamide |
| 757 | 453 | Acetic acid 4-(4-{3-[1-(4-fluoro-phenyl)-ethyl]-thioureido}-phenylcarbamoyl)-phenyl ester |
| 758 | 394 | N-(4-{3-[1-(4-Fluoro-phenyl)-ethyl]-thioureido}-phenyl)-benzamide |
| 759 | 395 | N-(4-{3-[1-(4-Fluoro-phenyl)-ethyl]-thioureido}-phenyl)-isonicotinamide |
| 760 | 410 | N-(4-{3-[1-(4-Fluoro-phenyl)-ethyl]-thioureido}-phenyl)-4-hydroxy-benzamide |
| 761 | 429 | 3-Chloro-N-(4-{3-[1-(4-fluoro-phenyl)-ethyl]-thioureido}-phenyl)-benzamide |
| 762 | 470 | [1,2,3]Thiadiazole-4-carboxylic acid (4-{3-[2-(3-fluoro-5-trifluoromethyl-phenyl)-ethyl]-thioureido}-phenyl)-amide |
| 763 | 520 | [1,2,3]Thiadiazole-4-carboxylic acid (4-{3-[2-(2,4-bis-trifluoromethyl-phenyl)-ethyl]-thioureido}-phenyl)-amide |
| 764 | 470 | [1,2,3]Thiadiazole-4-carboxylic acid (4-{3-[2-(4-fluoro-3-trifluoromethyl-phenyl)-ethyl]-thioureido}-phenyl)-amide |
| 765 | 438 | 4-Dimethylamino-N-(4-{3-[1-(4-fluoro-phenyl)-ethyl]-thioureido}-phenyl)-benzamide |
| 766 | 470 | [1,2,3]Thiadiazole-4-carboxylic acid (4-{3-[2-(2-fluoro-3-trifluoromethyl-phenyl)-ethyl]-thioureido}-phenyl)-amide |
| 767 | 470 | [1,2,3]Thiadiazole-4-carboxylic acid (4-{3-[2-(2-fluoro-5-trifluoromethyl-phenyl)-ethyl]-thioureido}-phenyl)-amide |
| 768 | 510 | [1,2,3]Thiadiazole-4-carboxylic acid (4-{3-[2-(3-iodo-phenyl)-ethyl]-thioureido}-phenyl)-amide |
| 769 | 470 | [1,2,3]Thiadiazole-4-carboxylic acid (4-{3-[2-(4-fluoro-2-trifluoromethyl-phenyl)-ethyl]-thioureido}-phenyl)-amide |
| 770 | 463 | [1,2,3]Thiadiazole-4-carboxylic acid (4-{3-[2-(3-bromo-phenyl)-ethyl]-thioureido}-phenyl)-amide |
| 771 | 427 | 2-Fluoro-N-(4-{3-[1-(4-fluoro-phenyl)-propyl]-thioureido}-phenyl)-benzamide |
| 772 | 475 | 2-Fluoro-N-(4-{3-[(4-fluoro-phenyl)-phenyl-methyl]-thioureido}-phenyl)-benzamide |
| 773 | 455 | 2-Fluoro-N-(4-{3-[1-(4-fluoro-phenyl)-pentyl]-thioureido}-phenyl)-benzamide |
| 774 | 489 | 2-Fluoro-N-(4-{3-[1-(4-fluoro-phenyl)-2-phenyl-ethyl]-thioureido}-phenyl)benzamide |
| 775 | 409 | 2-Fluoro-N-{4-[3-(1-o-tolyl-ethyl)-thioureido]-phenyl}-benzamide |
| 776 | 409 | 2-Fluoro-N-{4-[3-(1-m-tolyl-ethyl)-thioureido]-phenyl}-benzamide |
| 777 | 425 | 2-Fluoro-N-(4-{3-[1-(4-methoxy-phenyl)-ethyl]-thioureido}-phenyl)-benzamide |
| 778 | 412 | 2-Fluoro-N-(4-{3-[1-(2-fluoro-phenyl)-ethyl]-thioureido}-phenyl)-benzamide |
| 779 | 429 | N-(4-{3-[1-(3-Chloro-phenyl)-ethyl]-thioureido}-phenyl)-2-fluoro-benzamide |
| 780 | 473 | N-(4-{3-[1-(3-Bromo-phenyl)-ethyl]-thioureido}-phenyl)-2-fluoro-benzamide |
| 781 | 429 | N-(4-{3-[1-(4-Chloro-phenyl)-ethyl]-thioureido}-phenyl)-2-fluoro-benzamide |
| 782 | 409 | 2-Fluoro-N-{4-[3-(1-p-tolyl-ethyl)-thioureido]-phenyl}-benzamide |
| 783 | 473 | N-(4-{3-[1-(2-Bromo-phenyl)-ethyl]-thioureido}-phenyl)-2-fluoro-benzamide |
| 784 | 429 | N-(4-{3-[1-(2-Chloro-phenyl)-ethyl]-thioureido}-phenyl)-2-fluoro-benzamide |
| 785 | 462 | 2-Fluoro-N-(4-{3-[1-(2-trifluoromethyl-phenyl)-ethyl]-thioureido}-phenyl)-benzamide |
| 786 | 462 | 2-Fluoro-N-(4-{3-[1-(3-trifluoromethyl-phenyl)-ethyl]-thioureido}-phenyl)-benzamide |
| 787 | 462 | 2-Fluoro-N-(4-{3-[1-(4-trifluoromethyl-phenyl)-ethyl]-thioureido}-phenyl)-benzamide |
| 788 | 425 | 2-Fluoro-N-(4-{3-[1-(2-methoxy-phenyl)-ethyl]-thioureido}-phenyl)-benzamide |
| 789 | 425 | 2-Fluoro-N-(4-{3-[1-(3-methoxy-phenyl)-ethyl]-thioureido}-phenyl)-benzamide |
| 790 | 441 | 2-Fluoro-N-(4-{3-[1-(4-fluoro-phenyl)-2-methyl-propyl]-thioureido}-phenyl)-benzamide |
| 791 | 419 | N-(4-{3-[1-(3-Cyano-phenyl)-ethyl]-thioureido}-phenyl)-2-fluoro-benzamide |
| 792 | 419 | N-(4-{3-[1-(4-Cyano-phenyl)-ethyl]-thioureido}-phenyl)-2-fluoro-benzamide |
| 793 | 438 | N-(4-{3-[1-(4-Dimethylamino-phenyl)-ethyl]-thioureido}-phenyl)-2-fluoro-benzamide |
| 794 | 438 | N-(4-{3-[1-(3-Dimethylamino-phenyl)-ethyl]-thioureido}-phenyl)-2-fluoro-benzamide |
| 795 | 473 | 2-Bromo-N-(4-{3-[1-(4-fluoro-phenyl)-ethyl]-thioureido}-phenyl)-benzamide |
| 796 | 446 | Quinoline-2-carboxylic acid (4-{3-[1-(4-fluoro-phenyl)-ethyl]-thioureido}-phenyl)-amide |
| 797 | 410 | 2-Fluoro-N-{4-[3-(2-hydroxy-1-phenyl-ethyl)-thioureido]-phenyl}-benzamide |
| 798 | 332 | 2-Fluoro-N-[4-(3-isopropyl-thioureido)-phenyl]-benzamide |
| 799 | 445 | 2-Fluoro-N-{4-[3-(1-naphthalen-2-yl-ethyl)-thioureido]-phenyl}-benzamide |
| 800 | 412 | 3-Fluoro-N-(4-{3-[1-(4-fluoro-phenyl)-ethyl]-thioureido}-phenyl)-benzamide |
| 801 | 412 | 4-Fluoro-N-(4-{3-[1-(4-fluoro-phenyl)-ethyl]-thioureido}-phenyl)-benzamide |
| 802 | 384 | 2-Fluoro-N-{4-[3-(1-furan-2-yl-ethyl)-thioureido]-phenyl}-benzamide |
| 803 | 395 | 2-Fluoro-N-{4-[3-(1-pyridin-4-yl-ethyl)-thioureido]-phenyl}-benzamide |
| 804 | 397 | 2-Fluoro-N-(4-{3-[1-(1-methyl-1H-pyrrol-2-yl)-ethyl]-thioureido}-phenyl)-benzamide |
| 805 | 401 | 2-Fluoro-N-{4-[3-(1-thiophen-3-yl-ethyl)-thioureido]-phenyl}-benzamide |
| 806 | 445 | N-{4-[3-(3-Chloro-4-ethoxy-phenyl)-thioureido]-phenyl}-2-fluoro-benzamide |
| 807 | 459 | N-{4-[3-(3-Chloro-4-propoxy-phenyl)-thioureido]-phenyl}-2-fluoro-benzamide |
| 808 | 459 | N-{4-(3-(3-Chloro-4-isopropoxy-phenyl)-thioureido-phenyl}-2-fluoro-benzamide |

-continued

| EX. NO. | M + H | COMPOUND NAME |
|---|---|---|
| 809 | 473 | N-{4-[3-(4-Butoxy-3-chloro-phenyl)-thioureido]-phenyl}-2-fluoro-benzamide |
| 810 | 522 | 2-Fluoro-N-{4-[3-(3-iodo-4-methoxy-phenyl)-thioureido]-phenyl}-benzamide |
| 811 | 475 | N-{4-[3-(3-Bromo-4-methoxy-phenyl)-thioureido]-phenyl}-2-fluoro-benzamide |
| 812 | 520 | N-(4-{3-[1-(4-Fluoro-phenyl)-ethyl]-thioureido}-phenyl)-2-iodo-benzamide |
| 813 | 346 | N-(4-{3-[1-(4-Fluoro-phenyl)-ethyl]-thioureido}-phenyl)-propionamide |
| 814 | 286 | N-[4-(3-Phenyl-thioureido)-phenyl]-acetamide |

EXAMPLE 815

(Method 32)

2,3]Thiadiazole-4-carboxylic Acid {4-[3-(2,5-dichloro-phenyl-thioureido]-phenyl}-amide To a solution of 2,5-dichloroaniline (0.16 g) in tetrahydrofuran (20 mL) is added freshly prepared 1,1'-thiocarbonyldiimidazole (0.20 g) and the mixture is stirred for approximately 30 minutes at room temperature. [1,2,3]-Thiadiazole-4-carboxylic acid (4-amino-phenyl) amide (0.22 g) is added to the reaction flask and the mixture is stirred for approximately 6 hours. The solvent is then removed by evaporation under reduced pressure and warm acetonitrile (3 mL) is added. After 15 hours the mixture is filtered and the collected precipitate is washed with acetonitrile then diethyl ether, and air dried to provide the desired product as a white powder.

Used the above procedure and appropriate starting materials the following compounds were prepared:

| EX. NO. | M + H | COMPOUND NAME |
|---|---|---|
| 816 | 321 | N-{4-[3-(3-Chloro-phenyl)-thioureido]-phenyl}-acetamide |
| 817 | 413 | N-{4-[3-(3-Chloro-4-methoxy-phenyl)-thioureido]-phenyl}-benzamide |
| 818 | 443 | N-{4-[3-(3-Chloro-4-methoxy-phenyl)-thioureido]-phenyl}-2-methoxy-benzamide |
| 819 | 443 | N-{4-[3-(3-Chloro-4-methoxy-phenyl)-thioureido]-phenyl}-3-methoxy-benzamide |
| 820 | 443 | N-{4-[3-(3-Chloro-4-methoxy-phenyl)-thioureido]-phenyl}-4-methoxy-benzamide |
| 821 | 431 | N-{4-[3-(3-Chloro-4-methoxy-phenyl)-thioureido]-phenyl}-4-methoxy-benzamide |
| 822 | 431 | N-{4-[3-(3-Chloro-4-methoxy-phenyl)-thioureido]-phenyl}-3-fluoro-benzamide |
| 823 | 431 | N-{4-[3-(3-Chloro-4-methoxy-phenyl)-thioureido]-phenyl}-4-fluoro-benzamide |
| 824 | 437 | Furan-2-carboxylic acid {4-[3-(3,5-dichloro-4-methoxy-phenyl)-thioureido]-phenyl}-amide |
| 825 | 511 | {4-[3-(5-Bromo-2,4-dimethoxy-phenyl)-thioureido]-phenyl}-carbamic acid hexyl ester |
| 826 | 481 | Hexanoic acid {4-[3-(5-bromo-2,4-dimethoxy-phenyl)-thioureido]-phenyl}-amide |
| 827 | 505 | N-{4-[3-(5-Bromo-2,4-dimethoxy-phenyl)-thioureido]-phenyl}-2-fluoro-benzamide |
| 828 | 477 | Furan-2-carboxylic acid {4-[3-(5-bromo-2,4-dimethoxy-phenyl)-thioureido]-phenyl}-amide |
| 829 | 501 | N-{4-[3-(5-Bromo-2,4-dimethoxy-phenyl)-thioureido]-phenyl}-2-methyl-benzamide |
| 830 | 517 | N-{4-[3-(5-Bromo-2,4-dimethoxy-phenyl)-thioureido]-phenyl}-4-methoxy-benzamide |
| 831 | 395 | N-{4-[3-(5-Chloro-2-ethoxy-4-methoxy-phenyl)-thioureido]-phenyl}-acetamide |
| 832 | 395 | N-{4-[3-(5-Chloro-4-ethoxy-2-methoxy-phenyl)-thioureido]-phenyl}-acetamide |
| 833 | 423 | N-{4-[3-(2-Butoxy-5-chloro-4-methoxy-phenyl)-thioureido]-phenyl}-acetamide |
| 834 | 423 | N-{4-[3-(4-Butoxy-5-chloro-2-methoxy-phenyl)-thioureido]-phenyl}-acetamide |
| 835 | 457 | N-{4-[3-(2-Benzyloxy-5-chloro-4-methoxy-phenyl)-thioureido]-phenyl}-acetamide |
| 836 | 457 | N-{4-[3-(4-Benzyloxy-5-chloro-2-methoxy-phenyl)-thioureido]-phenyl}-acetamide |
| 837 | 421 | [1,2,3]Thiadiazole-4-carboxylic acid {4-[3-(3-chloro-4-methoxy-phenyl)-thioureido]-phenyl}-amide |
| 838 | 424 | 2-{4-[3-(4-Acetylamino-phenyl)-thioureido]-2-chloro-5-methoxy-phenoxy}-acetamide |
| 839 | 367 | N-{4-[3-(5-Chloro-2-hydroxy-4-methoxy-phenyl)-thioureido]-phenyl}-acetamide |
| 840 | 367 | N-{4-[3-(3-Chloro-4-methylsulfanyl-phenyl)-thioureido]-phenyl}-acetamide |
| 841 | 447 | N-[4-(3-{3-Chloro-4-[methyl-(1-methyl-piperidin-4-yl)-amino]-phenyl}-thioureido)-phenyl]-acetamide |
| 842 | 426 | N-(4-{3-[3-Chloro-4-(methyl-phenyl-amino)-phenyl]-thioureido}-phenyl)-acetamide |
| 843 | 509 | N-[4-(3-{4-[(1-Benzyl-pyrrolidin-3-yl)-methyl-amino]-3-chloro-phenyl}-thioureido)-phenyl]-acetamide |
| 844 | 418 | N-(4-{3-[3-Chloro-4-(cyclopentyl-methyl-amino)-phenyl]-thioureido}-phenyl)-acetamide |
| 845 | 433 | N-[4-(3-{3-Chloro-4-[methyl-(1-methyl-pyrrolidin-3-yl)-amino]-phenyl}-thioureido)-phenyl]-acetamide |
| 846 | 419 | Furan-2-carboxylic acid {4-[3-(3-chloro-4-methylsulfanyl-phenyl)-thioureido]-phenyl}-amide |
| 847 | 447 | N-{4-[3-(3-Chloro-4-methylsulfanyl-phenyl)-thioureido]-phenyl}-2-fluoro-benzamide |
| 848 | 465 | N-{4-[3-(3-Chloro-4-methylsulfanyl-phenyl)-thioureido]-phenyl}-2,6-difluoro-benzamide |
| 849 | 445 | N-{4-[3-(5-Chloro-2-methoxy-4-methyl-phenyl)-thioureido]-phenyl}-2-fluoro-benzamide |
| 850 | 441 | N-{4-[3-(5-Chloro-2-methoxy-4-methyl-phenyl)-thioureido]-phenyl}-2-methyl-benzamide |
| 851 | 434 | [1,2,3]Thiadiazole-4-carboxylic acid {4-[3-(3-chloro-4-dimethylamino-phenyl)-thioureido]-phenyl}-amide |
| 852 | 444 | N-{4-[3-(3-Chloro-4-dimethylamino-phenyl)-thioureido]-phenyl}-2-fluoro-benzamide |
| 853 | 517 | [1,2,3]Thiadiazole-4-carboxylic acid [4-(3-{3-chloro-4-[methyl-(1-methyl-piperidin-4-yl)-amino]-phenyl}-thioureido)-phenyl]-amide |
| 854 | 579 | [1,2,3]Thiadiazole-4-carboxylic acid [4-(3-{4-[(1-benzyl-pyrrolidin-3-yl)-methyl-amino]-3-chloro-phenyl}-thioureido)-phenyl]-amide |
| 855 | 527 | N-[4-(3-{3-Chloro-4-[methyl-(1-methyl-piperidin-4-yl)-amino]-phenyl}-thioureido)-phenyl]-2-fluoro-benzamide |
| 856 | 435 | [1,2,3]Thiadiazole-4-carboxylic acid {4-[3-(5-chloro-2-methoxy-4-methyl-phenyl)-thioureido]-phenyl}-amide |
| 857 | 589 | N-[4-(3-{4-[(1-Benzyl-pyrrolidin-3-yl)-methyl-amino]-3-chloro-phenyl}-thioureido)-phenyl]-2-fluoro-benzamide |
| 858 | 501 | Furan-2-carboxylic acid {4-[3-(5-chloro-2,4-dimethoxy-phenyl)-thioureido]-3-trifluoromethyl-phenyl}-amide |
| 859 | 366 | 2-Fluoro-N-[4-(3-phenyl-thioureido)-phenyl]-benzamide |
| 860 | 338 | Furan-2-carboxylic acid [4-(3-phenyl-thioureido)-phenyl]-amide |
| 861 | 356 | [1,2,3]Thiadiazole-4-carboxylic acid [4-(3-phenyl-thioureido)-phenyl]-amide |
| 862 | 365 | N-(4-{3-[3-Chloro-4-(1-hydroxy-ethyl)-phenyl]-thioureido}-phenyl)-acetamide |

-continued

| EX. NO. | M + H | COMPOUND NAME |
|---|---|---|
| 863 | 435 | [1,2,3]Thiadiazole-4-carboxylic acid (4-{3-[3-chloro-4-(1-hydroxy-ethyl)-phenyl]-thioureido}-phenyl)-amide |
| 864 | 365 | N-(4-{3-[3-Chloro-4-(2-hydroxy-ethyl)-phenyl]-thioureido}-phenyl)-acetamide |
| 865 | 445 | N-(4-{3-[3-Chloro-4-(1-hydroxy-ethyl)-phenyl]-thioureido}-phenyl)-2-fluoro-benzamide |
| 866 | 417 | Furan-2-carboxylic acid (4-{3-[3-chloro-4-(1-hydroxy-ethyl)-phenyl]-thioureido}-phenyl)-amide |
| 867 | 371 | [1,2,3]Thiadiazole-4-carboxylic acid {4-[3-(3-amino-phenyl)-thioureido]-phenyl}-amide |
| 868 | 501 | Furan-2-carboxylic acid {4-[3-(3-bromo-4-trifluoromethoxy-phenyl)-thioureido]-phenyl}-amide |
| 869 | 423 | N-{4-[3-(3-tert-Butyl-phenyl)-thioureido]-phenyl}-2-fluoro-benzamide |
| 870 | 440 | [1,2,3]Thiadiazole-4-carboxylic acid {4-[3-(4-chloro-3,5-dichloro-phenyl)-thioureido]-phenyl}-amide |
| 974 | 485 | N-{4-[3-(1-Benzofuran-2-yl-ethyl)-thioureido]-phenyl}-2-trifluoromethyl-benzamide |
| 975 | 412 | N-(4-Fluoro-phenyl)4-{3-[1-(4-fluoro-phenyl)-ethyl]-thioureido}-benzamide |
| 976 | 446 | Isoquinoline-1-carboxylic acid (4-{3-[1-(4-fluoro-phenyl)-ethyl]-thioureido}-phenyl)-amide |
| 977 | 468 | Isoquinoline-1-carboxylic acid {4-[3-(1-benzofuran-2-yl-ethyl)-thioureido-phenyl]-amide |
| 978 | 506 | Isoquinoline-1-carboxylic acid (4-{3-[1-(4-bromo-phenyl)-ethyl]-thioureido}-phenyl)-amide |
| 979 | 453 | Isoquinoline-1-carboxylic acid (4-{3-[1-(4-cyano-phenyl)-ethyl]-thioureido}-phenyl)-amide |
| 980 | 435 | Benzofuran-2-carboxylic acid (4-{3-[1-(4-fluoro-phenyl)-ethyl]-thioureido}-phenyl)-amide |
| 981 | 457 | Benzofuran-2-carboxylic acid {4-[3-(1-benzofuran-2-yl-ethyl)-thioureido]-phenyl}-amide |
| 982 | 495 | Benzofuran-2-carboxylic acid (4-{3-[1-(4-bromo-phenyl)-ethyl]-thioureido}-phenyl)-amide |
| 983 | 442 | Benzofuran-2-carboxylic acid (4-{3-[1-(4-cyano-phenyl)-ethyl]-thioureido}-phenyl)-amide |
| 984 | 446 | Isoquinoline-3-carboxylic acid (4-{3-[1-(4-fluoro-phenyl)-ethyl]-thioureido}-phenyl)-amide |
| 985 | 468 | Isoquinoline-3-carboxylic acid {4-[3-(1-benzofuran-2-yl-ethyl)-thioureido]-phenyl}-amide |
| 986 | 453 | Isoquinoline-3-carboxylic acid (4-{3-[1-(4-cyano-phenyl)-ethyl]-thioureido}-phenyl)-amide |
| 987 | 506 | Isoquinoline-3-carboxylic acid (4-{3-[1-(4-bromo-phenyl)-ethyl]-thioureido}-phenyl)-amide |
| 988 | 446 | Quinoline-3-carboxylic acid (4-{3-[1-(4-fluoro-phenyl)-ethyl]-thioureido}-phenyl)-amide |
| 989 | 446 | Quinoline-4-carboxylic acid (4-{3-[1-(4-fluoro-phenyl)-ethyl]-thioureido}-phenyl)-amide |
| 990 | 446 | Quinoline-6-carboxylic acid (4-{3-[1-(4-fluoro-phenyl)-ethyl]-thioureido}-phenyl)-amide |
| 991 | 446 | Quinoline-8-carboxylic acid (4-{3-[1-(4-fluoro-phenyl)-ethyl]-thioureido}-phenyl)-amide |
| 992 | 462 | N-(4-{3-[1-(4-Fluoro-phenyl)-ethyl]-thioureido}-phenyl)-2-trifluoromethyl-benzamide |
| 993 | 419 | 2-Cyano-N-(4-{3-[1-(4-fluoro-phenyl)-ethyl]-thioureido}-phenyl)-benzamide |
| 994 | 473 | N-{4-[3-(3-Chloro-4-isobutoxy-phenyl)-thioureido]-phenyl}-2-fluoro-benzamide |
| 995 | 414 | 2-Fluoro-N-{4-[3-(3-fluoro-4-methoxy-phenyl)-thioureido]-phenyl}-benzamide |
| 996 | 475 | N-(4-{3-[3-Chloro-4-(2-methoxy-ethoxy)-phenyl]-thioureido}-phenyl)-2-fluoro-benzamide |
| 997 | 398 | 2-Fluoro-N-{4-[3-(3-fluoro-4-methyl-phenyl)-thioureido]-phenyl}-benzamide |
| 998 | 464 | 2-Fluoro-N-{4-[3-(4-methoxy-3-trifluoromethyl-phenyl)-thioureido]-phenyl}-benzamide |
| 999 | 449 | N-{4-[3-(2-Amino-5-trifluoromethyl-phenyl)-thioureido]-phenyl}-2-fluoro-benzamide |
| 1000 | 459 | N-(4-{3-[1-(3-Chloro-4-methoxy-phenyl)-ethyl]-thioureido}-phenyl)-2-fluoro-benzamide |
| 1001 | 417 | N-{4-[3-(5-Chloro-2-hydroxy-phenyl)-thioureido]-phenyl}-2-fluoro-benzamide |
| 1002 | 435 | N-{4-[3-(1-Benzofuran-2-yl-ethyl)-thioureido]-phenyl}-2-fluoro-benzamide |
| 1003 | 448 | 2-Fluoro-N-{4-[3-(4-methyl-3-trifluoromethyl-phenyl)-thioureido]-phenyl}-benzamide |
| 1004 | 473 | (S)-N-(4-{3-[1-(4-Bromo-phenyl)-ethyl]-thioureido}-phenyl)-2-fluoro-benzamide |
| 1005 | 473 | N-(4-{3-[(1R)-1-(4-Bromo-phenyl)-ethyl]-thioureido}-phenyl)-2-fluoro-benzamide |
| 1006 | 494 | 2-Fluoro-N-(4-{3-[2-methoxy-4-(2,2,2-trifluoro-ethoxy)-phenyl]-thioureido}-phenyl)-benzamide |
| 1007 | 399 | N-{4-[3-(2-Amino-5-fluoro-phenyl)-thioureido]-phenyl}-2-fluoro-benzamide |
| 1008 | 502 | N-(4-{3-[1-(4-Dimethylsulfamoyl-phenyl)-ethyl]-thioureido}-phenyl)-2-fluoro-benzamide |
| 1009 | 542 | 2-Fluoro-N-[4-(3-{1-[4-(piperidine-1-sulfonyl)-phenyl]-ethyl}-thioureido)-phenyl]-benzamide |
| 1010 | 562 | N-(4-{3-[2,4-Bis-(2,2,2-trifluoro-ethoxy)-phenyl]-thioureido}-phenyl)-2-fluoro-benzamide |
| 1011 | 409 | 2-Fluoro-N-{4-[3-((1S)-1-p-tolyl-ethyl)-thioureido]-phenyl}-benzamide |
| 1012 | 409 | 2-Fluoro-N-{4-[3-((1R)-1-p-tolyl-ethyl)-thioureido]-phenyl}-benzamide |
| 1013 | 394 | 2-Fluoro-N-{4-[3-((1S)-1-phenyl-ethyl)-thioureido]-phenyl}-benzamide |
| 1014 | 429 | N-(4-{3-[(1R)-1-(4-Chloro-phenyl)-ethyl]-thioureido}-phenyl)-2-fluoro-benzamide |
| 1015 | 429 | N-(4-{3-[(1S)-1-(4-Chloro-phenyl)-ethyl]-thioureido}-phenyl)-2-fluoro-benzamide |
| 1016 | 394 | 2-Fluoro-N-{4-[3-((1R)-1-phenyl-ethyl)-thioureido]-phenyl}-benzamide |
| 1017 | 432 | N-(4-{3-[1-(4-Cyano-phenyl)-ethyl]-thioureido}-phenyl)-2-methoxy-benzamide |
| 1018 | 447 | N-{4-[3-(1-Benzofuran-2-yl-ethyl)-thioureido]-phenyl}-2-methoxy-benzamide |
| 1019 | 485 | N-(4-{3-[1-(4-Bromo-phenyl)-ethyl]-thioureido}-phenyl)-2-methoxy-benzamide |
| 1020 | 419 | 3-Cyano-N-(4-{3-[1-(4-fluoro-phenyl)-ethyl]-thioureido}-phenyl)-benzamide |
| 1021 | 462 | N-(4-{3-[1-(4-fluoro-phenyl)-ethyl]-thioureido}-phenyl)-4-trifluoromethyl-benzamide |
| 1022 | 419 | 4-Cyano-N-(4-{3-[1-(4-fluoro-phenyl)-ethyl]-thioureido}-phenyl)-benzamide |
| 1023 | 469 | 2-Fluoro-N-(4-{3-[1-(4-fluoro-phenyl)-ethyl]-thioureido}-2,3,5,6-tetramethyl-phenyl)-benzamide |
| 1024 | 480 | N-(4-{3-[1-(4-Cyano-phenyl)-ethyl]-thioureido}-2,5-dimethoxy-phenyl)-2-fluoro-benzamide |
| 1025 | 473 | 2-Fluoro-N-(4-{3-[1-(4-fluoro-phenyl)-ethyl]-thioureido}-2,5-dimethoxy-phenyl)-benzamide |
| 1026 | 530 | N-{3,5-Dichloro-4-[3-(5-chloro-2,4-dimethoxy-phenyl)-thioureido]-phenyl}-2-fluoro-benzamide |
| 1027 | 447 | N-(3-Chloro-4-{3-[1-(4-fluoro-phenyl)-ethyl]-thioureido}-phenyl)-2-fluoro-benzamide |
| 1028 | 480 | 2,3,4,5-Tetrafluoro-N-(4-{3-[1-(4-fluoro-phenyl)-ethyl]-thioureido}-3-methyl-phenyl)-benzamide |
| 1029 | 462 | 2,4,5-Trifluoro-N-(4-{3-[1-(4-fluoro-phenyl)-ethyl]-thioureido}-3-methyl-phenyl)-benzamide |
| 1030 | 427 | 2-Fluoro-N-(4-{3-[1-(4-fluoro-phenyl)-ethyl]-thioureido}-3-methyl-phenyl)-benzamide |
| 1031 | 457 | 2-Fluoro-N-(4-{3-[1-(4-fluoro-phenyl)-ethyl]-thioureido}-2-methoxy-5-methyl-phenyl)-benzamide |
| 1032 | 443 | 2-Fluoro-N-(4-{3-[1-(4-fluoro-phenyl)-ethyl]-thioureido}-3-methoxy-phenyl)-benzamide |
| 1033 | 570 | N-(2,6-Dibromo-4-{3-[1-(4-fluoro-phenyl)-ethyl]-thioureido}-phenyl)-2-fluoro-benzamide |
| 1034 | 480 | 2-Fluoro-N-(4-{3-[1-(4-fluoro-phenyl)-ethyl]-thioureido}-2-trifluoromethyl-phenyl)-benzamide |
| 1035 | 541 | N-(4-{3-[1-(4-Bromo-phenyl)-ethyl]-thioureido}-2-trifluoromethyl-phenyl)-2-fluoro-benzamide |
| 1036 | 487 | N-(4-{3-[1-(4-Cyano-phenyl)-ethyl]-thioureido}-2-trifluoromethyl-phenyl)-2-fluoro-benzamide |
| 1037 | 503 | N-{4-[3-(1-Benzofuran-2-yl-ethyl)-thioureido]-2-trifluoromethyl-phenyl}-2-fluoro-benzamide |
| 1038 | 447 | N-(2-Chloro-4-{3-[1-(4-fluoro-phenyl)-ethyl]-thioureido}-phenyl)-2-fluoro-benzamide |
| 1039 | 454 | N-(2-Chloro-4-{3-[1-(4-cyano-phenyl)-ethyl]-thioureido}-phenyl)-2-fluoro-benzamide |
| 1040 | 437 | N-(2-Cyano-4-{3-[1-(4-fluoro-phenyl)-ethyl]-thioureido}-phenyl)-2-fluoro-benzamide |
| 1041 | 498 | N-(4-{3-[1-(4-Bromo-phenyl)-ethyl]-thioureido}-2-cyano-phenyl)-2-fluoro-benzamide |

-continued

| EX. NO. | M + H | COMPOUND NAME |
|---|---|---|
| 1042 | 445 | N-(2-Cyano-4-{3-[1-(4-cyano-phenyl)-ethyl]-thioureido}-phenyl)-2-fluoro-benzamide |
| 1043 | 460 | N-{4-[3-(1-Benzofuran-2-yl-ethyl)-thioureido]-2-cyano-phenyl}-2-fluoro-benzamide |
| 1044 | 517 | N-(2-Benzoyl-4-{3-[1-(4-fluoro-phenyl)-ethyl]-thioureido}-phenyl)-2-fluoro-benzamide |
| 1045 | 427 | 2-Fluoro-N-(4-{3-[1-(4-fluoro-phenyl)-ethyl]-thioureido}-2-methyl-phenyl)-benzamide |
| 1046 | 487 | N-(4-{3-[1-(4-Bromo-phenyl)-ethyl]-thioureido}-2-methyl-phenyl)-2-fluoro-benzamide |
| 1047 | 434 | N-(4-{3-[1-(4-Cyano-phenyl)-ethyl]-thioureido}-2-methyl-phenyl)-2-fluoro-benzamide |
| 1048 | 449 | N-{4-[3-(1-Benzofuran-2-yl-ethyl)-thioureido]-2-methyl-phenyl}-2-fluoro-benzamide |
| 1049 | 456 | N-(2-Dimethylamino-4-{3-[1-(4-fluoro-phenyl)-ethyl]-thioureido}-phenyl)-2-fluoro-benzamide |
| 1050 | 526 | N-(2-Benzyloxy-4-{3-[1-(4-cyano-phenyl)-ethyl]-thioureido}-phenyl)-2-fluoro-benzamide |
| 1051 | 519 | N-(2-Benzyloxy-4-{3-[1-(4-fluoro-phenyl)-ethyl]-thioureido}-phenyl)-2-fluoro-benzamide |
| 1052 | 603 | N-[4-{3-[1-(4-Bromo-phenyl)-ethyl]-thioureido}-2-(2-morpholin-4-yl-ethoxy)-phenyl]-2-fluoro-benzamide |
| 1053 | 603 | N-[4-{3-[1-(4-Bromo-phenyl)-ethyl]-thioureido}-2-(2-morpholin-4-yl-ethoxy)-phenyl]-2-fluoro-benzamide |
| 1054 | 542 | 2-Fluoro-N-[4-{3-[1-(4-fluoro-phenyl)-ethyl]-thioureido}-2-(2-morpholin-4-yl-ethoxy)-phenyl]-benzamide |
| 1055 | 485 | N-(2-Butoxy-4-{3-[1-(4-fluoro-phenyl)-ethyl]-thioureido}-phenyl)-2-fluoro-benzamide |
| 1056 | 492 | N-(2-Butoxy-4-{3-[1-(4-cyano-phenyl)-ethyl]-thioureido}-phenyl)-2-fluoro-benzamide |
| 1057 | 589 | N-[4-{3-[1-(4-Bromo-phenyl)-ethyl]-thioureido}-2-(2-diethylamino-ethoxy)-phenyl]-2-fluoro-benzamide |
| 1058 | 528 | N-(2-(2-Diethylamino-ethoxy)-4-{3-[1-(4-fluoro-phenyl)-ethyl]-thioureido}-phenyl)-2-fluoro-benzamide |
| 1059 | 589 | N-[4-{3-[1-(4-Bromo-phenyl)-ethyl]-thioureido}-2-(2-diethylamino-ethoxy)-phenyl]-2-fluoro-benzamide |
| 1060 | 457 | N-(2-Ethoxy-4-{3-[1-(4-fluoro-phenyl)-ethyl]-thioureido}-phenyl)-2-fluoro-benzamide |
| 1061 | 464 | N-(4-{3-[1-(4-Cyano-phenyl)-ethyl]-thioureido}-2-ethoxy-phenyl)-2-fluoro-benzamide |
| 1062 | 468 | 2-Fluoro-N-[4-{3-[1-(4-fluoro-phenyl)-ethyl]-thioureido}-2-(2-nitrilo-ethoxy)-phenyl]-benzamide |
| 1063 | 475 | N-[4-{3-[1-(4-Cyano-phenyl)-ethyl]-thioureido}-2-(2-nitrilo-ethoxy)-phenyl]-2-fluoro-benzamide |
| 1064 | 443 | 2-Fluoro-N-(4-{3-[1-(4-fluoro-phenyl)-ethyl]-thioureido}-2-methoxy-phenyl)-benzamide |
| 1065 | 489 | 2-Fluoro-N-(5-{3-[1-(4-fluoro-phenyl)-ethyl]-thioureido}-biphenyl-2-yl)-benzamide |
| 1066 | 514 | Isoquinoline-1-carboxylic acid (4-{3-[1-(4-fluoro-phenyl)-ethyl]-thioureido}-2-trifluoromethyl-phenyl)-amide |
| 1067 | 503 | Benzofuran-2-carboxylic acid (4-{3-[1-(4-fluoro-phenyl)-ethyl]-thioureido}-2-trifluoromethyl-phenyl)-amide |
| 1068 | 514 | Isoquinoline-3-carboxylic acid (4-{3-[1-(4-fluoro-phenyl)-ethyl]-thioureido}-2-trifluoromethyl-phenyl)-amide |
| 1069 | 471 | Isoquinoline-1-carboxylic acid (2-cyano-4-{3-[1-(4-fluoro-phenyl)-ethyl]-thioureido}-phenyl)-amide |
| 1070 | 460 | Benzofuran-2-carboxylic acid (2-cyano-4-{3-[1-(4-fluoro-phenyl)-ethyl]-thioureido}-phenyl)-amide |
| 1071 | 471 | Isoquinoline-3-carboxylic acid (2-cyano-4-{3-[1-(4-fluoro-phenyl)-ethyl]-thioureido}-phenyl)-amide |
| 1072 | 460 | Isoquinoline-1-carboxylic acid (4-{3-[1-(4-fluoro-phenyl)-ethyl]-thioureido}-2-methyl-phenyl)-amide |
| 1073 | 449 | Benzofuran-2-carboxylic acid (4-{3-[1-(4-fluoro-phenyl)-ethyl]-thioureido}-2-methyl-phenyl)-amide |
| 1074 | 460 | Isoquinoline-3-carboxylic acid (4-{3-[1-(4-fluoro-phenyl)-ethyl]-thioureido}-2-methyl-phenyl)-amide |
| 1075 | 396 | Pyrazine-2-carboxylic acid (4-{3-[1-(4-fluoro-phenyl)-ethyl]-thioureido}-phenyl)-amide |
| 1076 | 401 | Thiophene-2-carboxylic acid (4-{3-[1-(4-fluoro-phenyl)-ethyl]-thioureido}-phenyl)-amide |
| 1077 | 401 | Thiophene-3-carboxylic acid (4-{3-[1-(4-fluoro-phenyl)-ethyl]-thioureido}-phenyl)-amide |
| 1078 | 500 | 2-Isopropyl-thiazole-4-carboxylic acid {4-[3-(4-chloro-3-trifluoromethyl-phenyl)-thioureido]-phenyl}-amide |
| 1079 | 466 | 2-Isopropyl-thiazole-4-carboxylic acid {4-[3-(3,5-dichloro-phenyl)-thioureido]-phenyl}-amide |
| 1080 | 466 | 2-Isopropyl-thiazole-4-carboxylic acid {4-[3-(3,4-dichloro-phenyl)-thioureido]-phenyl}-amide |
| 1081 | 534 | 2-Isopropyl-thiazole-4-carboxylic acid {4-[3-(3,5-bis-trifluoromethyl-phenyl)-thioureido]-phenyl}-amide |
| 1082 | 480 | 2-Butyl-thiazole-4-carboxylic acid {4-[3-(3,4-dichloro-phenyl)-thioureido]-phenyl}-amide |
| 1083 | 514 | 2-Butyl-thiazole-4-carboxylic acid {4-[3-(4-chloro-3-trifluoromethyl-phenyl)-thioureido]-phenyl}-amide |
| 1084 | 480 | 2-Butyl-thiazole-4-carboxylic acid {4-[3-(3,5-dichloro-phenyl)-thioureido]-phenyl}-amide |
| 1085 | 548 | 2-Butyl-thiazole-4-carboxylic acid {4-[3-(3,5-bis-trifluoromethyl-phenyl)-thioureido]-phenyl}-amide |
| 1086 | 438 | 2-Methyl-thiazole-4-carboxylic acid {4-[3-(3,5-dichloro-phenyl)-thioureido]-phenyl}-amide |
| 1087 | 438 | 2-Methyl-thiazole-4-carboxylic acid {4-[3-(3,4-dichloro-phenyl)-thioureido]-phenyl}-amide |
| 1088 | 505 | 2-Methyl-thiazole-4-carboxylic acid {4-[3-(3,5-bis-trifluoromethyl-phenyl)-thioureido]-phenyl}-amide |
| 1089 | 534 | 2-Phenyl-thiazole-4-carboxylic acid {4-[3-(4-chloro-3-trifluoromethyl-phenyl)-thioureido]-phenyl}-amide |
| 1090 | 500 | 2-Phenyl-thiazole-4-carboxylic acid {4-[3-(3,5-dichloro-phenyl)-thioureido]-phenyl}-amide |
| 1091 | 500 | 2-Phenyl-thiazole-4-carboxylic acid {4-[3-(3,4-dichloro-phenyl)-thioureido]-phenyl}-amide |
| 1092 | 568 | 2-Phenyl-thiazole-4-carboxylic acid {4-[3-(3,5-bis-trifluoromethyl-phenyl)-thioureido]-phenyl}-amide. |
| 1093 | 401 | 2-Fluoro-N-{4-[3-(1-thiazol-2-yl-ethyl)-thioureido]-phenyl}-benzamide |
| 1094 | 588 | 2-Fluoro-N-[4-(3-{1-[1-(toluene-4-sulfonyl)-1H-indol-2-yl]-ethyl}-thioureido)-phenyl]-benzamide |
| 1095 | 446 | 2-Fluoro-N-{4-[3-(1-quinolin-2-yl-ethyl)-thioureido]-phenyl}-benzamide |
| 1096 | 446 | 2-Fluoro-N-{4-[3-(1-quinolin-4-yl-ethyl)-thioureido]-phenyl}-benzamide |
| 1097 | 446 | 2-Fluoro-N-{4-[3-(1-isoquinolin-3-yl-ethyl)-thioureido]-phenyl}-benzamide |
| 1098 | 446 | 2-Fluoro-N-{4-[3-(1-isoquinolin-1-yl-ethyl)-thioureido]-phenyl}-benzamide |
| 1099 | 446 | 2-Fluoro-N-{4-[3-(1-quinolin-6-yl-ethyl)-thioureido]-phenyl}-benzamide |
| 1100 | 446 | 2-Fluoro-N-{4-[3-(1-quinolin-3-yl-ethyl)-thioureido]-phenyl}-benzamide |
| 1101 | 413 | 2-Methoxy-N-{4-[3-(1-thiophen-3-yl-ethyl)-thioureido]-phenyl}-benzamide |

EXAMPLE 871

(Method 33)

[1,2,3]Thiadiazole-4-carboxylic Acid {4-[3-(3,5-dichloro-phenyl)-thioureido]-phenyl}-amide To a solution of 3,5-dichloroaniline (0.16 g) in tetrahydrofuran (20 mL) is added freshly prepared 1,1'-thiocarbonyl-di-(1,2,4)-triazole (0.20 g) and the mixture is stirred for approximately 30 minutes at room temperature. [1,2,3]-Thiadiazole-4-carboxylic acid (4-amino-phenyl) amide (0.22 g) is added to the reaction flask and the mixture is stirred for approximately 6 hours. The solvent is then removed by evaporation under reduced pressure and warm acetonitrile (3 mL) is added. After 15 hours the mixture is filtered and the collected precipitate is washed with acetonitrile then diethyl ether, and air dried to provide the desired product as a white powder. [M+H]424.

Using the above procedure and appropriate starting materials the following compounds were prepared:

| EX. NO. | M + H | COMPOUND NAME |
|---|---|---|
| 872 | 465 | N-{4-[3-(3,5-Dichloro-4-methoxy-phenyl)-thioureido]-phenyl}-3-fluoro-benzamide |
| 873 | 477 | N-{4-[3-(3,5-Dichloro-4-methoxy-phenyl)-thioureido]-phenyl}-2-methoxy-benzamide |
| 874 | 465 | N-{4-[3-(3,5-Dichloro-4-methoxy-phenyl)-thioureido)-phenyl}-2-fluoro-benzamide |
| 875 | 477 | N-{4-[3-(3,5-Dichloro-4-methoxy-phenyl)-thioureido]-phenyl}-3-methoxy-benzamide |
| 876 | 399 | N-{4-[3-(3,5-Dichloro-2-methoxy-4-methyl-phenyl)-thioureido]-phenyl}-acetamide |
| 877 | 365 | N-{4-[3-(3-Chloro-4-methoxy-5-methyl-phenyl)-thioureido]-phenyl}-acetamide |
| 878 | 331 | N-{4-[3-(2-Nitro-phenyl)-thioureido]-phenyl}-acetamide |
| 879 | 331 | N-{4-[3-(4-Nitro-phenyl)-thioureido]-phenyl}-acetamide |
| 880 | 477 | N-{4-[3-(3,5-Dichloro-4-methoxy-phenyl)-thioureido]-phenyl}-4-methoxy-benzamide |
| 881 | 351 | N-{4-[3-(2-Chloro-5-methoxy-phenyl)-thioureido]-phenyl}-acetamide |
| 882 | 428 | 2-{4-[3-(4-Acetylamino-phenyl)-thioureido]-2,6-dichloro-phenoxy}-acetamide |
| 883 | 443 | {4-[3-(4-Acetylamino-phenyl)-thioureido]-2,6-dichloro-phenoxy}-acetic acid methyl ester |
| 884 | 457 | {4-[3-(4-Acetylamino-phenyl)-thioureido]-2,6-dichloro-phenoxy}-acetic acid ethyl ester |
| 885 | 447 | N-{4-[3-(3,5-Dichloro-4-phenoxy-phenyl)-thioureido]-phenyl}-acetamide |
| 886 | 410 | N-(4-{3-[3,5-Dichloro-4-(2-nitrilo-ethoxy)-phenyl]-thioureido}-phenyl)-acetamide |
| 887 | 485 | {4-[3-(4-Acetylamino-phenyl)-thioureido]-2,6-dichloro-phenoxy}-acetic acid tert-butyl ester |
| 888 | 469 | [1,2,3]Thiadiazole-4-carboxylic acid {4-[3-(3,5-dichloro-2-methoxy-4-methyl-phenyl)-thioureido]-phenyl}-amide |
| 889 | 335 | N-{4-[3-(3-Chloro-4-methyl-phenyl)-thioureido]-phenyl}-acetamide |
| 890 | 335 | N-{4-[3-(5-Chloro-2-methyl-phenyl)-thioureido]-phenyl}-acetamide |
| 891 | 703 | N{4-[3-(4-{4-[3-(4-Acetylamino-phenyl)-thioureido]-2-chloro-phenyldisulfanyl}-3-chloro-phenyl)-thioureido]-phenyl}-acetamide |
| 892 | 369 | N-{4-[3-(3,5-Dichloro-4-methyl-phenyl)-thioureido]-phenyl}-acetamide |
| 893 | 598 | N-{4-[3-(3,5-Diiodo-2,4-dimethoxy-phenyl)-thioureido]-phenyl}-acetamide |
| 894 | 504 | N-{4-[3-(3,5-Dibromo-2,4-dimethoxy-phenyl)-thioureido]-phenyl}-acetamide |
| 895 | 317 | N-{4-[3-(6-Methoxy-pyridin-3-yl)-thioureido]-phenyl}-acetamide |
| 896 | 347 | N-{4-[3-(2,6-Dimethoxy-pyridin-3-yl)-thioureido]-phenyl}-acetamide |
| 897 | 457 | Acetic acid 2-{4-[3-(4-acetylamino-phenyl)-thioureido]-2,6-dichloro-phenoxy}-ethyl ester |
| 898 | 365 | 4-[3-(4-Acetylamino-phenyl)-thioureido]-2-chloro-benzoic acid |
| 899 | 346 | N-{4-[3-(3-Chloro-4-cyano-phenyl)-thioureido]-phenyl}-acetamide |
| 900 | 512 | N-(4-{3-[5-Chloro-2-(4-chloro-phenoxy)-4-pyrrol-1-yl-phenyl]-thioureido}-phenyl)-acetamide |
| 901 | 355 | N-{4-[3-(3,4-Dichloro-phenyl)-thioureido]-phenyl}-acetamide |
| 902 | 339 | N-{4-[3-(3-Chloro-4-fluoro-phenyl)-thioureido]-phenyl}-acetamide |
| 903 | 447 | N-{4-[3-(3-Chloro-4-iodo-phenyl)-thioureido]-phenyl}-acetamide |
| 904 | 400 | N-{4-[3-(4-Bromo-3-chloro-phenyl)-thioureido]-phenyl}-acetamide |
| 905 | 424 | N-[4-(3-{4-[Bis-(2-hydroxy-ethyl)-amino]-3-chloro-phenyl}-thioureido)-phenyl]-acetamide |
| 906 | 434 | N-(4-{3-[3-Chloro-4-(hexyl-methyl-amino)-phenyl]-thioureido}-phenyl)-acetamide |
| 907 | 406 | N-(4-{3-[3-Chloro-4-(isobutyl-methyl-amino)-phenyl]-thioureido}-phenyl)-acetamide |
| 908 | 389 | N-{4-[3-(3-Chloro-4-trifluoromethyl-phenyl)-thioureido]-phenyl}-acetamide |
| 909 | 441 | Furan-2-carboxylic acid {4-[3-(3-chloro-4-trifluoromethyl-phenyl)-thioureido]-phenyl}-amide |
| 910 | 459 | [1,2,3]Thiadiazole-4-carboxylic acid {4-[3-(3-chloro-4-trifluoromethyl-phenyl)-thioureido]-phenyl}-amide |
| 911 | 469 | N-{4-[3-(3-Chloro-4-trifluoromethyl-phenyl)-thioureido]-phenyl}-2-fluoro-benzamide |
| 912 | 435 | N-{4-[3-(3,4-Dichloro-phenyl)-thioureido]-phenyl}-2-fluoro-benzamide |
| 913 | 407 | Furan-2-carboxylic acid {4-[3-(3,4-dichloro-phenyl)-thioureido]-phenyl}-amide |
| 914 | 425 | [1,2,3]Thiadiazole-4-carboxylic acid {4-[3-(3,4-dichloro-phenyl)-thioureido]-phenyl}-amide |
| 915 | 480 | N-{4-[3-(4-Bromo-3-chloro-phenyl)-thioureido]-phenyl}-2-fluoro-benzamide |
| 916 | 527 | N-{4-[3-(3-Chloro-4-iodo-phenyl)-thioureido]-phenyl}-2-fluoro-benzamide |
| 917 | 452 | Furan-2-carboxylic acid {4-[3-(4-bromo-3-chloro-phenyl)-thioureido]-phenyl}-amide |
| 918 | 499 | Furan-2-carboxylic acid {4-[3-(3-chloro-4-iodo-phenyl)-thioureido]-phenyl}-amide |
| 919 | 391 | Furan-2-carboxylic acid {4-[3-(3-chloro-4-fluoro-phenyl)-thioureido]-phenyl}-amide |
| 920 | 470 | [1,2,3]Thiadiazole-4-carboxylic acid {4-[3-(4-bromo-3-chloro-phenyl)-thioureido]-phenyl}-amide |
| 921 | 517 | [1,2,3]Thiadiazole-4-carboxylic acid {4-[3-(3-chloro-4-iodo-phenyl)-thioureido]-phenyl}-amide |
| 922 | 419 | N-{4-[3-(3-Chloro-4-fluoro-phenyl)-thioureido]-phenyl}-2-fluoro-benzamide |
| 923 | 409 | [1,2,3]Thiadiazole-4-carboxylic acid{4-[3-(3-chloro4-fluoro-phenyl)-thioureido]-phenyl}-amide |
| 924 | 388 | N-{4-[3-(3-Chloro-4-isoxazol-5-yl-phenyl)-thioureido]-phenyl}-acetamide |
| 925 | 387 | N-(4-{3-[3-Chloro-4-(1H-pyrazol-3-yl)-phenyl]-thioureido}-phenyl)-acetamide |
| 926 | 355 | N-{4-[3-(2,3-Dichloro-phenyl)-thioureido]-phenyl}-acetamide |
| 927 | 435 | N-{4-[3-(2,3-Dichloro-phenyl)-thioureido]-phenyl}-2-fluoro-benzamide |
| 928 | 407 | Furan-2-carboxylic acid {4-[3-(2,3-dichloro-phenyl)-thioureido]-phenyl}-amide |
| 929 | 425 | [1,2,3]Thiadiazole-4-carboxylic acid {4-[3-(2,3-dichloro-phenyl)-thioureido]-phenyl}-amide |
| 930 | 355 | N-{4-[3-(2,5-Dichloro-phenyl)-thioureido]-phenyl}-acetamide |
| 931 | 435 | N-{4-[3-(2,5-Dichloro-phenyl)-thioureido]-phenyl}-2-fluoro-benzamide |
| 932 | 407 | Furan-2-carboxylic acid {4-[3-(2,5-dichloro-phenyl)-thioureido]-phenyl}-amide |
| 933 | 355 | N-{4-[3-(3,5-Dichloro-phenyl)-thioureido]-phenyl}-acetamide |
| 934 | 435 | N-{4-[3-(3,5-Dichloro-phenyl)-thioureido]-phenyl}-2-fluoro-benzamide |
| 935 | 407 | Furan-2-carboxylic acid {4-[3-(3,5-dichloro-phenyl)-thioureido]-phenyl}-amide |
| 936 | 390 | N-{4-[3-(3,4,5-Trichloro-phenyl)-thioureido]-phenyl}-acetamide |
| 937 | 470 | 2-Fluoro-N-{4-[3-(3,4,5-trichloro-phenyl)-thioureido]-phenyl}-benzamide |
| 938 | 442 | Furan-2-carboxylic acid {4-[3-(3,4,5-trichloro-phenyl)-thioureido]-phenyl}-amide |
| 939 | 460 | [1,2,3]Thiadiazole-4-carboxylic acid{4-[3-(3,4,5-trichloro-phenyl)-thioureido]-phenyl}-amide |
| 940 | 458 | [1,2,3]Thiadiazole-4-carboxylic acid {4-[3-(3-chloro-4-isoxazol-5-yl-phenyl)-thioureido]-phenyl}-amide |
| 941 | 457 | [1,2,3]Thiadiazole-4-carboxylic acid(4-{3-[3-chloro-4-(1H-pyrazol-3-yl)-phenyl]-thioureido}-phenyl)-amide |
| 942 | 391 | [1,2,3]Thiadiazole-4-carboxylic acid {4-[3-(3-chloro-phenyl)-thioureido]-phenyl}-amide |
| 943 | 373 | Furan-2-carboxylic acid {4-[3-(3-chloro-phenyl)-thioureido]-phenyl}-amide |
| 944 | 401 | N-{4-[3-(3-Chloro-phenyl)-thioureido]-phenyl}-2-fluoro-benzamide |
| 945 | 373 | Furan-2-carboxylic acid {4-[3-(4-chloro-phenyl)-thioureido]-phenyl}-amide |
| 946 | 401 | N-{4-[3-(4-Chloro-phenyl)-thioureido]-phenyl}-2-fluoro-benzamide |
| 947 | 391 | [1,2,3]Thiadiazole-4-carboxylic acid {4-[3-(4-chloro-phenyl)-thioureido]-phenyl}-amide |

-continued

| EX. NO. | M + H | COMPOUND NAME |
|---|---|---|
| 948 | 401 | N-{4-[3-(2-Chloro-phenyl)-thioureido]-phenyl}-2-fluoro-benzamide |
| 949 | 396 | 3-(3-{4-[(Furan-2-carbonyl)-amino]-phenyl}-thioureido)-benzoic acid methyl ester |
| 950 | 424 | 3-{3-[4-(2-Fluoro-benzoylamino)-phenyl]-thioureido}-benzoic acid methyl ester |
| 951 | 414 | 3-(3-{4-[([1,2,3]Thiadiazole-4-carbonyl)-amino]-phenyl}-thioureido)-benzoic acid methyl ester |
| 952 | 409 | N-[4-[[[[3-(Aminocarbonyl)phenyl]amino]thioxomethyl]amino]phenyl]-2-fluoro-benzamide |
| 953 | 373 | Furan-2-carboxylic acid {4-[3-(2-chloro-phenyl)-thioureido]-phenyl}-amide |
| 954 | 381 | Furan-2-carboxylic acid {4-[3-(3-carbamoyl-phenyl)-thioureido]-phenyl}-amide |
| 955 | 399 | [1,2,3]Thiadiazole-4-carboxylic acid {4-[3-(3-carbamoyl-phenyl)-thioureido]-phenyl}-amide |
| 956 | 391 | [1,2,3]Thiadiazole-4-carboxylic acid {4-[3-(2-chloro-phenyl)-thioureido]-phenyl}-amide |
| 957 | 356 | Furan-2-carboxylic acid {4-[3-(3-fluoro-phenyl)-thioureido]-phenyl}-amide |
| 958 | 383 | Furan-2-carboxylic acid {4-[3-(3-nitro-phenyl)-thioureido]-phenyl}-amide |
| 959 | 411 | 2-Fluoro-N-{4-[3-(3-nitro-phenyl)-thioureido]-phenyl}-benzamide |
| 960 | 422 | Furan-2-carboxylic acid {4-[3-(3-trifluoromethoxy-phenyl)-thioureido]-phenyl}-amide |
| 961 | 450 | 2-Fluoro-N-{4-[3-(3-trifluoromethoxy-phenyl)-thioureido]-phenyl}-benzamide |
| 962 | 384 | 2-Fluoro-N-{4-[3-(3-fluoro-phenyl)-thioureido]-phenyl}-benzamide |
| 963 | 410 | 3-{3-[4-(2-Fluoro-benzoylamino)-phenyl]-thioureido}-benzoic acid |
| 964 | 382 | 3-(3-{4-[(Furan-2-carbonyl)-amino]-phenyl}-thioureido)-benzoic acid |
| 965 | 408 | N-{4-[3-(3-Acetyl-phenyl)-thioureido]-phenyl}-2-fluoro-benzamide |
| 966 | 502 | N-{4-[3-(3-Butylsulfamoyl-phenyl)-thioureido]-phenyl}-2-fluoro-benzamide |
| 967 | 380 | Furan-2-carboxylic acid {4-[3-(3-acetyl-phenyl)-thioureido]-phenyl}-amide |
| 968 | 447 | Furan-2-carboxylic acid (4-{3-[3-(2-hydroxy-ethanesulfonyl)-phenyl]-thioureido}-phenyl)-amide |
| 969 | 475 | 2-Fluoro-N-(4-{3-[3-(2-hydroxy-ethanesulfonyl)-phenyl]-thioureido}-phenyl)-benzamide |
| 970 | 474 | Furan-2-carboxylic acid {4-[3-(3-butylsulfamoyl-phenyl)-thioureido]-phenyl}-amide |

EXAMPLE 971

(Method 57)

1-(4-Fluoro-phenyl)-2-methyl-propan-1-ol

To solution of 4-fluorobenzaldehyde (2.0 g) in diethyl ether (40 mL) at 0° C. is added dropwise isopropylmagesium bromide (2.0 M, 9.6 mL) with stirring. After 1.5 hours the reaction is quenched with aqueous ammonium chloride and extracted with diethyl ether. The diethyl ether extracts are washed with saturated sodium chloride, dried over anhydrous magnesium sulfate, flitered and evaporated to give an oil. The oil is purifed by silica gel chromatography eluting with 10% dichloromethane-hexanes to give the product, a yellow oil (1.76 g).

EXAMPLE 972

(Method 58)

1-(4-Fluoro-phenyl)-2-methyl-propan-1-one

To a solution of 1-(4-Fluoro-phenyl)-2-methyl-propan-1-ol (1.6 g) in acetone (10 mL) at 0° C. is added Jones reagent (20 mL) with stirring. After 10 minutes excess Jones reagent is destroyed by addition of isopropyl alcohol. Diethyl ether is added followed by anhydrous magnesium and the mixture is filtered and evaporated to give the product, a yellow oil (1.2 g).

EXAMPLE 973

(Method 59)

3-Dimethylamino-5-trifluoromethyl-benzonitrile

To a solution of 3-dimethylamino-5-trifluoromethylbromobenzene (7.3 g) in N,N-dimethylformamide (20 mL) is added cuprous cyanide (2.7 g) and the reaction heated at reflux for 12 hours. The reaction is diluted with water (40 mL) and dichloromethane is added. The dichloromethane fraction is washed with concentrated ammonium hydroxide, then water. The solution is dried over anhydrous magnesium sulfate, filtered and concentrated to give a yellow solid which is recrystallized from hexanes to give a yellow solid, (4.7 g).

The foregoing compounds were tested for activity as herpes virus inhibitors using the following assays.

HUMAN CYTOMEGALOVIRUS

Yield assay. Monolayer cultures of human foreskin fibroblasts are infected with HCMV wild-type, typically at a multiplicity of infection equal to 0.2, in the presence of inhibitor compound (varying concentrations). At three days post-infection, total virus produced in these cultures (i.e. virus yield) is assessed by harvesting and titering the virus in 12-well plates of cultured human foreskin fibroblasts (done in the absence of inhibitor). Plaques are quantified at 2 weeks post-infection. An inhibitor of HCMV is identified by the reduction in titer of virus yield in the presence, compared to the titer in the absence of compound. In this assay, the relative anti-HCMV activity of an inhibitor is typically determined by calculating the $IC_{50}$ or $IC_{90}$ value, that is, the amount of compound required to reduce the virus yield by 50% or 90%, respectively. Table I describes $IC_{50}$ data for compounds tested against HCMV.

Microtiter plate assay. Ninety-six well plate cultures of human foreskin fibroblasts are infected in the presence of inhibitor compound with a HCMV recombinant mutant virus whose genome contains the prokaryotic beta-glucuronidase gene (Jefferson, R. A., S. M. Burgess, and D. Hirsh. 1986. Beta-glucuronidase from *Escherichia coli* as a gene fusion marker. Proc. Natl. Acad. Sci. USA 83:8447–8451) whose expression is controlled by a viral promoter. An example of such a virus is RV145 (Jones, T. R., V. P. Muzithras, and Y. Oluzman. 1991. Replacement mutagenesis of the human cytomegalovirus genome: US10 and US11 gene products are nonessential. J. Virol.

65:5860–5872). Since it is under the control of a viral promoter, beta-glucuronidase expression is an indirect indicator of growth and replication of HCMV in this assay. At 96 hours post-infection, the infected cell lysates are prepared (using 50 mM sodium phosphate [pH7.0] containing 0.1% Triton X-100 and 0.1% sarkosyl) and assayed for beta-glucuronidase activity using a substrate for the enzyme which when cleaved yields either a product which can be measured colorimetrically in a spectrophotometer or fluorescently in a microfluorimeter. Examples of such substrates are p-nitrophenyl-beta-D-glucuronide and methylumbelliferylglucuronide, respectively. The presence of an antiviral compound is indicated by the reduced expression of the HCMV genome resident beta-glucuronidase gene, compared to the absence of inhibitor. Thus, the generation of the chromophore or fluorophore product in this assay is correspondingly reduced.

Data from this assay generated using varying amounts of inhibitor compound is also used to estimate the IC50 of an inhibitor compound.

HSV Antiviral (ELISA) Assay

Vero cells (ATCC #CCL-81) are plated on 96-well tissue culture plates at $3.5 \times 10^4$ cells per 100wp tissue culture DMEM (Dulbecco's modified Eagle media) supplemented with 2% fetal bovine serum (FBS) in each well. After overnight incubation @ 37° C. (in 5% $CO_2$) and 30 minutes prior to infection with HSV-1 (multiplicity of infection equal to 0.006), cells are either untreated, or treated with test compound (multiple concentrations) or reference standard drug control. After approximately 24 hours post-infection incubation @ 37° C. (in 5% $CO_2$), cells are fixed for ELISA assay. The primary antibody is murine anti-HSV glycoprotein D monoclonal primary antibody and the secondary antibody is goat anti-mouse IgG linked to B-galactosidase. Thus the extent of viral replication is determined by assessing 6-galactosidase activity by quantifying the generation of the 4-methyl umbelliferone fluorescent cleavage product after addition of the methyl umbelliferyl-B-D-galactoside (Sigma #M1633) substrate on a microfluorimeter (365nm for excitation and 450nm for emission). Antiviral activity (IC50) of the test compound is determined by comparing the flourescence obtained in absence of compound to that obtained in the presence of compound. Data is shown in Table I.

VZV Antiviral (ELISA) Assay

For the generation of stock VZV to be used in the assay, VZV strain Ellen (ATCC #VR-1367 is used to infect human foreskin fibroblast (HFF) cells at low multiplicity (less than 0.1) and incubated overnight at 37° C. in 5% CO,. After the overnight incubation, the mixture of uninfected and VZV-infected HFF infected cells are then harvested and added to each well of 96-well plates ($3.5 \times 10^4$ cells in 100 μl DMEM supplemented with 2% FBS) which contain test compound or the reference standard drug control (in 100 μl DMEM supplemented with 2% FBS per well). These cells are incubated for three days at 37° C. in 5% $CO_2$, then fixed for ELISA assay. The primary antibody is murine anti-VZV glycoprotein II monoclonal antibody (Applied Biosystems, Inc. #13-145-100) and the secondary antibody is goat anti-mouse IgG linked to β-galactosidase. Thus the extent of viral replication is determined by assessing β-galactosidase activity by quantifying the generation of the 4-methyl umbelliferone fluorescent cleavage product after addition of the methyl umbelliferyl-β-D-galactoside (Sigma #M1633) substrate on a microfluorimeter (365 nm for excitation and 450 nm for emission). Antiviral activity ($IC_{50}$) of the test compound is determined by comparing the flourescence obtained in absence of compound to that obtained in the presence of compound. Data is shown in Table I.

TABLE 1 describes $IC_{50}$ data for compounds tested against herpes viruses.

| Example | IC50 (ug/ml) HCMV | IC50 (ug/ml) HSV | % inhibition 10 ug/ml VZV | IC50 (ug/ml) VZV |
|---|---|---|---|---|
| 426 | 1.6 | >10 | 2 | 1.8 |
| 427 | 0.8 | >10 | 21 | 1.2 |
| 428 | >10 | >10 | 0 | >10 |
| 429 | 1 | >10 | 0 | >10 |
| 443 | >10 | >10 | 0 | >10 |
| 444 | 4 | 8 | 0 | >10 |
| 471 | 0.03 | >10 | 27 | >10 |
| 480 | 7 | >10 | 42 | >10 |
| 483 | 5 | 1.2 | 45 | >10 |
| 520 | 0.32 | 12 | 38 | >10 |
| 525 | 0.018 | 2.5 | 39 | >10 |
| 593 | >0.5 | 10 | | >10 |
| 608 | >0.5 | 9 | | >10 |
| 609 | 1.5 | 8 | | >10 |
| 629 | 0.5 | >10 | | >10 |
| 632 | >10 | >10 | | >10 |
| 633 | 0.34 | >10 | | >10 |
| 634 | 0.12 | >10 | | >10 |
| 649 | 0.02 | >10 | | 0.5 |
| 658 | >0.5 | 10 | | |
| 659 | >0.5 | >10 | | |
| 660 | >0.5 | 10 | | |
| 802 | >10 | >10 | | 7.3 |
| 803 | >10 | >10 | | >7.5 |
| 804 | >10 | >10 | | 5.7 |
| 805 | 8 | >10 | | 1.6 |
| 1093 | >10 | >10 | | >10 |
| 1094 | >10 | >10 | | >7.5 |
| 1095 | 2.4 | >10 | | 7.1 |
| 1096 | 5.7 | >10 | | 6.7 |
| 1097 | 4 | >10 | | 5.50 |
| 1098 | 3.5 | 9 | | 3.80 |
| 1099 | 5.6 | >10 | | >7.5 |
| 1100 | 4.6 | >10 | | 7.3 |
| 1101 | >10 | >10 | | 1 |

Thus, in accordance with the present invention, compounds of the present invention may be administered to a patient suffering from VZV, in an amount effective to inhibit the virus. Compounds of the present invention are thus useful to ameliorate to eliminate the symptoms of VZV infections in mammals including, but not limited to humans.

Compounds of the invention may be administered to a patient either neat or with a convention pharmaceutical carrier.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The therapeutically effective dosage to be used in the treatment of CMV infection must be subjectively determined by the attending physician. The variables involved include the the condition, age and weight of the patient. The novel method of the invention for treating CMV infection comprises administering toa subject, including humans, an effective amount of at least one compound of Formula 1 or a non-toxic, pharmaceutically acceptable salt thereof. The compounds may be administered orally, rectally, parenterally or topically to the skin and mucosa. The usual daily dose is depending on the specific compound, method of treatment and condition of the patient. The usual daily dose is 0.01–1000 mg/Kg for oral application, preferably 0.5–500 mg/Kg, and 0.1–100 mg/Kg for parenteral application, preferably 0.5–50 mg/Kg.

What is claimed:
1. A compound of the formula:

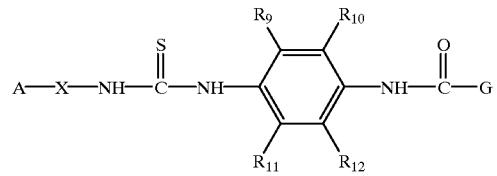

wherein
A is pyridyl, imidazolyl, pyrolyl or indazolyl;
$R_1$–$R_{12}$ are independently hydrogen, alkyl of 1 to 4 carbon atoms, perhaloalkyl of 1 to 4 carbon atoms, halogen, alkoxy of 1 to 4 carbon atoms, or cyano, or $R_9$ and $R_{10}$ or $R_{11}$ and $R_{12}$ may be taken together to form aryl of 5 to 7 carbon atoms;
W is O, $NR_6$, or is absent;
G is aryl or heteroaryl;
X is a bond, —NH, alkyl of 1 to 6 carbon atoms, alkenyl of 1 to 6 carbon atoms, alkoxy of 1 to 6 carbon atoms, thioalkyl of 1 to 6 carbon atoms, alkylamino of 1 to 6 carbon atoms, or (CH)J; and
J is alkyl of 1 to 6 carbon atoms, cycloalkyl of 3 to 7 carbon atoms, phenyl or benzyl; and
n is an integer from 1 to 6; or a pharmaceutically acceptable salt thereof.
2. A compound of claim 1 wherein A is selected from pyridyl, imidazolyl, or pyrrolyl.
3. A compound of claim 1 wherein A is 3-pyridyl.
4. A compound of claim 1 wherein A is substituted.
5. A compound of claim 1 wherein A is substituted with one or more substitutents selected from alkyl of 1 to 6 carbon atoms, alkenyl of 2 to 6 carbon atoms, alkynyl of 2 to 6 carbon atoms, perhaloalkyl of 1 to 6 carbon atoms, cycloalkyl of 3 to 10 carbon atoms, heterocycloalkyl of 3 to 10 carbon members, aryl, heteroaryl, halogen, —CN, —$NO_2$, —$CO_2R_6$, —$COR_6$, —$OR_6$, —$SR_6$, —$SOR_6$, —$SO_2R_6$, —$CONR_7R_8$, —$NR_6N(R_7R_8)$, —$N(R_7R_8)$, or W—Y—$(CH_2)_n$—Z wherein $R_6$ and $R_7$ are independently hydrogen, alkyl of 1 to 6 carbon atoms, perhaloalkyl of 1 to 6 carbon atoms, or aryl; $R_8$ is hydrogen, alkyl of 1 to 6 carbon atoms, perhaloalkyl of 1 to 6 carbon atoms, cycloalkyl of 3 to 10 carbon atoms, heterocycloalkyl of 3 to 10 members, aryl or heteroaryl, or
$R_7$ and $R_8$, taken together may form a 3 to 7 membered heterocycloalkyl;
W is O, $NR_6$, or is absent;
Y is —(CO)— or —($CO_2$)—, or is absent;
Z is alkyl of 1 to 4 carbon atoms, —CN, —$CO_2R_6$, $COR_6$, —$CONR_7R_8$, —$OCOR_6$, —$NR_6COR_7$, —$OCONR_6$, —$OR_6$, —$SR_6$, —$SOR_6$, —$SO_2R_6$, $SR_6N(R_7R_8)$, —$N(R_7R_8)$ or phenyl;
and n is 1 to 6.
6. A compound of claim 1 wherein A is substituted with one or more substitutents independently selected from halogen or alkyl of 1 to 6 carbon atoms.
7. A compound of claim 1 wherein one or more of $R_7$–$R_{12}$ is independently selected from halogen, methyl, methoxy, and cyano.
8. A compound of claim 1 wherein each of $R_1$–$R_9$ is hydrogen.

9. A compound of claim 1 wherein G is furyl or thiadiazole.

10. A compound of claim 1 wherein G is 1,2,3 thiadiazole.

11. A compound of claim 1 wherein G is 2-furyl.

12. A compound of claim 1 wherein X is a bond.

13. A compound of claim 1 wherein X is lower alkyl.

14. A compound of claim 1 selected from:
Furan-2-carboxylic acid [4-(3-pyridin-2-yl-thioureido)-phenyl]-amide;
Furan-2-carboxylic acid [4-(3-pyridin-4-yl-thioureido)-phenyl]-amide;
Furan-2-carboxylic acid [4-(3-pyridin-3-yl-thioureido)-phenyl]-amide;
[1,2,3]Thiadiazole-4-carboxylic acid {4-[3-(6-chloro-pyridin-3-yl)-thioureido]-phenyl}-amide;
[1,2,3]Thiadiazole-4-carboxylic acid {4-[3-(5-chloro-pyridin-3-yl)-thioureido]-phenyl}-amide;
[1,2,3]Thiadiazole-4-carboxylic acid {4-[3-(5-bromo-pyridin-3-yl)-thioureido]-phenyl}-amide;
[1,2,3]Thiadiazole-4-carboxylic acid {4-[3-(1-tert-butyl-1H-imidazol-2-yl)-thioureido]-phenyl}-amide;
Furan-2-carboxylic acid (4-[3-(1-tert-butyl-1H-imidazol-2-yl)-thioureido]-phenyl}-amide;
[1,2,3]Thiadiazole-4-carboxylic acid {4-[3-(5-trifluoromethyl-pyridin-3-yl)-thioureido]-phenyl}-amide;
Furan-2-carboxylic acid [4-(3-pyridin-3-ylmethyl-thioureido)-phenyl]-amide;
[1,2,3]Thiadiazole-4-carboxylic acid [4-(3-pyridin-3-ylmethyl-thioureido)-phenyl]-amide;
Furan-2-carboxylic acid [4-(3-pyridin-4-ylmethyl-thioureido)-phenyl]-amide;
[1,2,3]Thiadiazole-4-carboxylic acid [4-(3-pyridin-4-ylmethyl-thioureido)-phenyl]-amide;
2-Fluoro-N-[4-(3-pyridin-3-yl-thioureido)-phenyl]-benzamide;
2-Fluoro-N-[4-(3-pyridin-2-yl-thioureido)-phenyl]-benzamide;
2-Fluoro-N-[4-(3-pyridin-4-yl-thioureido)-phenyl]-benzamide;
2-Fluoro-N-[4-(3-pyridin-3-ylmethyl-thioureido)-phenyl]-benzamide;
2-Fluoro-N-{4-[3-(1H-indazol-5-yl)-thioureido]-phenyl}-benzamide;
N-{4-[3-(1-tert-Butyl-1H-imidazol-2-yl)-thioureido]-phenyl}-2-fluoro-benzamide;
2-Fluoro-N-[4-(3-pyridin-4-ylmethyl-thioureido)-phenyl]-benzamide;
2-Fluoro-N-{4-[3-(1-pyridin-4-yl-ethyl)-thioureido]-phenyl}-benzamide; and
2-Fluoro-N-(4-{3-[1-(1-methyl-1H-pyrrol-2-yl)-ethyl]-thioureido}-phenyl)-benzamide;
and pharmaceutically acceptable salts thereof.

15. A pharmaceutical composition comprising a compound of the formula:

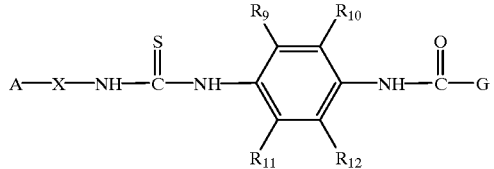

wherein

A is pyridyl, imidazolyl, pyrolyl, or indazolyl;

$R_1$–$R_{12}$ are independently hydrogen, alkyl of 1 to 4 carbon atoms, perhaloalkyl of 1 to 4 carbon atoms, halogen, alkoxy of 1 to 4 carbon atoms, or cyano, or $R_9$ and $R_{10}$ or $R_{11}$ and $R_{12}$ may be taken together to form aryl of 5 to 7 carbon atoms;

W is O, $NR_6$, or is absent;

G is aryl or heteroaryl;

X is a bond X is a bond, —NH, alkyl of 1 to 6 carbon atoms, alkenyl of 1 to 6 carbon atoms, alkoxy of 1 to 6 carbon atoms, or thioalkyl of 1 to 6 carbon atoms, alkylamino of 1 to 6 carbon atoms, or (CH)J; and J is alkyl of 1 to 6 carbon atoms, cycloalkyl of 3 to 7 carbon atoms, phenyl or benzyl, or a pharmaceutically acceptable salt thereof; and n is an integer from 1 to 6; and a pharmaceutically acceptable carrier or diluent.

16. A method of inhibiting the replication of a herpes virus comprising contacting a compound of the formula:

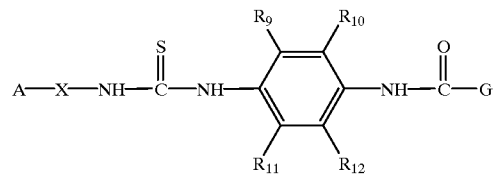

wherein

A is pyridyl, imidazolyl, pyrolyl or indazolyl;

$R_9$–$R_{12}$ are independently hydrogen, alkyl of 1 to 4 carbon atoms, perhaloalkyl of 1 to 4 carbon atoms, halogen, alkoxy of 1 to 4 carbon atoms, or cyano, or $R_9$ and $R_{10}$ or $R_{11}$ and $R_{12}$ may be taken together to form aryl of 5 to 7 carbon atoms;

W is O, $NR_6$, or is absent;

G is aryl or heteroaryl;

X is a bond X is a bond, —NH, alkyl of 1 to 6 carbon atoms, alkenyl of 1 to 6 carbon atoms, alkoxy of 1 to 6 carbon atoms, or thioalkyl of 1 to 6 carbon atoms, alkylamino of 1 to 6 carbon atoms, or (CH)J; and J is alkyl of 1 to 6 carbon atoms, cycloalkyl of 3 to 7 carbon atoms, phenyl or benzyl; and n is an integer from 1 to 6; or a pharmaceutically acceptable salt thereof, with a herpes virus.

17. The method of claim 16 wherein the herpes virus is human cytomegalovirus.

18. The method of claim 16 wherein the herpes virus is herpes simplex virus.

19. The method of claim 16 wherein the herpes virus is varicella zoster virus.

20. A method of treating a patient suffering from a herpes virus infection comprising administering to the patient a therapeutically effective amount of a compound having the formula:

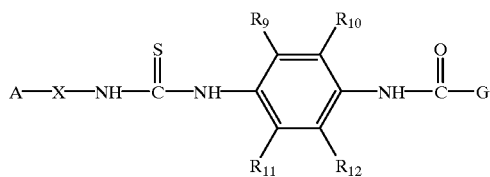

wherein

A is pyridyl, imidazolyl, pyrolyl or indazolyl;

$R_1$–$R_{12}$ are independently hydrogen, alkyl of 1 to 4 carbon atoms, perhaloalkyl of 1 to 4 carbon atoms, halogen, alkoxy of 1 to 4 carbon atoms, or cyano, or $R_9$ and $R_{10}$ or $R_{11}$ and $R_{12}$ may be taken together to form aryl of 5 to 7 carbon atoms;

W is O, $NR_6$, or is absent;

G is aryl or heteroaryl;

X is a bond X is a bond, —NH, alkyl of 1 to 6 carbon atoms, alkenyl of 1 to 6 carbon atoms, alkoxy of 1 to 6 carbon atoms, thioalkyl of 1 to 6 carbon atoms, alkylamino of 1 to 6 carbon atoms, or (CH)J; and J is alkyl of 1 to 6 carbon atoms, cycloalkyl of 3 to 7 carbon atoms, phenyl or benzyl; and n is an integer from 1 to 6; or a pharmaceutically acceptable salt thereof.

21. The method of claim 20 wherein the herpes virus is human cytomegalovirus.

22. The method of claim 20 wherein the herpes virus is herpes simplex virus.

23. The method of claim 20 where the herpes virus is varicella zoster virus.

* * * * *